US007238469B2

(12) United States Patent
Bach et al.

(10) Patent No.: US 7,238,469 B2

(45) Date of Patent: Jul. 3, 2007

(54) CARBON MONOXIDE IMPROVES OUTCOMES IN TISSUE AND ORGAN TRANSPLANTS AND SUPPRESSES APOPTOSIS

(75) Inventors: Fritz H. Bach, Manchester-by-the-Sea, MA (US); Leo E. Otterbein, New Kensington, PA (US); Miguel P. Soares, Boston, MA (US); Jeanne Gose, Manchester-by-the-Sea, MA (US)

(73) Assignees: Beth Israel Deaconess Medical Center, Inc., Boston, MA (US); Yale University, New Haven, CT (US)

( * ) Notice: Subject to any disclaimer, the term of this patent is extended or adjusted under 35 U.S.C. 154(b) by 0 days.

(21) Appl. No.: 10/177,930

(22) Filed: Jun. 21, 2002

(65) Prior Publication Data

US 2003/0039638 A1 Feb. 27, 2003

Related U.S. Application Data

(60) Provisional application No. 60/337,974, filed on Dec. 7, 2001, provisional application No. 60/334,340, filed on Nov. 29, 2001, provisional application No. 60/300,289, filed on Jun. 21, 2001.

(51) Int. Cl.
*A61K 61/00* (2006.01)
*A01N 1/00* (2006.01)

(52) U.S. Cl. .......................................... 435/1.1; 514/1

(58) Field of Classification Search ................. 514/762
See application file for complete search history.

(56) References Cited

U.S. PATENT DOCUMENTS

| | | | | |
|---|---|---|---|---|
| 4,053,590 | A | 10/1977 | Bonsen et al. | |
| 4,264,739 | A | 4/1981 | Grabner et al. | |
| 4,923,817 | A | 5/1990 | Mundt | |
| 5,084,380 | A | 1/1992 | Carney | |
| 5,180,366 | A | 1/1993 | Woods | |
| 5,240,912 | A | 8/1993 | Todaro | |
| 5,293,875 | A | 3/1994 | Stone | |
| 5,449,665 | A | 9/1995 | Sollevi | |
| 5,476,764 | A | 12/1995 | Bitensky | |
| 5,664,563 | A | 9/1997 | Schroeder et al. | |
| 5,731,326 | A | 3/1998 | Hart et al. | |
| 5,763,431 | A | 6/1998 | Jackson | |
| 5,792,325 | A | 8/1998 | Richardson, Jr. | |
| 5,882,674 | A | 3/1999 | Herrmann et al. | |
| 5,885,621 | A | 3/1999 | Head et al. | |
| 5,914,316 | A | 6/1999 | Brown et al. | |
| 6,066,333 | A | 5/2000 | Willis et al. | |
| 6,069,132 | A | 5/2000 | Revanker et al. | |
| 6,203,991 | B1 | 3/2001 | Nabel et al. | |
| 6,313,144 | B1 | 11/2001 | McCullough et al. | |
| 6,316,403 | B1 | 11/2001 | Pinsky et al. | |
| 7,045,140 | B2 | 5/2006 | Motterlini et al. | |
| 2003/0009127 | A1 | 1/2003 | Trescony et al. | |
| 2003/0064114 | A1 | 4/2003 | Motterlini et al. | |
| 2003/0068387 | A1* | 4/2003 | Buelow et al. | 424/699 |
| 2004/0067261 | A1 | 4/2004 | Haas et al. | |
| 2004/0197271 | A1 | 10/2004 | Kunka et al. | |
| 2005/0048133 | A1* | 3/2005 | Pinsky et al. | 424/699 |
| 2005/0250688 | A1 | 11/2005 | Pinsky et al. | |

FOREIGN PATENT DOCUMENTS

| | | |
|---|---|---|
| FR | 2 816 212 | 5/2002 |
| JP | 56079957 A | 6/1981 |
| WO | WO 94/22482 | 10/1994 |
| WO | WO 95/35105 | 12/1995 |
| WO | WO 98/08523 | 3/1998 |
| WO | WO 98/13058 | 4/1998 |
| WO | WO 99/47512 | 9/1999 |
| WO | WO 99/49880 | 10/1999 |
| WO | WO 02/09731 | 2/2002 |
| WO | WO 02/078684 | 10/2002 |
| WO | WO 02/092075 | 11/2002 |
| WO | WO 03/000114 | 1/2003 |

OTHER PUBLICATIONS

Appel et al., "The pig as a source of cardiac xenografts", Journal of Cardiac Surgery 16 (5) : 345-56 (Sep. 2001).*

Mori et al., "Evaluation of hypothermic heart preservation with UW solution in heteoptopically and orthotopically transplanted canine hearts", J. Heart and Lung Transplantation 13 (4) : 688-95 (1994).*

Abidin et al., "The combined effect of carbon monoxide and normobaric hyperoxia on animals," *Kosmicheskaya Biologiya I Aviakosmicheskaya Meditsina* (1978), No. 6, 63-67.

Arita et al., "Prevention of Primary Islet Isograft Nonfunction in Mice with Pravastatin," *Transplantation*, 65:1429-33, 1998.

Arnush et al., "IL-1 Produced and Released Endogenously within Human Islets Inhibits β Cell Function," *J. Clin Invest.* 702:516-26, 1998.

Bach et al., "Accommodation of vascularized xenografts: Expression of "protective genes" by donor endothelial cells in a host Th2 cytokine environment," *Nature Med.* 3:196-202,1997.

Berney et al., "Islet cell transplantation: the future?" *Langenbechs Arch. Surg.* 385: 378-8, 2000.

Bentley et al., "Successful cardiac transplantation with methanol or carbon monoxide-poisoned donors," *Thorac Surg* (2001), Apr.; 71(4):1194-7.

Brouard et al., "Carbon monoxide generated by heme oxygenase-1 suppresses endothelial cell apoptosis," *J Exp Med* (2000), Oct. 2; 192(7):1015-26.

Cantrell et al., "Low-Dose Carbon Monoxide Does Not Reduce Vasoconstriction in Isolated Rat Lungs," *Experimental Lung Research* 22:21-32, 1996.

Cardell et al., "Bronchodilation in vivo by carbon monoxide, a cyclic GMP related messenger," *British Journal of Pharmacology* 124:1065-1068, 1998.

(Continued)

*Primary Examiner*—Sandra E. Saucier
(74) *Attorney, Agent, or Firm*—Fish & Richardson P.C.

(57) ABSTRACT

The present invention features methods for transplanting organs, tissues and individual cells. Also featured are methods for maintaining cells in vitro and for enhancing survival and/or function of cells following transplantation. The methods include the administration of carbon monoxide in an amount sufficient to enhance cell survival and/or function.

54 Claims, 31 Drawing Sheets

OTHER PUBLICATIONS

Carlsson et al., "Measurement of Oxygen Tension in Native and Transplanted Rat Pancreatic Islets," *Diabetes* 47:1027-32, 1998.
Cecil Textbook of Medicine (21st Ed. 2000), vol. 1, pp. 273-279, 357-372, 387-419, 425-427, 436-448, 466-475, 507-512, 1060-1074.
Cecil Textbook of Medicine (21st Ed. 2000), vol. 2, pp. 1492-1499, 2042-2047, 2079-2081.
Choi et al., "Heme oxygenase-1: Function, regulation, and implication of a novel stress-inducible protein in oxidant-induced lung injury," *American Journal of Respiratory Cell and Molecular Biology* (1996), vol. 15, No. 1, 9-19.
Christodoulides et al., "Vascular Smooth Muscle Cell Heme Oxygenases Generate Guanylyl Cyclase-Stimulatory Carbon Monoxide," *Circulation* 97:2306-9, 1995.
Corbett et al., "Nitric oxide mediates cytokine-induced inhibition of insulin secretion by human islets of Langerhans," *Proc. Natl. Acad. Sci USA* 90:1731-5, 1993.
Friebe et al., "YC-1 Potentiates Nitric Oxide- and Carbon Monoxide-Induced Cyclic GMP Effects in Human Platelets," *Molecular Pharmacology* 54(6)962-967, 1998.
Gaine et al., "Introduction of heme oxygenase-1 with hemoglobin depresses vasoreactivity in rat aorta," *Vasc Res* (1999), Mar.-Apr.; 36(2):114-9.
Grau et al., "Effect of carbon monoxide breathing on hypoxia and radiation response in the SCCVII tumor in vivo," *Int J Radiat Oncol Biol Phys* (1994), Jun. 15; 29(3):449-54.
Grau et al., "Influence of Carboxyhemoglobin Level on Tumor Growth, Blood Flow, and Radiation Response in an Experimental Model," *Int. J. Radiation Oncology Biol. Phys.* 22:421-424, 1992.
Hantson et al., "Organ transplantation from victims of carbon monoxide poisoning," *Ann Emerg Med* (1996), May; 27(5):673-4.
Hebert et al., "Transplantation of kidneys from a donor with carbon monoxide poisoning," *New Engl J Med* (1992), Jun. 4; 326(23):1571.
Iberer et al., "Cardiac allograft harvesting after carbon monoxide poisoning. Report of a successful orthotopic heart transplantation," *J Heart Lung Transplant* (1993), May-Jun.; 12(3):499-500.
Kaufman et al., "Differential Roles of Mac-1$^+$ Cells, and CD4$^+$ and CD8$^+$ T Lymphocytes in Primary Nonfunction and Classic Rejection of Islet Allografts," *J Exp Med.* 772:291-302, 1990.
Koerner et al., "Extended donor criteria: use of cardiac allografts after carbon monoxide poisoning," *Transplantation* (1997), May 15; 63(9):1358-60.
Lacy et al., "Transplantation of Pancreatic Islets," *Annu. Rev. Immunol.,* 2:183-98, 1984.
Lefer et al., "A comparison of vascular biological actions of carbon-monoxide and nitric-oxide," *Methods and Findings in Experimental and Clinical Pharmacology* (1993), vol. 15, No. 9, 617-622.
Leikin et al., "The toxic patient as a potential organ donor," *Am J Emerg Med* (1994), Mar.; 12(2):151-4.
Mandrup-Poulsen et al., "Human Tumor Necrosis Factor Potentiates Human Interleukin 1-Mediated Rat Pancreatic β-Cell Cytotoxicity," *J. Immunol.* 739:4077-82, 1987.
Mansouri et al., "Alteration of Platelet Aggregation by Cigarette Smoke and Carbon Monoxide," *Thromb Haemost.* 48:286-8, 1982.
The Merck Manual (16th ed. 1992), pp. 646-657.
Nagata et al., "Destruction of Islet Isografts by Severe Nonspecific Inflammation," *Transplant Proc.* 22:855-6, 1990.
The New Encyclopedia Britannica (15th ed. 1994), vol. 26, *Macropaedia*, p. 756.
Otterbein et al., "Carbon Monoxide has Anti-Inflammatory Effects Involving the Mitogen-Activated Protein Kinase Pathway," *Nature Medicine* 6(4):1-7, 2000.
Otterbein et al., "Carbon Monoxide Provides Protection Against Hyperoxic Lung Injury," *The American Physiological Society*, L688-L694, 1999.
Petrache et al., "Heme oxygenase-1 inhibits TNF-α-induced apoptosis in cultured fibroblasts," *Am. J. Physiol. Lung Cell Mol. Physiol.* 287: L312-L319, 2000.
Pozzoli et al., "Carbon Monoxide as a Novel Neuroendocrine Modulator: Inhibition of Stimulated Corticotropin-Releasing Hormone Release from Acute Rat Hypothalamic Explants," *Endocrinology* 735:2314-2317, 1994.
Rabinovitch et al., "Transfection of Human Pancreatic Islets With an Anti-Apoptotic Gene (*bcl-2*) Protects β-Cells From Cytokine-Induced Destruction," *Diabetes* 48:1223-9, 1999.
Ringel et al., "Carbon Monoxide-induced Parkinsonism," *J. Neurol. Sci.,* 1972, 16:245-251.
Roberts et al., "Successful heart transplantation from a victim of carbon monoxide poisoning," *Ann Emerg Med* (1995), Nov.; 26(5):652-5.
Sato et al., "Carbon monoxide generated by heme oxygenase-1 suppresses the rejection of mouse to rat cardiac transplants," *J. Immunol.* 166: 4185-4194 (2001).
Schipper et al., "Expression of heme oxygenase-1 in the senescent and Alzheimer-diseased brain," *Annals of Neurology* (1995), vol. 37, No. 6, 758-768.
Shapiro et al., "Islet Transplantation in Seven Patients with Type 1 Diabetes Mellitus Using a Glucocorticoid-Free Immunosuppressive Regimen," *N Engl. J. Med.,* 343:230-8, 2000.
Shennib et al., "Successful transplantation of a lung allograft from a carbon monoxide-poisoning victim," *Heart Lung Transplant* (1992), Jan.-Feb.; 11(1 Pt 1): 68-71.
Siow et al., "Heme oxygenase-carbon monoxide signaling pathway in atherosclerosis: anti-atherogenic actions of bilirubin and carbon monoxide?" *Cardiovascular Research* 41:385-394, 1999.
Smith et al., "Successful heart transplantation with cardiac allografts exposed to carbon monoxide poisoning," *Heart Lung Transplant* (1992), Jul.-Aug.; 11(4 Pt. 1):698-700.
Soares et al., "Expression of heme oxygenase-1 can determine cardiac xenograft survival," *Nat Med.* 4:1073-1077, 1998.
Stephens, "Further Observations regarding Carbon Monoxide Gas as an Important Factor in the Causation of Industrial Cancer," *The Medical Press and Circular*, vol. CXXXVI, No. 4924, 283-288 (1933).
Tenderich et al., "Hemodynamic follow-up of cardiac allografts from poisoned donors," *Transplantation* (1998), Nov. 15; 66(9): 1163-7.
Tenhunen et al., "The Enzymatic Conversion of Heme to Bilirubin by Microsomal Heme Oxygenase," *Proc Natl Acad Sci USA* 61:748-755, 1968.
Utz et al., "Carbon Monoxide Relaxes Ileal Smooth Muscle Through Activation of Guanylate Cyclase," *Biochem Pharmacol.* 47:195-201, 1991.
Vassalli et al., "Inhibition of hypoxic pulmonary vasoconstriction by carbon monoxide in dogs," *Eur. Resp. J.* (1998), 12, Suppl. 28, 237s.
Verma et al., "Carbon Monoxide: A Putative Neural Messenger," *Science* 259:381-384, 1993.
Verran et al., "Use of liver allografts from carbon monoxide poisoned cadaveric donors," *Transplantation* (1996), Nov. 27; 62(10):1514-5.
Weir et al., "Scientific and Political Impediments to Successful Islet Transplantation," *Diabetes* 46:1247-56, 1997.
Weir et al., "Islet Transplantation as a treatment for diabetes," *J. Am. Optom. Assoc.* 69:727-32, 2000.
Yuan et al., "Evidence of increased endogenous carbon monoxide production in newborn rat endotoxicosis," *Chinese Medical Sciences Journal* (1997), vol. 12, No. 4, 212-215.
Brown et al., "In vivo binding of carbon monoxide to cytochrome *c* oxidase in rat brain", American Physiological Society, pp. 604-610 (1990).
Campbell, "Living At Very High Altitudes", *The Lancet* 1:370-373 (1930).
Campbell, "The Effect of Carbon Monoxide and Other Agents Upon the Rate of Tumour Growth", J Pathology & Bacteriology 35:379-394 (1932).
Campell, "Cancer of Skin and Increase in Incidence of Primary Tumours of Lung in Mice Exposed to Dust Obtained from Tarred Roads", *Brit. J Exper. Pathol.* XV(5):24, 289-294 (1934).
Chapman et al., "Exogenous Carbon Monoxide Attenuates Aeroallergen-induced Eosinophilic Inflammation in Mice", *J Respiratory Critical Care Med* 159(3):A218 (1999).

Chapman et al., "Carbon Monoxide Attenuates Aeroallergen-induced Inflammation in Mice", *Am. J. Physiol. Lung Cell Mol Physiol.* 281:L209-L216 (2001).
Davidson et al., "Inflammatory Modulation and Wound Repair" *J Investigative Dermatology* xi-xii (2003).
Dioum et al., "NPAS2: A Gas-Responsive Transaction Factor", Sciencexpress/www.sciencexpress.org/Nov. 21, 2002/pp. 1-6/10.1126/science.1078456.
Donnelly et al., "Expression of Heme-Oxygenase in Human Airway Primary Epithelial Cells", *J Respiratory Critical Care Med* 159(3):A218 (1999).
Katori et al., "Heme Oxygenase-1 System in Organ Transplantation", *Transplantation* 74(7):905-912 (2002).
Maxwell et al., "Studies in Cancer Chemotherapy: XI. The Effect of CO, HCN, and Pituitrin Upon Tumor Growth", Dept. of Cancer Research, Santa Barbara Cottage Hospital, pp. 270-282 (Jan. 30, 1933).
Meilin et al., Effects of carbon monoxide on the brain may be mediated by nitric oxide, *J Appl Physiol.* 81(3):1078-83 (1996).
Minamino et al., "Targeted expression of heme oxygenase-1 prevents the pulmonary inflammatory and vascular responses to hypoxia", *PNAS* 98(15):8798-8803 (2001).
Myers, "Cirrhotic cardiomyopathy and liver transplantation," *Liver Transpl* 6(4 Suppl 1):S44-52 (2000).
Otterbein et al., "Mechanism of hemoglobin-induced protection against endotoxemia in rats: a ferritin-independent pathway", *Am J Physiol Lung Cell Mol Physiol* 272:L268-275 (1997).
Otterbein et al., "Carbon monoxide provides protection against hyperoxic lung injury in rats", *J Respiratory Critical Care Med* 159(3):A218 (1999).
Paredi et al., "Increased Carbon Monoxide in Exhaled Air of Cystic Fibrosis Patients", *J Respiratory Critical Care Med* 159(3):A218 (1999).
Piantadosi et al., "Production of Hydroxyl Radical in the Hippocampus After CO Hypoxia Hypoxia in the Rat", *Free Radical Biol. & Med.* 22(4):725-732 (1997).
Singhal et al., "Effects of Normobaric Hyperoxia in a Rat Model of Focal Cerebral Ischemia-Reperfusion", *J Cerebral Blood Flow & Medicine* 22:861-868 (2002).
Tamayo et al., "Carbon monoxide inhibits hypoxic pulmonary vasoconstriction in rats by a cGMP-independent mechanism", *Pflugers Arch.* 434(6):698-704 (1997).
Taylor, "Anti-TNF Therapy for Rheumatoid Arthritis and Other Inflammatory Diseases", *Molecular Biotechnology* 19:153-168 (2001).
Tulis et al., "Adenovirus-Mediated Heme Oxygenase-1 Gene Delivery Inhibits Injury-Induced Vascular Neointima Formation", *Circulation* 104:2710-2715 (2001).
Wang et al., "Resurgence of carbon monoxide: an endogenous gaseous vasorelaxing factor", *Can. J. Physiol. Pharmacol.* 76:1-15 (1998).
Welty et al., "Hyperoxic Lung Injury is Potentiated by SPC-Promotor Driven Expression of an HO-1 Transgene in Mice", *J Respiratory Critical Care Med* 159(3):A218 (1999).
Weng et al., "Transpulmonary HO-1 Gene Delivery in Neonatal Mice", *J Respiratory Critical Care Med* 159(3):A218 (1999).
Carraway et al., "Induction of ferritin and heme oxygenase-1 by endotoxin in the lung," Am. J. Physiol. Lung Cell. Mol. Physiol. 275:L583-92 (1998).
Choi, "Heme Oxygenase-1 Protects the Heart," Circulation Research 89:105-7 (2001).
Clayton et al., "Inhaled carbon monoxide and hyperoxic lung injury in rats," Am. J. Physiol. Lung Cell Mol. Physiol. 281:L949-57 (2001).
Fujita et al., "Paradoxical rescue from ischemic lung injury by inhaled carbon monoxide driven by derepression of fibrinolysis," Nature Medicine 7:598-604 (2001).
Hayes et al., "A Review of Modern Concepts of Healing of Cutaneous Wounds," J. Dermatol. Surg. Oncol. 3(2):188-93 (1977).
Kyokane et al., "Carbon Monoxide From Heme Catabolism Protects Against Hepatobiliary Dysfunction in Endotoxin-Treated Rat Liver," Gastroenterology 120:1227-40 (2001).
Lee et al., "Intestinal Motility and Absorption in Acute Carbon Monoxide Poisoning," Seoul J. Med. 15:95-105 (1974) (English translation provided).
Lee et al., "Regulation of Heme Oxygenase-1 Expression In Vivo and In Vitro in Hyperoxic Lung Injury", Am. J. Respir. Cell Biol. 14:556-568 (1996).
Liu et al., "Carbon monoxide and nitric oxide suppress the hypoxic induction of vascular endothelial growth factor gene via the 5' enhancer," J. Biol. Chem. 273(24):15257-62 (1998).
Nachar at al., "Low-Dose Inhaled Carbon Monoxide Reduces Pulmonary Vascular Resistance During Acute Hypoxemia in Adult Sheep," High Altitude Medicine & Biology 2:377-385 (2001).
Nakao et al., "Immunomodulatory effects of inhaled carbon monoxide on rat syngeneic small bowel graft motility," Gut 52: 1278-85 (2003).
Pannen et al., "Protective Role of Endogenous Carbon Monoxide in Hepatic Microcirculatory Dysfunction after Hemorrhagic Shock in Rats," J. Clin. Invest. 102:1220-1228 (1998).
Peek et al., "Extracorporeal Membrane Oxygenation for Adult Respiratory Failure," Chest 112(3)759-64 (1997).
Ringel et al., "Carbon Monoxide-induced Parkinsonism", J. neurol. Sci. 16:245-251 (1972).
Zuckerbraun et al., "Carbon monoxide attenuated the development of necrotizing enterocolitis in an animal model," Surgical Infection Society 3:83 (2002).
Sato et al., "Carbon monoxide can fully substitute Herne Oxygenase-1 in suppressing the rejection of mouse to rat cardiac transplants," Acta Haematologica, 103 (Suppl. 1):87, Abstract 348 (2000).
Sato et al., "Herne oxygenase-1 or carbon monoxide prevents the inflammatory response associated with xenograft rejection," Acta Haematologica, 103(Suppl. 1):87, Abstract 345 (2000).
Toda et al., "Exogenous carbon monoxide protects endothelial cells against oxidant stress and improves graft function after lung transplantation," Circulation, 98(17):I265 (1998).
Bach, "Heme oxygenase-1 as a protective gene," Wien. Klin. Wochenschr. 114(Suppl):4:1-3 (2002).
Billiar, "The diverging roles of carbon monoxide and nitric oxide in resuscitated hemorrhagic shock," Crit. Care Med. 27:2842-3 (1999).
Bracho et al., "Carbon Monoxide Protects against Organ Injury in Hemorrhagic Shock/Resuscitation," Journal of Surgical Research, 107:270, (2002), Abstract.
Brouard et al., "Carbon monoxide generated by Heme Oxygenase-1 (HO-1) suppresses endothelial cell apoptosis via activation of the p38 mitogen activated protein kinase (MAPK) pathway," Acta Haematologica 103(Suppl 1):64, (2000), Abstract.
Brouard et al., "Heme oxygenase-1-derived carbon monoxide requires the activation of transcription factor NF-kappa B to protect endothelial cells from tumor necrosis factor-alpha-mediated apoptosis," J. Biol. Chem., 277(20):17950-17961, (2002).
Brouard et al., "Molecular mechanism underlying the anti-apoptotic effect of Heme oxygenase-1 derived carbon monoxide," Xenotransplantation, 8(Suppl 1): p22 (2001).
Calabrese et al., "Carbon Monoxide (CO) Prevents Apoptotic Events Related to Ischemia/Reperfusion (IR) Injury in an hDAF Pig-to Primate Xenotransplantion Model," Xenotransplantation 10:488, (2003), Abstract.
Carbon Monoxide Poisoning - Symptoms; http://my.webmd.com/hw/home_health/aa7304.asp;retrieved Jul. 11, 2005.
Carbon Monoxide Poisoning - What Happens; http://my.webmd.com/hw/home_health/aa7326.aps;retrieved Jul. 11, 2005.
Chapman and Choi, "Exhaled monoxides as a pulmonary function test: use of exhaled nitric oxide. and carbon monoxide," Clin. Chest Med. 22:817-836 (2001).
Chin et al., "Transcriptional regulation of the HO-1 gene in cultured macrophages exposed to model airborne particulate matter," Am. J. Physiol. Lung Cell. Mol. Physiol., 284(3):L473-L480, (2003).
Choi and Otterbein, "Emerging role of carbon monoxide in physiologic and pathophysiologic states," Antioxid. Redox Signal. 4:227-228 (2002).
Cozzi et al., "Donor Preconditioning with Carbon Monoxide (CO) in Pig-to-Primate Xenotransplantation," Xenotransplantation 10:528, (2003), Abstract.

Crapo et al., "Single-breath carbon monoxide diffusing capacity," Clin. Chest Med., 22:637-649, (2001).
Deng et al., "Carbon Monoxide Potentiates Cerulein-Induced Pancreatitis in Chronic Alcohol-Fed Rats," Gastroenterology, 124(4):A618-19, (2003), Abstract.
Dyck et al., "Carbon Monoxide (CO) Attenuates Lipopolysaccharide (LPS)-Induced Cytokine Expression of IL-6," Acta Haematologica 103(Suppl 1):64, (2000), Abstract.
Farrugia and Szurszewski, "Heme oxygenase, carbon monoxide, and interstitial cells of Cajal," Microsc. Res. Tech. 47:321-4, (1999).
Günther et al., "Carbon monoxide protects pancreatic beta-cells from apoptosis and improves islet function/survival after transplantation," Diabetes, 51(4):994-999, (2002).
Hartsfield and Choi, "Mitogen activated protein kinase (MAPK) is modulated by both endogenous and exogenous carbon monoxide," FASEB Journal 12:A187, 1088, (1998), Abstract.
Hartsfield et al., "Differential signaling pathways of HO-1 gene expression in pulmonary and systemic vascular cells," Am. J. Physiol., 277(6 Pt 1):L1133-L1141, (1999).
Hartsfield et al., "Regulation of heme oxygenase-1 gene expression in vascular smooth muscle cells by nitric oxide," Am. J. Physiol., 273(5Pt 1):L980-988, (1997).
Hartsfield, "Targeted Overexpression of Heme Oxygenase-1 (HO-1) Attenuates Hypoxia-Induced Right Ventricular Hypertrophy," FASEB Journal 13:A827, (1999), Abstract.
Horvath et al., "Haemoxygenase-1 induction and exhaled markers of oxidative stress in lung diseases', summary of the ERS Research Seminar in Budapest, Hungary, Sep. 1999," Eur. Respir. J., 18(2):420-430, (2001).
Huizinga Jan D., "Physiology and Pathophysiology of the Interstitial Cell of Cajal: From Bench to Bedside: II. Gastric motility: lessons from mutant mice on slow waves and innervation," Am. J. Physiol. 281:1129-1134, (2001).
Kozma et al., "Role of carbon monoxide in heme-induced vasodilation," Eur. J. Pharmacol., 323:R1-2 (1997).
Moore et al., "Carbon Monoxide Protects against Intestinal Dysmotility Associated with Small Bowel Transplantation," Gastroenterology 122:A38, (2002), Abstract.
Moore et al., "Carbon Monoxide Suppresses the Development of Ileus Associated with Surgical Manipulation of the Small Intestine," Gastroenterology 122:A61-A62, (2002), Abstract.
Moore et al., "Pre-treatment with Low Concentration of Carbon Monoxide (250 to 75 ppm) for 3 hr prior to Laparotomy Protects Against Postoperative Ileus," Digestive Disease Week Abstracts and Intinerary Planner 2003: Abstract No. M1337 (2003).
Morse et al., "Carbon monoxide-dependent signaling," Crit. Care Med., 30:S12-S17, (2001).
Morse et al., "Suppression of inflammatory cytokine production by carbon monoxide involves the JNK pathway and AP-1," J. Biol. Chem., 278(39):36993-36998, (2003).
Nakao et al., "Protective effect of carbon monoxide inhalation for cold-preserved small intestinal grafts," Surgery, 134:285-92, (2003).
Ning et al., "TGF-betal stimulates HO-1 via the p38 mitogen-activated protein kinase in A549 pulmonary epithelial cells,", Am. J. Physiol. Lung Cell. Mol. Physiol., 283(5):L1094-L1102, (2002).
Otterbein et al., "Carbon Monoxide suppresses arteriosclerotic lesions associated with chronic graft rejection and with balloon injury," Nature Medicine 9:183-90 (2003).
Otterbein et al., "Carbon monoxide at low concentrations induces growth arrest and modulates tumor growth in mice," Exp. Biol. Med., 228(5):633, (2003), Abstract.
Otterbein et al., "Carbon Monoxide Inhibits TNFα-Induced Apoptosis and Cell Growth in Mouse Fibroblasts," American Journal of Respiratory and Critical Care Medicine 159(3 Suppl.):A285 (1999).
Otterbein et al., "Carbon Monoxide Modulates Lipolysaccaride (LPS)-Induced Inflammatory Responses in vivo and in vitro," American Journal of Respiratory and Critical Care Medicine 159(3 Suppl.):A481 (1999).
Otterbein et al., "Carbon Monoxide, A Gaseous Molecule with Anti-Inflammatory Properties," pp. 133-156 in *Disease Markers in Exhaled Breath*, Marczin et al., eds., Marcel Dekker, Inc., New York, (2003).
Otterbein et al., "Carbon Monoxide Mediates Anti-Inflammatory Effects Via the P38 Mitogen Activated Protein Kinase Pathway," Acta Haematologica 103:64, (2000), Abstract.
Otterbein et al., "Carbon Monoxide Protects Against Oxidant-Induced Lung Injury in Mice Via the p38 Mitogen Activated Protein Kinase Pathway," Acta Haematologica 103:83, (2000), Abstract.
Otterbein et al., "Exogenous administration of heme oxygenase-1 by gene transfer provides protection against hyperoxia-induced lung injury," J. Clin. Invest., 103(7):1047-1054, (1999).
Otterbein et al., "Heme oxygenase: colors of defense against cellular stress," Am. J. Physiol. Lung Cell Mol. Physiol., 279(6):L1029-L1037, (2000).
Otterbein et al., "Protective effects of heme oxygenase-1 in acute lung injury," Chest. 116:61S-63S, (1999).
Otterbein, "Anti-Inflammatory Effects of Carbon Monoxide in the Lung," CRISP Data Base National Institute of Health; Doc. No. CRISP/2003HL071797-01A1, (2003).
Otterbein, "Carbon monoxide: innovative anti-inflammatory properties of an age-old gas molecule," Antioxid. Redox Signal., 4:309-319, (2002).
Pileggi et al., "Heme oxygenase-1 induction in islet cells results in protection from apoptosis and improved in vivo function after transplantation," Diabetes, 50(9):1983-1991, (2001).
Ryter and Choi, "Heme Oxygenase-1: Molecular Mechanisms of Gene Expression in Oxygen-Related Stress," Antioxid. Redox Signal. 4:625-632, (2002).
Ryter et al., "Heme oxygenase/carbon monoxide signaling pathways: Regulation and functional significance," Mol. Cell. Biochem., 234-235(1-2):249-263, (2002).
Ryter et al., "Mitogen Activated Protein Kinase (MAPK) Pathway Regulates Heme Oxygenase-1 Gene Expresssion by Hypoxia in Vascular Cells," Exp. Biol. Med., 225(5):607, (2003), Abstract.
Sarady et al., "Carbon monoxide modulates endotoxin-induced production of granulocyte macrophage colony-stimulating factor in macrophages," Am. J. Respir. Cell. Mol. Biol., 27(6):739-745, (2002).
Sarady et al., "Cytoprotection by heme oxygenase/CO in the lung," in *Disease Markers in Exhaled Breath*, Marczin and Yacoub, eds., IOS Press, 346:73-78, (2002).
Sasidhar et al., "Exogenous Carbon Monoxide Attentuates Mitogen Activated Protein Kinase (MAPK) Activation in Rat Pulmonary Artery Endothelial Cells Exposed to Hypoxia," American Journal of Respiratory and Critical Care Medicine. 1999;159(3 Suppl.):A352.
Sass et al., "Heme Oxygenase-1 Induction Prevents Apoptotic Liver Damage in Mice," Naunyn-Schmiedelberg's Archives of Pharmacology 367:R78, (2003).
Sethi et al, "Differential modulation by exogenous carbon monoxide of TNF-alpha stimulated mitogen-activated protein kinases in rat pulmonary artery endothelial cells," Antioxid. Redox Signal., 4:241-8, (2002).
Sethi et al., "Differential Effects of Exogenous Carbon Monoxide on TNF-α-Induced Mitogen Activated Protein (MAP) Kinase Signaling Pathway in Rat Pulmonary Artery Endothelial Cells," American Journal of Respiratory and Critical Care Medicine 159(3 Suppl. ):A350 (1999).
Seyfried et al., "HO-1 induction protects mice from Immune-mediated liver injury," Naunyn-Schmiedeberg's Archives of Pharmacology 367:R80 (2003).
Slebos et al., "Heme oxygenase-1 and carbon monoxide in pulmonary medicine," Respir Res. 4(7):1-13, (2003).
Soares et al., "Heme oxygenase-1, a protective gene that prevents the rejection of transplanted organs," Immunol. Rev. 184:275-285, (2001).
Soares et al., "Modulation of endothelial cell apoptosis by heme oxygenase-1-derived carbon monoxide," Antioxid. Redox Signal., 4:321-329, (2002).
Soares et al., "Heme Oxygenase-1 and/or Carbon Monoxide can Promote Organ Graft Survival," in *Disease Markers in Exhaled Breath*, Marczin and Yacoub, eds., IOS Press, 346:267-273, (2002).

Song et al., "Carbon monoxide induces cytoprotection in rat orthotopic lung transplantation via anti-inflammatory and anti-apoptotic effects," Am. J. Pathol., 163(1):231-242, (2003).
Song et al., "Carbon monoxide inhibits human airway smooth muscle cell proliferation via mitogen-activated protein kinase pathway," Am. J. Respir. Cell. Mol. Biol. 27(5):603-610, (2002).
Song et al., "Regulation of IL-1beta-induced GM-CSF production in human airway smooth muscle cells by carbon monoxide," Am. J. Physiol. Lung Cell. Mol. Physiol., 284(1):L50-L56, (2003).
Stupfel and Bouley, "Physiological and Biochemical Effects on Rats and Mice Exposed to Small Concentrations of Carbon Monoxide for Long Periods," Ann. N.Y. Acad. Sci. 174:343-368 (1970).
Tobiasch et al., "Heme oxygenase-1 protects pancreatic β cells from apoptosis caused by various stimuli," J. Investig. Med., 49:566-71, (2001).
Yamashita et al., "Effects of HO-1 induction and carbon monoxide on cardiac transplantation in mice," Exp. Biol. Med., 228(5):616, (2003), Abstract.
Zhang et al., "Carbon monoxide inhibition of apoptosis during ischemia-reperfusion lung injury is dependent on the p38 mitogen-activated protein kinase pathway and involves caspase 3," J. Biol. Chem., 278:(2):1248-1258, (2003).
Zhang et al., "Mitogen-activated protein kinases regulate HO-1 gene transcription after ischemia-reperfusion lung injury," Am. J. Physiol. Lung Cell. Mol. Physiol., 283(4):L815-L829, (2002).
Zhou et al., "Endogenous carbon monoxide and acute lung injury," Section of Respiratory System Foreign Medical Sciences 19:185-187 (1999) (translation included).
Zuckerbraun and Billiar, "Heme oxygenase-1: a cellular Hercules" Hepatology, 37(4):742-744, (2003).
Zuckerbraun et al., "Carbon monoxide inhibits intestinal inducible nitric oxide synthase production and ameliorates intestinal inflammation in experimental NEC," J. Amer. College of Surgeons 197:S50 (2003).
Zuckerbraun et al., "Carbon Monoxide Protects Hepatocytes from TNF-alpha/Actinomycin D Induced Cell Death," Critical Care Medicine 29:A59 (2001).
Choi et al., "Therapeutic carbon monoxide may be a reality soon," Am. J. Respir. Crit. Care Med., 171(11):1318-1319, (2005).
Dolinay et al., "Can Inhalation Carbon Monoxide be utilized as a therapeutic modality in human disease?", pp. 203-206 in *Breath Analysis for Clinical Diagnosis and Therapeutic Monitoring*, Amann and Smith, eds., World Scientific Publishing Company (2004).
Dolinay et al., "Inhaled carbon monoxide confers antiinflammatory effects against ventilator-induced lung injury," Am. J. Respir. Crit. Care Med. 170:613-620 (2004).
Mayr et al., "Effects of carbon monoxide inhalation during experimental endotoxemia in humans," Am. J. Respir. Crit. Care Med., 171:354-360, (2005).
Ryter et al., "Therapeutic applications of carbon monoxide in lung disease," Curr. Opin Pharmacol., 6:257-262, (2006).
Ryter et al., "Heme oxygenase-1/carbon monoxide: from basic science to therapeutic applications," Physiol. Rev. 86(2):583-650 (2006).
Thom et al, "Therapeutic' Carbon Monoxide May Be Toxic," Am. J. Respir. Crit. Care Med., 171(11):1318, (2005).
Favory et al., "Myocardial Dysfunction and Potential Cardiac Hypoxia in Rats Induced by Carbon Monoxide Inhalation," Am. J. Respir. Crit. Care Med. 174:320-325 (2006).
Mazzola et al., "Carbon monoxide pretreatment prevents respiratory derangement and ameliorates hyperacute endotoxic shock in pigs," FASEB J. 19:2045-2047 (2005).
American Thoracic Society, "Single breath carbon monoxide diffusing capacity (transfer factor): recommendations for a standard technique," Am. Rev. Respir. Dis. 136: 1299-1307 (1987).
American Thoracic Society, "Single breath carbon monoxide diffusing capacity (transfer factor): recommendations for a standard technique-1995 update," Am. J. Respir. Crit. Care. Med. 152: 2185-2198 (1995).
Arcasoy et al., "Erythropoietin (EPO) Stimulates Angiogenesis In Vivo and Promotes Wound Healing," Blood 98: 822A-823A, Abstract (2001).
Caplan et al., "Role of asphyxia and feeding in a neonatal rat model of necrotizing enterocolitis," Pediatr. Pathol., 14: 1017-1028 (1994).
Czlonkowska et al., "Immune processes in the pathogenesis of Parkinson's disease - a potential role for microglia and nitric oxide," Med. Sci. Monit. 8:RA165-RA177 (2002).
Goldberg and Schneider, "Similarities between the oxygen-sensing mechanisms regulating the expression of vascular endothelial growth factor and erythropoietin," J. Biol. Chem. 269: 4355-359 (1994).
Guo, "The Research Status of the Gas Messanger Molecules of Nitric Oxide and Carbon Monoxide in the Biomedicine Field," Practical Journal of Cardiac, Cerebral and Pulmonary Vascular Diseases vol. 8(2) (2000) (English translation included).
Harmey and Bouchier-Hayes, "Vascular endothelial growth factor (VEGF), a survival factor for tumour cells: implications for anti-angiogenic therapy," Bioessays 24: 280-83 (2003).
Josko, "Vascular endothelial growth factor (VEGF) and its effect on angiogenesis," Medical Science Monitor 6: 1047-52 (2000).
Krause et al., "Recombinant human erythropoietin and VEGF have equal angiogenic potency: Investigation in a novel in vitro assay of human vascular tissues," European Heart J. 22: 154 Abstract (2001).
Omaye, "Metabolic modulation of carbon monoxide toxicity," Toxicol. 180:139-150 (2002).
Potter et al., "The inflammation-induced pathological chaperones ACT and apo-E are necessary catalysts of Alzheimer amyloid formation," Neurobiology of Aging 22:923-30 (2001).
Shahin et al., "Carboxyhemoglobin in pediatric sepsis and the systematic inflammatory response syndrone," Clinical Intensive Care 11(6): 311-17 (2000).
Stewart, "The effect of carbon monoxide on humans," J. Occup. Med. 18: 304-309 (1976).
Stewart, "The effects of low concentrations of carbon monoxide in man," Scand. J. redpir. Dis. Suppl. 91: 56-62 (1974).
Thiemermann "Inhaled Co: deadline gas or novel therapeutic?" Nature Medicine 7(5): 534-35 (2001).
Vreman et al., "Carbon monoxide and carboxyhemoglobin," Adv. Pediatr. 42: 303-34 (1995).
Wright and Shephard, "Physiological effects of carbon monoxide," Int. Rev. Physiol. 20: 311-68 (1979).
Zegdi et al., "Increased endogenous CO production in severe sepsis," Intensive Care Medicine 23: 793-96 (2002).
Zuckerbraun et al., "Carbon Monoxide protects against Liver Failure through Nitric Oxide-induced Heme Oxygenase 1," J. Exp. Med. 198: 1707-716 (2003).

* cited by examiner

| | | | | | |
|---|---|---|---|---|---|
| HO-1 | − | + | + | + | + |
| SnPPIX | − | − | + | + | + |
| CO (ppm) | − | − | − | 250 | $10^4$ |

CARBON MONOXIDE IMPROVES OUTCOMES IN TISSUE AND ORGAN TRANSPLANTS AND SUPPRESSES APOPTOSIS

This application claims priority to U.S. Provisional Application Nos. 60/300,289, filed Jun. 21, 2001; 60/334,340, filed Nov. 29, 2001; and 60/337,974, filed Dec. 7, 2001.

STATEMENT AS TO FEDERALLY SPONSORED RESEARCH

This invention was made with Government support under National Institutes of Health Grant Nos. HL 58688. The Government has certain rights in this invention.

TECHNICAL FIELD

This invention relates to the field of enhancing cell survival.

BACKGROUND

Carbon monoxide (CO) gas is poisonous in high concentrations. However, it is now recognized as an important signaling molecule (Verma et al., Science 259:381–384, 1993). It has also been suggested that carbon monoxide acts as a neuronal messenger molecule in the brain (Id.) and as a neuro-endocrine modulator in the hypothalamus (Pozzoli et al., Endocrinology 735:2314–2317, 1994). Like nitric oxide (NO), carbon monoxide is a smooth muscle relaxant (Utz et al., Biochem Pharmacol. 47:195–201, 1991; Christodoulides et al., Circulation 97:2306–9, 1995) and inhibits platelet aggregation (Mansouri et al., Thromb Haemost. 48:286–8, 1982). Inhalation of low levels of CO has been shown to have anti-inflammatory effects in some models.

Islet cell transplantation is a viable treatment for the amelioration of type I diabetes (Lacy et al., Annu. Rev. Immunol., 2:183–98, 1984; Weir et al., J. Am. Optom. Assoc. 69:727–32, 2000; Berney et al., Langenbechs Arch. Surg. 385: 378–8, 2000; Shapiro et al., N Engl. J. Med., 343:230–8, 2000). However, the processes of clinical islet transplantation are made difficult by a number of factors. One factor is primary nonfunction (PNF) of the graft. Another is the need for high numbers of donor islets needed for a successful reversal of diabetes (Shapiro et al., N Engl. J. Med., 343:230–8, 2000). Both situations reflect the same pathophysiology: the substantial cell loss in the graft within the first weeks after transplantation. After transplantation, islets suffer a variety of stress factors such as hypoxia before secondary vascularization (Carlsson et al., Diabetes 47:1027–32, 1998) and exposure to pro-inflammatory cytokines and free radicals released from macrophages in the microenvironment of the transplant (Rabinovitch et al., Diabetes 48:1223–9, 1999; Kaufman et al., J Exp Med. 772:291–302, 1990; Corbett et al., Proc. Natl. Acad. Sci USA 90:1731–5, 1993) and from resident islet macrophages (Mandrup-Poulsen et al., J. Immunol. 739:4077–82, 1987; Arnush et al., J. Clin Invest. 702:516–26, 1998). The toxic effects of immunosuppressive drugs as well as rejection (Weir et al., Diabetes 46:1247–56, 1997) also contribute to islet cell loss. The existence of PNF after experimental syngeneic islet transplantation (Nagata et al., Transplant Proc. 22:855–6, 1990; Arita et al., Transplantation 65:1429–33, 1998) indicates that non-specific inflammation plays a major role in this scenario.

Survival of a transplanted organ is thought to relate mainly to the success of immunosuppression, in terms of blocking the immune response that leads to graft rejection. However, it has previously been shown that transplanted organs can protect themselves from vascular injury leading to rejection through the expression of“protective genes” (see, e.g., Bach et al., Nature Med. 3:196–202 (1997); and Soares et al., Nat Med. 4:1073–1077, 1998). One such gene, heme oxygenase-1 (HO-1) catabolizes heme into biliverdin, free iron and CO (Tenhunen et al., Proc Natl Acad Sci USA 61:748–755, 1968).

Endothelial cells (ECs) lining blood vessels maintain blood flow, allowing the continuous traffic of plasma and cellular constituents between blood and parenchymal tissues. To accomplish this function, ECs must promote a certain level of vasorelaxation and inhibit leukocyte adhesion as well as coagulation and thrombosis. However, when ECs are exposed to proinflammatory stimuli, they become “activated” and promote vasoconstriction, leukocyte adhesion and activation, and coagulation and thrombosis. These functional changes are due to the expression by activated ECs of a series of proinflammatory genes encoding adhesion molecules, cytokines/chemokines, and costimulatory and procoagulant molecules. Unfettered EC activation, as during acute and chronic inflammation, can lead to EC injury and apoptosis. EC apoptosis is a prominent feature associated with acute and/or chronic inflammation such as it occurs during hyperoxia, endotoxic shock, arteriosclerosis, ischemia reperfusion injury, and acute or chronic graft rejection.

SUMMARY

The present invention is based, in part, on the observations that CO promotes the survival and/or function of organ, tissue, and individual cell transplants.

Accordingly, in one aspect, the present invention provides a method of administering to a transplant donor a pharmaceutical composition containing carbon monoxide, obtaining an organ, tissue or cells from the donor, and transplanting the organ, tissue or cells into a recipient, where the amount of carbon monoxide administered to the donor is sufficient to enhance survival or function of the organ or tissue after transplantation into the recipient.

The pharmaceutical composition can be administered to a live donor, to a brain-dead donor, or to the donor prior to and following brain death.

Optionally, the organ can be treated in situ in the donor and/or ex vivo with a pharmaceutical composition comprising carbon monoxide.

The method can also or alternatively include the step of administering to the recipient a second pharmaceutical composition that includes carbon monoxide, before and/or during and/or after the step of transplanting the organ or tissue into the recipient.

In this or any of the methods described herein, the organ or tissue can be any organ which can be transplanted, e.g., a liver, a kidney, a heart, a pancreas, a lung, small intestine, and/or skin, and the donor can be of a species different from that of the recipient, or the donor and the recipient can be of the same species. The donor and the recipient can both be non-human animals or humans. Alternatively, the donor can be a non-human animal such as pig, and the recipient can be a human.

In another aspect, the invention provides a method of transplanting an organ, tissue or cells which includes providing an organ, tissue or cells of a donor, administering ex vivo or in situ to the organ, tissue or cells a pharmaceutical composition that includes carbon monoxide, and transplanting the organ or tissue into a recipient, wherein the amount of carbon monoxide is sufficient to enhance survival or function of the organ, tissue or cells in the recipient. In one embodiment, the pharmaceutical composition is administered by perfusing the organ or tissue in situ while the organ or tissue is in the donor.

Optionally, the method can include the step of administering to the recipient a second pharmaceutical composition containing carbon monoxide before and/or during and/or after transplantation of the organ or tissue into the recipient.

In yet another aspect, the invention provides a method of transplanting an organ, tissue or cells that includes the steps of providing an organ, tissue or cells of a donor, transplanting the organ, tissue or cells into a recipient, and before, and/or during, and/or after the step of transplanting the organ, tissue or cells into the recipient, administering to the recipient an amount of a pharmaceutical composition containing carbon monoxide sufficient to enhance survival and/or function of the transplanted organ, tissue or cells in the recipient.

In one embodiment, the pharmaceutical composition can be administered to the recipient within 0 to 20 days, e.g., within 1, 2, 4, 6, 8, 10, 12, 14, 18, or 20 days, after the organ has been transplanted into the recipient. In another embodiment, the pharmaceutical composition is administered to the recipient at least once, e.g., multiple times or continuously, from the time beginning 21 days after the step of transplanting the organ or tissue into the recipient for as long as needed to ensure survival of the graft. The pharmaceutical composition can be administered to the recipient upon determination that the transplanted organ or tissue is undergoing or about to undergo rejection, e.g., chronic rejection or acute rejection.

Optionally, the method can further include the step of administering to the donor a second pharmaceutical composition containing carbon monoxide prior to obtaining the organ or tissue from the donor. The second pharmaceutical composition can be administered to a live donor or to a brain-dead donor.

The method can include the step of administering to the organ a second pharmaceutical composition containing carbon monoxide in situ in the donor and/or ex vivo.

In another aspect, the invention provides a method of enhancing the survival and/or function of a donor organ, tissue or cell which includes providing an organ, tissue or cell of a marginal donor and exposing the organ, tissue or cell to an amount of a pharmaceutical composition containing carbon monoxide sufficient to enhance the survival and/or function of the donor organ, tissue or cell.

In another aspect, the invention provides a method of maintaining an animal cell in vitro that includes providing a vessel containing a pressurized gas that includes carbon monoxide gas, providing an isolated cell in vitro, wherein the cell is a primary cell or stem cell, releasing the pressurized gas from the vessel to form an atmosphere that includes carbon monoxide gas, and maintaining the animal cell in vitro in the presence of the atmosphere that includes carbon monoxide gas.

If desired, the cell can then be transplanted into a recipient. The cell may be obtained from a donor that is not the recipient, or it may be obtained from the recipient. Further, a carbon monoxide composition can be administered to the recipient prior to, and/or during, and/or after the transplantation step. This composition will typically be in the form of an inhaled gas.

In another embodiment, the animal cell is obtained from a donor by a method that includes administering a composition comprising carbon monoxide to the donor and obtaining the cell from a tissue of the donor.

The invention also provides a method of maintaining an animal cell in vitro that includes providing a culture medium containing an effective amount of carbon monoxide, for example, at least 0.0001 g CO/100 g medium, and maintaining an isolated cell in the medium. The medium can contain, for example, at least 0.0002, 0.0004, 0.0006, 0.0008, 0.0010, 0.0013, 0.0014, 0.0015, 0.0016, 0.0018, 0.0020, 0.0021, 0.0022, 0.0024, 0.0026, 0.0028, 0.0030, 0.0032, 0.0035, 0.0037, 0.0040, 0.0042, or 0.0044 g CO/100 g medium.

Further, the invention provides a method of enhancing survival of an animal cell after removal from a donor that includes administering to a live or brain-dead donor a pharmaceutical composition comprising carbon monoxide, and obtaining an isolated cell from the donor. The pharmaceutical composition can be, for example, supplied in the form of a pressurized gas suitable for inhalation by the donor.

The method cam further include the step of maintaining the cell in vitro in the presence of a second composition containing carbon monoxide.

While in vitro the cell may be disposed in a liquid medium. In such a case, the step of exposing the cell to the second carbon monoxide composition can be performed by providing a source of pressurized carbon monoxide gas and contacting the liquid medium with carbon monoxide gas released from the source. The liquid medium itself may also be provided as a carbon monoxide composition, i.e., with carbon monoxide dissolved therein.

Further, the invention provides a method of transplanting an animal cell that includes the steps of administering to a live or brain-dead donor a pharmaceutical composition comprising carbon monoxide, obtaining an isolated cell from the donor, and transplanting the cell into a recipient. The animal cell may be obtained from a donor that is not the recipient, or it may be obtained from the recipient. If desired, a carbon monoxide composition can be administered to the recipient prior to and/or during and/or after the transplantation step.

The invention also provides a method of enhancing survival or function of an animal cell transplanted into a recipient that includes the steps of transplanting an animal cell into a recipient and before, during, and/or after the transplanting step, causing the recipient to inhale a sufficient amount of carbon monoxide gas to enhance survival or function of the transplanted cell in the recipient. The carbon monoxide gas can be supplied in the form of a vessel containing pressurized gas that includes carbon monoxide. In one embodiment, the cell is maintained in vitro in an atmosphere comprising carbon monoxide prior to the transplant step. For example, the animal cell can be maintained in a liquid medium that includes at least at least 0.0001 g carbon monoxide/100 g medium (e.g., at least about 0.0002, 0.0004, 0.0006, 0.0008, 0.0010, 0.0013, 0.0014, 0.0015, 0.0016, 0.0018, 0.0020, 0.0021, 0.0022, 0.0024, 0.0026, 0.0028, 0.0030, 0.0032, 0.0035, 0.0037, 0.0040, 0.0042, or 0.0044 g CO/100 g medium).

The method can optionally include the step of exposing the cell to a carbon monoxide composition ex vivo, prior to the transplanting step.

The carbon monoxide gas can be administered to the recipient prior to and/or during and/or after the transplantation step. The animal cell may be obtained from a donor that is not the recipient, or it may be obtained from the recipient. A pharmaceutical composition comprising carbon monoxide can be administered to the donor prior to and/or during removal of the cell from the donor.

In another aspect, the invention provides a method of improving survival of a transplanted cell in a recipient that includes administering to the recipient before and/or during and/or after transplantation of the cell into the recipient, an effective amount of a pharmaceutical composition comprising carbon monoxide gas.

In any of the above methods of the invention, the survival effect may be enhanced by inducing the enzyme hemeoxygenase-1 (HO-1) in a donor or recipient, e.g., induced with heme, heavy metals, cytokines, hormones, nitric oxide endotoxins, UV irradiation, or glutathione depletors; or via heat shock. In the donor, such induction can occur prior to or during removal of the organ, tissue, or cells. In the recipient, such induction can occur, prior to, during, or following transplantation. Alternatively, the enzyme can be induced in the organ, tissue, or cells ex vivo, prior to transplantation into the recipient.

The invention further provides an article of manufacture that includes a vessel containing pressurized gas, that contains at least 0.001 ppm, e.g., at least about 1, 10, 50, 100, 150, 200, 250, 300, 500, 1000, 2000, 5000, 10,000, 100,000, 200,000, 300,000, 400,000, 500,000, and up to 1,000,000 ppm carbon monoxide, and a label describing use of the gas to enhance survival of isolated animal cells, tissues, or islets before, during or after transplantation of the cells, tissues, or islets into a patient.

Also within the invention is a sterile cell medium that includes nutrients suitable for maintaining an animal cell in culture and at least about 0.0001 g carbon monoxide/100 g medium, e.g., at least 0.0002, 0.0004, 0.0006, 0.0008, 0.0010, 0.0013, 0.0014, 0.0015, 0.0016, 0.0018, 0.0020, 0.0021, 0.0022, 0.0024, 0.0026, 0.0028, 0.0030, 0.0032, 0.0035, 0.0037, 0.0040, 0.0042, or 0.0044 g CO/100 g medium. It may also contain animal cells.

A method of maintaining an animal cell in vitro and then transplanting it is also provided. The method includes the steps of providing a vessel containing pressurized gas containing carbon monoxide gas; providing an isolated animal cell in vitro, wherein the cell is disposed in a medium that contains dissolved carbon monoxide; releasing the pressurized gas from the vessel to form an atmosphere comprising carbon monoxide gas; maintaining the cell in the presence of the atmosphere; and transplanting the cell into a recipient.

In any of the above aspects or embodiments of the invention, the cell can be any cell. For example, the cell can be an animal cell such as a primary, secondary, or cell line cell. As another example, the cell can be part of a pancreatic islet, e.g., a é-cell. The cell can also be, e.g., a liver cell, a fibroblast, a bone marrow cell, a neuronal cell, a mocyte, a lymphocyte, or a stem cell. In each of the ex vivo methods of the invention, the tissue is preferably not blood and contains little if any whole blood, and the cells are preferably not red blood cells and are not accompanied by a significant number of red blood cells.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. The materials, methods, and examples are illustrative only and not intended to be limiting.

Other features and advantages of the invention will be apparent from the following detailed description, and from the claims.

DETAILED DESCRIPTION

Figure 1A:
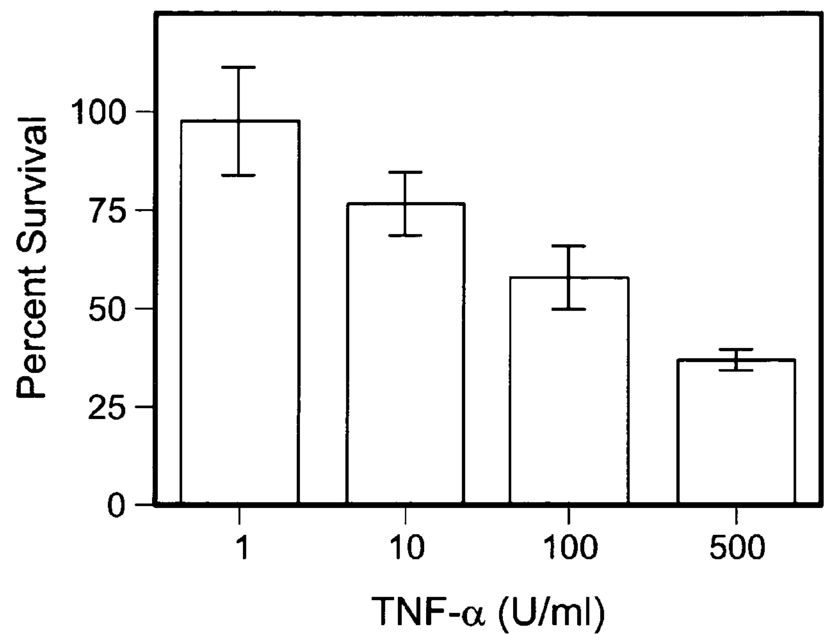
FIG. 1A is a bar graph that illustrates the effect of treatment of βTC3 cells with increasing concentrations of TNF-α.

The term "carbon monoxide" (or "CO") as used herein describes molecular carbon monoxide in its gaseous state, compressed into liquid form, or dissolved in aqueous solution. The terms "carbon monoxide composition" and "pharmaceutical composition comprising carbon monoxide" are used throughout the specification to describe a gaseous, liquid, solid, or semi-solid composition containing carbon monoxide that can be administered to a donor patient, cadaver, or animal; to an organ; or to a portion of an organ, e.g., tissues of the organ, or individual cell(s) that make up the organ, e.g., neurons, hepatocytes, myocytes, islets, or islet cells such as a pancreatic β-cell. The skilled practitioner will recognize which form of the pharmaceutical composition, e.g., gaseous, liquid, or both gaseous and liquid forms, is preferred for a given application.

The terms "effective amount" and "effective to treat," as used herein, refer to an amount or concentration of carbon monoxide utilized for period of time (including acute or chronic administration and periodic or continuous administration) that is effective within the context of its administration for causing an intended effect or physiological outcome. Effective amounts of carbon monoxide for use in the present invention include, for example, amounts that are effective for enhancing survival and/or improving function of organs or cells in vivo and/or in vitro. Within the context of transplantation of individual cells or masses of cells, e.g., transplant donors and/or recipients, an effective amount of carbon monoxide is that amount administered to the transplant donor and/or recipient sufficient to enhance survival of the cell or mass of cells, e.g. to reduce loss of the cell, or mass of cells, and/or to improve functional performance of a transplanted cell or a mass of cells. Within the context of treating cells outside a body, e.g., islet cells to be cultured and/or used for transplantation, an effective amount of carbon monoxide is that amount with which the cells are incubated or stored in order to enhance preservation of the cells and/or to reduce cell loss, e.g., loss via apoptosis, and/or to enhance function. Within the context of transplantation of organs and tissues, e.g., transplant donors and/or recipients, an effective amount of carbon monoxide is that amount administered to the transplant donor and/or recipient sufficient to enhance survival of the organ, tissue or cells of interest, e.g., to reduce loss of cells from which the organ or tissue is composed, and/or to improve functional performance of an organ. Within the context of treating organs, tissues or cells ex vivo to be stored or used for transplantation, an effective amount of carbon monoxide is an amount sufficient to enhance survival and/or function of the organ or tissues. As used herein, the term "inhibiting" includes delaying the onset of, reducing, preventing, or alleviating a biological process, e.g., apoptosis. For gases, effective amounts of carbon monoxide generally fall within the range of about 0.0000001% to about 0.3% by weight, e.g., 0.0001% to about 0.25% by weight, preferably at least about 0.001%, e.g., at least 0.005%, 0.010%, 0.02%, 0.025%, 0.03%, 0.04%, 0.05%, 0.06%, 0.08%, 0.10%, 0.15%, 0.20%, 0.22%, or 0.24% by weight of carbon monoxide. Preferred ranges of carbon monoxide include 0.001% to about 0.24%, about 0.005% to about 0.22%, about 0.01% to about 0.20%, and about 0.01% to about 0.1% by weight. For liquid solutions of CO, effective amounts generally fall within the range of about 0.0001 to about 0.0044 g CO/100 g liquid, e.g., at least 0.0002, 0.0004, 0.0006, 0.0008, 0.0010, 0.0013, 0.0014, 0.0015, 0.0016, 0.0018, 0.0020, 0.0021, 0.0022, 0.0024, 0.0026, 0.0028, 0.0030, 0.0032, 0.0035, 0.0037, 0.0040, or 0.0042 g CO/100 g aqueous solution. Preferred ranges include, e.g., about 0.0010 to about 0.0030 g CO/100 g liquid, about 0.0015 to about 0.0026 g CO/100 g liquid, or about 0.0018 to about 0.0024 g CO/100 g liquid. A skilled practitioner will appreciate that amounts outside of these ranges may be used, depending upon the application.

The term "patient" is used throughout the specification to describe an animal, human or non-human, to whom treatment according to the methods of the present invention is provided. Veterinary applications are clearly anticipated by the present invention. The term includes but is not limited to birds, reptiles, amphibians, and mammals, e.g., humans, other primates, pigs, rodents such as mice and rats, rabbits, guinea pigs, hamsters, cows, horses, cats, dogs, sheep and goats. The term "donor" or "donor patient" as used herein refers to an animal (human or non-human) from whom an organ, tissue or individual cells can be obtained for the purposes of storage and/or transplantation to a recipient patient. The term "recipient" or "recipient patient" refers to an animal (human or non-human) into which an organ, tissue, mass of cells or individual cells can be transferred.

The term "diabetes" is a general term to describe diabetic disorders as they are recognized in the art, e.g., Diabetes Mellitus. Diabetes Mellitus is characterized by an inability to regulate blood glucose levels. The two most prevalent types of diabetes are known as Type I and Type II diabetes. In Type I, or insulin-dependent diabetes (IDDM), the pancreas makes little or no insulin because the insulin-producing beta cells have been destroyed. In Type II, or noninsulin-dependent diabetes (NIDDM), the pancreas makes some insulin but the insulin is not effective. The term also encompasses the myriad secondary disorders caused by diabetes, both acute and chronic, e.g., diabetic complications, e.g., hypoglycemia and hyperglycemia, retinopathy, angiopathy, neuropathy, and nephropathy.

The term "cell(s)" or "animal cell(s)" as used herein refers to any type of animal cells, including animal cells suitable for transplantation. The cells are typically primary cells obtained from an animal donor, but can be secondary cells or even cells of an established cell line. They are optionally transfected ex vivo with an expression vector that alters their function in some way. The cells include, but are not limited to, e.g., islet cells, e.g., cells which are part of a pancreatic islet, and liver cells, fibroblasts, bone marrow cells, myocytes, and stem cells, and cells of the central nervous system, including the spinal cord. The term "islet cell(s)" is used throughout the specification as a general term to describe the clumps of cells within the pancreas known as islets, e.g., islets of Langerhans. Islets of Langerhans contain several cell types that include, e.g., β-cells (which make insulin), α-cells (which produce glucagons), γ-cells (which make somatostatin), F cells (which produce pancreatic polypeptide), enterochromaffin cells (which produce serotonin), PP cells and D1 cells. The term "stem cell" is an art recognized term that refers to cells having the ability to divide for indefinite periods in culture and to give rise to specialized cells. Included within this term are, for example, totipotent, pluripotent, multipotent, and unipotent stem cells, e.g., neuronal, liver, muscle, and hematopoietic stem cells.

By "isolated cell" is meant that the cell is removed from the tissue or organ in which it (or its predecessor) naturally occurs. A cell can be just partially purified from its natural milieu and be deemed "isolated." For example, an intact islet of Langerhans is considered to be made up of "isolated" cells, once the islet is removed from a pancreas and can be physically separated from other islets. The cells of an intact organ such as a kidney or heart or a partial organ such as a piece of a blood vessel are not considered to be "isolated cells" while still part of the organ.

The term "organ(s)" is used throughout the specification as a general term to describe any anatomical part or member having a specific function in the animal. Further included within the meaning of this term are substantial portions of organs, e.g., cohesive tissues obtained from an organ. Such organs include but are not limited to kidney, liver, heart, intestine, e.g., large or small intestine, pancreas, and lungs. Further included in this definition are bones and blood vessels, e.g., aortic transplants.

The term "transplantation" is used throughout the specification as a general term to describe the process of implanting an organ, tissue, mass of cells, or individual cells into a patient. The term "transplantation" is defined in the art as the transfer of living tissues or cells from a donor to a recipient, with the intention of maintaining the functional integrity of the transplanted tissue or cells in the recipient (see, e.g., *The Merck Manual*, Berkow, Fletcher, and Beers, Eds., Merck Research Laboratories, Rahway, N.J., 1992). The term "cell transplantation" is used throughout the specification as a general term to describe the process of transferring at least one cell, e.g., an islet cell(s), to a patient. For example, such transplantation can be performed by removing the β-cells (or intact islets) from a donor's pancreas and putting them into a recipient patient whose pancreas cannot produce sufficient insulin. The terms include all categories of transplants known in the art, except blood transfusions. Transplants are categorized by site and genetic relationship between donor and recipient. The term includes, e.g., autotransplantation (removal and transfer of cells or tissue from one location on a patient to the same or another location on the same patient), allotransplantation (transplantation between members of the same species), and xenotransplantation (transplantations between members of different species).

The terms "organ rejection", "transplant rejection" or "rejection" are art-recognized, and are used throughout the specification as a general term to describe the process of rejection of an organ, tissues, or cells in a recipient. Included within the definition are, for example, three main patterns of rejection that are usually identified in clinical practice: hyperacute rejection, acute rejection, and chronic rejection (see, e.g., *Oxford Textbook of Surgery*, Morris and Malt, Eds., Oxford University Press, 1994).

The terms "marginal donor(s)" and "marginal organ" are used herein as general terms to describe a donor or organ presenting with problems that render its use in a transplantation procedure less than optimal. For example, a marginal donor can include a donor that is older than 50 years old, or that is afflicted with a chronic disease that may affect graft function, e.g., diabetes, HTA and alcohol intake. A marginal organ is, for example, (1) an organ from such a donor, or (2) an organ that has experienced prolonged warm or cold ischemia times, or (3) an organ that presents with anatomical abnormalities (e.g., small and multiple vessels, e.g., in the kidney) that can render the vascular anastomosis difficult, or with evidence of atherosclerostic plaques on graft vessels.

Preparation of Gaseous Compositions

A carbon monoxide composition may be a gaseous carbon monoxide composition. Compressed or pressurized gas useful in the methods of the invention can be obtained from any commercial source, and in any type of vessel appropriate for storing compressed gas. For example, compressed or pressurized gases can be obtained from any source that supplies compressed gases, such as oxygen, for medical use. The pressurized gas including carbon monoxide used in the methods of the present invention can be provided such that all gases of the desired final composition (e.g., CO and $O_2$, and optionally $N_2$, He, and/or $CO_2$) are mixed together in the same vessel. If desired, the methods of the present invention can be performed using multiple vessels containing individual gases. For example, a single vessel can be provided that contains carbon monoxide, with or without other gases, the contents of which can be optionally mixed with room air or with the contents of other vessels, e.g., vessels containing oxygen, nitrogen, carbon dioxide, compressed air, or any other suitable gas or mixtures thereof.

Gaseous compositions administered to a patient according to the present invention typically contain 0% to about 79% by weight nitrogen, about 21% to about 100% by weight oxygen and about 0.0000001% to about 0.3% by weight (corresponding to about 0.001 ppm (i.e., 1 ppb) to about 3,000 ppm) carbon monoxide. Preferably, the amount of nitrogen in the gaseous composition is about 79% by weight, the amount of oxygen is about 21% by weight and the amount of carbon monoxide is about 0.0001% to about 0.25% by weight. The amount of carbon monoxide is preferably at least about 0.001%, e.g., at least about 0.005%, 0.01%, 0.02%, 0.025%, 0.03%, 0.04%, 0.05%, 0.06%, 0.08%, 0.10%, 0.15%, 0.20%, 0.22%, or 0.24% by weight. Preferred ranges of carbon monoxide include about 0.001% to about 0.24%, about 0.005% to about 0.22%, about 0.010% to about 0.20%, and about 0.015% to about 0.1% by weight. It is noted that gaseous carbon monoxide compositions having concentrations of carbon monoxide greater than 0.3% (such as 1% or greater) may be used for short periods (e.g., one or a few breaths), depending upon the application. They are particularly useful for ex vivo applications, where carbon monoxide poisoning is not a risk. Where the gas is used to form an atmosphere for cultivation of cells in vitro, the gas can contain carbon dioxide as well, to help maintain the pH of the medium. The carbon dioxide can be present at, for example, 1% to 10%, commonly 5%, by weight.

A gaseous carbon monoxide composition may be used to create an atmosphere that comprises carbon monoxide gas. An atmosphere that includes appropriate levels of carbon monoxide gas can be created, for example, by providing a vessel containing a pressurized gas comprising carbon monoxide gas, and releasing the pressurized gas from the vessel into a chamber or space to form an atmosphere that includes the carbon monoxide gas inside the chamber or space. Alternatively, the gases can be released into an apparatus that culminates in a breathing mask or breathing tube, thereby creating an atmosphere comprising carbon monoxide gas in the breathing mask or breathing tube and ensuring the patient is the only person in the room exposed to significant levels of carbon monoxide.

Carbon monoxide levels in an atmosphere or a ventilation circuit can be measured or monitored using any method known in the art. Such methods include electrochemical detection, gas chromatography, radioisotope counting, infrared absorption, colorimetry, and electrochemical methods based on selective membranes (see, e.g., Sunderman et al., Clin. Chem. 28:2026–2032, 1982; Ingi et al., Neuron 16:835–842, 1996). Sub-parts per million carbon monoxide levels can be detected by, e.g., gas chromatography and radioisotope counting. Further, it is known in the art that carbon monoxide levels in the sub-ppm range can be measured in biological tissue by a midinfrared gas sensor (see, e.g., Morimoto et al., Am. J. Physiol. Heart. Circ. Physiol 280:H482–H488, 2001). Carbon monoxide sensors and gas detection devices are widely available from many commercial sources.

Preparation of Liquid Compositions

A carbon monoxide composition may also be a liquid carbon monoxide composition. A liquid can be made into a carbon monoxide composition by any method known in the art for causing gases to become dissolved in liquids. For example, the liquid can be placed in a so-called "$CO_2$ incubator" and exposed to a continuous flow of carbon monoxide until a desired concentration of carbon monoxide is reached in the liquid. As another example, carbon monoxide gas can be "bubbled" directly into the liquid until the desired concentration of carbon monoxide in the liquid is reached. The amount of carbon monoxide that can be dissolved in a given aqueous solution increases with decreasing temperature. As still another example, an appropriate liquid may be passed through tubing that allows gas diffusion, where the tubing runs through an atmosphere comprising carbon monoxide (e.g., utilizing a device such as an extracorporeal membrane oxygenator). The carbon monoxide diffuses into the liquid to create a liquid carbon monoxide composition.

The liquid can be any liquid known to those of skill in the art to be suitable for administration to patients (see, for example, Oxford Textbook of Surgery, Morris and Malt, Eds., Oxford University Press, 1994) or for maintaining organs, tissues or cells ex vivo. In general, the liquid will be an aqueous solution. Examples of solutions include Phosphate Buffered Saline (PBS), Celsior™ solution, Perfadex™ solution, Collins solution, citrate solution, and University of Wisconsin (UW) solution (Oxford Textbook of Surgery, Morris and Malt, Eds., Oxford University Press, 1994). The liquid compositions can include carbon monoxide at concentrations in the range of about 0.0001 to about 0.0044 g CO/100 g liquid, e.g., at least 0.0002, 0.0004, 0.0006, 0.0008, 0.0010, 0.0013, 0.0014, 0.0015, 0.0016, 0.0018, 0.0020, 0.0021, 0.0022, 0.0024, 0.0026, 0.0028, 0.0030, 0.0032, 0.0035, 0.0037, 0.0040, or 0.0042 g CO/100 g aqueous solution. Preferred ranges include, e.g., about 0.0010 to about 0.0030 g CO/100 g liquid, about 0.0015 to about 0.0026 g CO/100 g liquid, or about 0.0018 to about 0.0024 g CO/100 g liquid. For water at 0° C., the saturation point is about 0.0044 g CO/100 g medium.

Any suitable liquid can be saturated to a set concentration of carbon monoxide via gas diffusers. Alternatively, premade solutions that have been quality controlled to contain set levels of carbon monoxide can be used. Accurate control of dose can be achieved via measurements with a gas permeable, liquid impermeable membrane connected to a carbon monoxide analyzer. Solutions can be saturated to desired effective concentrations and maintained at these levels. In both liquid and gaseous compositions, the inclusion of the inert gas helium can improve carbon monoxide delivery to the tissues of an organ.

Treatment of Patients with Carbon Monoxide Compositions

The present invention contemplates the use of carbon monoxide compositions to treat donors, recipients, organs, tissues, masses of cells, and/or individual cells at any step of the harvesting, storage and transplant process. An organ, a tissue, a mass of cells, or individual cells may be harvested from a donor, treated with a carbon monoxide composition ex vivo in accordance with the present invention, and transplanted into a recipient. Alternatively or in addition, the organ, tissue, mass of cells, or individual cells can be treated in situ, while still in the donor. Optionally, a carbon monoxide composition can be administered to the recipient prior to, during, and/or after the surgery: e.g., after an organ is reperfused with the recipient's blood. The carbon monoxide composition may also be administered to the donor prior to or during the process of harvesting the organ, tissue, mass of cells, or individual cells.

Organs, tissues, masses of cells, and/or isolated cells can be harvested from a donor and transplanted by any methods known to those of skill in the art (see, for example, *Oxford Textbook of Surgery*, Morris and Malt, Eds., Oxford University Press (1994)). The skilled practitioner will recognize that methods for harvesting and transplantation may vary depending upon many circumstances, such as the type of organ, tissue or cells and the type of donor.

It is further contemplated by the present invention that the methods described herein can be used with organs, tissue, masses of cells or isolated cells ex vivo, e.g., bioartificial organs, such as a bioartificial liver, kidney or pancreas (see, e.g., Sambanis et al., *Cytotechnology* 15:351–363, 1994). The organs, tissues, or cells (or masses of cells) can be treated with carbon monoxide either prior to putting them in the device, or while they are utilized in the device, or both. Alternatively or in addition, the donor animal can be administered carbon monoxide prior to removal of the organ, tissue, mass of cells, or individual cells for use in the device.

Alternatively or in addition, a cell can be cultured as described below and transplanted into a recipient.

A patient can be treated with a carbon monoxide composition by any method known in the art of administering gases and/or liquids to patients. The present invention contemplates the systemic administration of liquid or gaseous carbon monoxide compositions to patients (e.g., by inhalation and/or ingestion), and the topical administration of the compositions to the patient's organs or tissues in situ (e.g., by ingestion, insufflation, and/or introduction into the abdominal cavity).

The present invention also contemplates the use of carbon monoxide compositions to treat patients to inhibit endothelial cell apoptosis, e.g., as it occurs during hyperoxia, endotoxic shock, arteriosclerosis, ischemia reperfusion injury, and acute or chronic graft rejection.

Systemic Delivery of Carbon Monoxide

Gaseous carbon monoxide compositions can be delivered systemically to a patient, e.g., a patient undergoing or in need of a transplant. Gaseous carbon monoxide compositions are typically administered by inhalation through the mouth or nasal passages to the lungs, where the carbon monoxide is readily absorbed into the patient's bloodstream. The concentration of active compound (CO) utilized in the therapeutic gaseous composition will depend on absorption, distribution, inactivation, and excretion (generally, through respiration) rates of the carbon monoxide as well as other factors known to those of skill in the art. It is to be further understood that for any particular subject, specific dosage regimens be adjusted over time according to the individual need and the professional judgment of the person administering or supervising the administration of the compositions, and that the concentration ranges set forth herein are exemplary only and are not intended to limit the scope or practice of the claimed invention. Acute, sub-acute and chronic administration of carbon monoxide are contemplated by the present invention, depending upon, e.g., the severity or persistence of the disorder in the patient. Carbon monoxide can be delivered to the patient for a time (including indefinitely) sufficient to treat the condition and exert the intended pharmacological or biological effect.

The following are examples of some methods and devices that can be utilized to administer gaseous carbon monoxide compositions to patients.

Ventilators

Carbon monoxide (concentrations can vary) can be purchased mixed with air or another oxygen-containing gas in a standard tank of compressed gas (e.g., 21% $O_2$, 79% $N_2$). It is non-reactive, and the concentrations that are required for the methods of the present invention are well below the combustible range (10% in air). In a hospital setting, the gas presumably will be delivered to the bedside where it will be mixed with oxygen or house air in a blender to a desired concentration. The patient will inhale the gas mixture through a ventilator, which will be set to a flow rate based on patient comfort and needs. This is determined by pulmonary graphics (i.e., respiratory rate, tidal volumes, etc.). Fail-safe mechanism(s) to prevent the patient from unnecessarily receiving greater than desired amounts of carbon monoxide can be designed into the delivery system. The patient's carbon monoxide level can be monitored by studying (1) carboxyhemoglobin (COHb), which can be measured in venous blood, and (2) exhaled carbon monoxide collected from a side port of the ventilator. Carbon monoxide exposure can be adjusted based upon the patient's health status and on the basis of the markers. If necessary, carbon monoxide can be washed out of the patient by switching to 100% $O_2$ inhalation. Carbon monoxide is not metabolized; thus, whatever is inhaled will ultimately be exhaled except for a very small percentage that is converted to $CO_2$. Carbon monoxide can also be mixed with any level of $O_2$ to provide therapeutic delivery of carbon monoxide without consequential hypoxic conditions.

Face Mask and Tent

A carbon monoxide-containing gas mixture is prepared as above to allow inhalation by the patient using a facemask or tent. The concentration inhaled can be changed and can be washed out by simply switching over to 100% $O_2$. Monitoring of carbon monoxide levels would occur at or near the mask or tent with a fail-safe mechanism that would prevent too high of a concentration of carbon monoxide from being inhaled.

Portable Inhaler

Compressed carbon monoxide can be packaged into a portable inhaler device and inhaled in a metered dose, for example, to permit intermittent treatment of a recipient who is not in a hospital setting. Different concentrations of carbon monoxide could be packaged in the containers. The device could be as simple as a small tank (e.g., under 5 kg) of appropriately diluted CO with an on-off valve and a tube from which the patient takes a whiff of CO according to a standard regimen or as needed.

Intravenous Artificial Lung

An artificial lung (a catheter device for gas exchange in the blood) designed for $O_2$ delivery and $CO_2$ removal can be used for carbon monoxide delivery. The catheter, when implanted, resides in one of the large veins and would be able to deliver carbon monoxide at given concentrations either for systemic delivery or at a local site. The delivery can be a local delivery of a high concentration of carbon monoxide for a short period of time at a specific site (this high concentration would rapidly be diluted out in the bloodstream), or a relatively longer systemic exposure to a lower concentration of carbon monoxide (see, e.g., Hattler et al., Artif. Organs 18(11):806–812, 1994; and Golob et al., ASAIO J. 47(5):432–437, 2001).

Normobaric Chamber

In certain instances, it would be desirable to expose the whole patient to carbon monoxide. The patient would be inside an airtight chamber that would be flooded with carbon monoxide (at a level that does not endanger the patient, or at a level that poses an acceptable risk without the risk of bystanders being exposed). Upon completion of the exposure, the chamber could be flushed with air (e.g., 21% $O_2$, 79% $N_2$), and samples could be analyzed by carbon monoxide analyzers to ensure no carbon monoxide remains before allowing the patient to exit the exposure system.

Aqueous Solutions

The present invention further contemplates that aqueous solutions comprising carbon monoxide can be created for systemic delivery to a patient, e.g., for oral delivery and/or by injection into the body, e.g., intravenously, intra-arterially, intraperitoneally and/or subcutaneously.

Preservation buffers and culture media can be saturated to a set concentration of carbon monoxide via gas diffusers or pre-made stock solutions that have been quality controlled to contain set levels of carbon monoxide. Accurate control of dose can be achieved via measurements with a gas permeable, liquid impermeable membrane connected to a carbon monoxide analyzer. The buffers and solutions can be saturated to desired effective concentrations and maintained at these levels. For procedures that require perfusion of a given organ, tissue, or cell preparation, pre-made saturated solutions can be on hand to maintain the levels of carbon monoxide. If carbon monoxide levels drop, fresh solutions can be added to replace those where carbon monoxide concentrations have dropped. Once the preparation of the organ, tissue or cell has been accomplished, it can be maintained in the solution in an airtight container for transport. The presence of the inert gas helium makes uptake of carbon monoxide more efficient.

Topical Treatment of Organs, Tissues, and Isolated Cells with Carbon Monoxide In Situ and Ex Vivo.

The present invention features methods of transplanting an organ(s), tissues, masses of cells and/or isolated cells. The methods can include a step of exposing the organ(s), tissues, mass of cells and/or isolated cells to a carbon monoxide composition prior to transplantation. Such exposures can occur in situ and/or ex vivo. The organ(s), tissues and/or isolated cells may be exposed to an atmosphere comprising carbon monoxide gas, to a liquid carbon monoxide composition, e.g., a liquid perfusate, storage solution, or wash solution having carbon monoxide dissolved therein, or both.

Exposure of an organ or tissue to liquid carbon monoxide compositions can be performed ex vivo and/or in situ by any method known in the art. For example, the exposure may be performed ex vivo in any chamber or space having sufficient volume for submerging the organ or tissue, completely or partially, in the carbon monoxide composition. As another example, the organ may be exposed to a carbon monoxide composition by placing the organ in any suitable container, and causing the carbon monoxide composition to "wash over" the organ, such that the organ is exposed to a continuous flow of the carbon monoxide composition.

Alternatively, the organ may be perfused with a carbon monoxide composition. The term "perfusion" is an art recognized term, and relates to the passage of a liquid, e.g., a carbon monoxide composition, through the blood vessels of an organ or tissue. Methods for perfusing organs ex vivo and in situ are well known in the art. An organ can be perfused with a carbon monoxide composition ex vivo, for example, by continuous hypothermic machine perfusion (see *Oxford Textbook of Surgery*, Morris and Malt, Eds., Oxford University Press, 1994). Optionally, in in situ or ex vivo perfusions, the organ can be perfused with a wash solution, e.g., UW solution without carbon monoxide, prior to perfusion with the carbon monoxide composition, to remove the donor's blood from the organ. Such a process could be performed to avoid competition for carbon monoxide by the donor's hemoglobin. As another option, the wash solution can be a carbon monoxide composition. An appropriate liquid may be passed through tubing that allows gas diffusion; this tubing runs through an atmosphere comprising carbon monoxide (e.g., through a chamber, such as with extracorporeal membrane oxygenation), to create a liquid carbon monoxide composition, which may then be passed into an organ (e.g., perfused into the organ by connecting the tubing to the organ).

The organ or tissue may be placed, e.g., submerged, in a medium or solution that does not include carbon monoxide, and placed in a chamber that exposes thee medium or solution to a carbon monoxide-containing atmosphere. Alternatively or in addition, carbon monoxide can be "bubbled" into the medium or solution. In situ exposures can be performed by any method known in the art, e.g., by in situ flushing or perfusion of the organ with a liquid carbon monoxide composition (see *Oxford Textbook of Surgery*, Morris and Malt, Eds., Oxford University Press, 1994).

The present invention contemplates that any or all of the above methods for exposing an organ or tissue to a liquid carbon monoxide composition, e.g., washing, submerging, or perfusing, can be used in a given transplantation procedure.

The present invention further contemplates that a solid or semi-solid carbon monoxide composition can be created. For example, a liquid that is a carbon monoxide composition, as described above, can be made into a solid or semi-solid composition, in which an organ or tissue may be overlaid or embedded. Alternatively, a semi-solid carbon monoxide composition can be infused into the organ. Solid or semi-solid compositions can be made, for example, by adding a solidifying agent such as a gelling agent (e.g., collagen or alginate) to the liquid.

Cell Culture

The present invention features a method of maintaining or culturing an animal cell in vitro. The method can include the steps of providing a vessel containing a pressurized gas comprising carbon monoxide gas, providing an animal cell in vitro and releasing the pressurized gas from the vessel to form an atmosphere that includes the carbon monoxide gas. The animal cell is then cultured or simply maintained in the presence of the atmosphere comprising carbon monoxide gas.

The method can be performed in any chamber or space suitable for creating an atmosphere that includes appropriate levels of carbon monoxide gas. Such chambers or spaces include, e.g., incubators, mixing cylinders, and any vessel suitable for culturing or holding cells, such as roller bottles, cell culture flasks, petri dishes, and test tubes. For example, a $CO_2$ incubator may be used, wherein carbon monoxide gas is supplied in a continuous flow from a vessel that contains the gas. As another example, a roller bottle may be used, wherein carbon monoxide is included to create an appropriate atmosphere inside the roller bottle.

The skilled practitioner will appreciate that culture conditions, e.g., temperature, can be selected and/or varied depending upon the type of cell to be cultured (see, for example, *Cells: A Laboratory Manual*, Spector and Leinwand, Eds., Cold Spring Harbor Laboratory Press, Cold Spring Harbor, N.Y., 1997). For example, the murine insulinoma cell line βTC3 (DSMZ, Braunschweig, Germany) can be incubated in humidified 5% $CO_2$/95% air at 37° C.

The animal cell may be disposed, e.g., suspended or bathed in, a liquid medium. The medium can be any medium known to those of skill in the art to be suitable for culturing, preserving, or washing the cells of interest (see, for example, *Cells: A Laboratory Manual*, Spector and Leinwand, Eds., Cold Spring Harbor Laboratory Press, Cold Spring Harbor, N.Y., 1997). Such types of media include, but are not limited to, various buffers, Eagle's minimal essential medium (MEM), Dulbecco/Vogt modified Eagle's minimal essential medium (DMEM), or Roswell Park Memorial Institute (RPMI) Medium. Such media may also comprise appropriate supplements, e.g., fetal bovine serum (FBS), individual amino acids, antibiotics, and/or vitamins. For example, the medium can be RPMI medium 1640 (Life Technologies, Grand Island, N.Y.) supplemented with 2 mM L-glutamine, 100 U/ml penicillin G, 100 U/ml streptomycin and 10% Fetal Calf Serum (FCS) (Life Technologies). In those embodiments of the present invention wherein the cells are in a liquid medium, the cells can be exposed to a carbon monoxide composition by contacting the liquid medium with pressurized gas comprising carbon monoxide, e.g., with carbon monoxide gas released from a source of pressurized gas in accordance with the methods of the invention.

In another embodiment of the present invention, the liquid medium itself is a carbon monoxide composition, created as described above. The medium can be infused with carbon monoxide before or following addition of the cells to the medium.

The present invention further contemplates that a solid or semi-solid medium can be created wherein the solid or semi-solid medium is a carbon monoxide composition. For example, a liquid medium that is a carbon monoxide composition, as described above, can be made into a solid or semi-solid medium, in which cells may be overlaid or embedded. Such a process can be carried out, for example, by adding a gelling agent such as collagen, alginate or agar to a medium.

Use of Hemoxygenase-1, Compounds Associated with Hemoxygenase-1, and Other Compounds and Treatments Also contemplated by the present invention is the induction or expression of hemeoxygenase-1 (HO-1) in conjunction with administration of carbon monoxide. HO-1 can be provided to a patient by inducing or expressing HO-1 in the patient, or by administering exogenous HO-1 directly to the patient. As used herein, the term "induce(d)" means to cause increased production of a protein, e.g., HO-1, in isolated cells or the cells of a tissue, organ or animal using the cells' own endogenous (e.g., non-recombinant) gene that encodes the protein.

HO-1 can be induced in a patient, e.g., a donor and/or recipient, by any method known in the art. For example, production of HO-1 can be induced by hemin, by iron protoporphyrin, or by cobalt protoporphyrin. A variety of non-heme agents including heavy metals, cytokines, hormones, nitric oxide, $COCl_2$, endotoxin and heat shock are also strong inducers of HO-1 expression (Otterbein et al., Am. J. Physiol. Lung Cell Mol. Physiol. 279:L1029–L1037, 2000; Choi et al., Am. J. Respir. Cell Mol. Biol. 15:9–19, 1996; Maines, Annu. Rev. Pharmacol. Toxicol. 37:517–554, 1997; and Tenhunen et al., J. Lab. Clin. Med. 75:410–421, 1970). HO-1 is also highly induced by a variety of agents and conditions that create oxidative stress, including hydrogen peroxide, glutathione depletors, UV irradiation and hyperoxia (Choi et al., Am. J. Respir. Cell Mol. Biol. 15: 9–19, 1996; Maines, Annu. Rev. Pharmacol. Toxicol. 37:517–554, 1997; and Keyse et al., Proc. Natl. Acad. Sci. USA 86:99–103, 1989). A "pharmaceutical composition comprising an inducer of HO-1" means a pharmaceutical composition containing any agent capable of inducing HO-1 in a patient, e.g., any of the agents described above, e.g., hemin, iron protoporphyrin, and/or cobalt protoporphyrin.

HO-1 expression in a cell can be increased via gene transfer. As used herein, the term "express(ed)" means to cause increased production of a protein, e.g., HO-1 or ferritin, in isolated cells or the cells of a tissue, organ or animal using an exogenously administered gene (e.g., a recombinant gene). The HO-1 or ferritin is preferably of the same species (e.g., human, mouse, rat, etc.) as the transplant recipient, in order to minimize any immune reaction. Expression could be driven by a constitutive promoter (e.g., cytomegalovirus promoters) or a tissue-specific promoter (e.g., milk whey promoter for mammary cells or albumin promoter for liver cells). An appropriate gene therapy vector (e.g., retrovirus, adenovirus, adeno associated virus (AAV), pox (e.g., vaccinia) virus, human immunodeficiency virus (HIV), the minute virus of mice, hepatitis B virus, influenza virus, Herpes Simplex Virus-1, and lentivirus) encoding HO-1 or ferritin would be administered to the patient orally, by inhalation, or by injection at a location appropriate for treatment of transplant rejection. Particularly preferred is local administration directly to the donor's organ, tissue or cells to be transplanted, or to the site of the transplant in the recipient. Similarly, plasmid vectors encoding HO-1 or apo-ferritin can be administered, e.g., as naked DNA, in liposomes, or in microparticles.

Further, exogenous HO-1 protein can be directly administered to a patient by any method known in the art. Exogenous HO-1 can be directly administered in addition to, or as an alternative, to the induction or expression of HO-1 in the patient as described above. The HO-1 protein can be delivered to a patient, for example, in liposomes, and/or as a fusion protein, e.g., as a TAT-fusion protein (see, e.g., Becker-Hapak et al., Methods 24:247–256, 2001).

Alternatively or in addition, any of the products of metabolism by HO-1, e.g., bilirubin, biliverdin, iron, and/or ferritin, can be administered to a patient in conjunction with, or instead of, carbon monoxide in order to prevent or treat the disorder. Further, the present invention contemplates that iron-binding molecules other than ferritin, e.g., desferoxamine (DFO), iron dextran, and/or apoferritin, can be administered to the patient. Any of the above compounds can be administered to the patient topically and/or systemically.

Also contemplated by the present invention is the administration of nitric oxide (NO) to a patient, organ(s), tissue(s) and/or isolated cells in conjunction with administration of carbon monoxide, HO-1 and/or HO-1 associated compounds. This technique includes providing NO to the donor, the recipient, or the gorgan, tissue or cell ex vivo, in conjunction with the administration of HO-1 and/or any or all of the products of heme degradation, e.g., CO, biliverdin, bilirubin, iron, and ferritin.

The term "nitric oxide" (or "NO") as used herein describes molecular nitric oxide in its gaseous state or dissolved in aqueous solution. Gaseous compositions comprising NO are typically administered by inhalation through the mouth or nasal passages to the lungs, where the NO may exert its effect directly or be readily absorbed into the patient's bloodstream. Compressed or pressurized gas, e.g., NO (and/or CO, as described in further detail above), useful in the methods of the invention can be obtained from any commercial source, and in any type of vessel appropriate for storing compressed gas. If desired, the methods of the present invention can be performed using multiple vessels containing individual gases. Alternatively, CO and NO can be combined in a single vessel, diluted if desired in an inert gas.

NO for inhalation is available commercially (e.g., INOmax™, INO Therapeutics, Inc., Clinton, N.J.). The gas may be obtained from commercial supplier typically as a mixture of 200–800 ppm NO in pure $N_2$ gas. The source of NO can be essentially 100% NO, or diluted with $N_2$ or any other inert gas (e.g., helium) to any desired concentration. It is vital that the NO be obtained and stored as a mixture free of any contaminating $O_2$ or higher oxides of nitrogen, because such higher oxides of nitrogen (which can form by reaction of $O_2$ with NO) are potentially harmful to lung tissues. If desired, purity of the NO may be demonstrated with chemiluminescence analysis, using known methods, prior to administration to the patient. Chemiluminescence NO—$NO_x$ analyzers are commercially available (e.g., Model 14A, Thermo Environmental Instruments, Franklin, Mass.). The NO—$N_2$ mixture may be blended with an $O_2$-containing gas (e.g., 100% $O_2$ or air) just prior to inhalation by the patient, using, for example, a calibrated rotameter that has been validated previously with a spirometer. The final concentration of NO in the breathing mixture may be verified with a chemical or chemiluminescence technique well known to those in the field (e.g., Fontijin et al., Anal Chem 42:575, 1970). Alternatively, NO and $NO_2$ concentrations may be monitored by means of an electrochemical analyzer. Any impurities such as $NO_2$ can be scrubbed by exposure to NaOH solutions, baralyme, or sodalime. As an additional control, the $FiO_2$ of the final gas mixture may also be assessed.

Pharmaceutical compositions comprising NO can be administered using any method in the art for administering gases to patients. Safe and effective methods for administration of NO by inhalation are described in, e.g., U.S. Pat. Nos. 5,570,683; 5,904,938; and Frostell et al., Circulation 83:2038–2047, 1991. Some exemplary methods for administering gases (such as CO) to patients are described in detail above, and can be used to administer NO. Examples of methods and devices that can be utilized to administer gaseous pharmaceutical compositions comprising NO to patients include ventilators, face masks and tents, portable inhalers, intravenous artificial lungs (see, e.g., Hattler et al., Artif. Organs 18(11):806–812, 1994; and Golob et al., ASAIO J., 47(5):432–437, 2001), and normobaric chambers. However, the properties of NO may allow/necessitate some modification of these methods. In a hospital or emergency field situation, administration of NO gas can be accomplished, for example, by attaching a tank of compressed NO gas in $N_2$, and a second tank of oxygen or an oxygen/$N_2$ mixture (such as air), to an inhaler designed to mix gas from two sources. By controlling the flow of gas from each source, the concentration of NO inhaled by the patient can be maintained at an optimal level. NO can also be mixed with room air, using a standard low-flow blender (e.g., Bird Blender, Palm Springs, Calif.). NO can be generated from $N_2$ and $O_2$ (i.e., air) by using an electric NO generator. A suitable NO generator is described in U.S. Pat. No. 5,396,882. In addition, NO can be provided intermittently from an inhaler equipped with a source of NO such as compressed NO or an electric NO generator. The use of an inhaler may be particularly advantageous if a second compound (e.g., a phosphodiesterase inhibitor as described in further detail below) is administered, orally or by inhalation, in conjunction with the NO.

Preferably, in a pharmaceutical composition comprising NO gas, the NO concentration at the time of inhalation is about 0.1 ppm to about 300 ppm, e.g., 0.5 ppm to 290 ppm, 1.0 ppm to 280 ppm, 5 ppm to 250 ppm, 10 ppm to 200 ppm, or 10 ppm to 100 ppm, in air, pure oxygen, or another suitable gas or gas mixture. A suitable starting dosage for NO administered by inhalation can be 20 ppm (see, e.g., INOmax™ package insert), and the dosage can vary, e.g., from 0.1 ppm to 100 ppm, depending on the age and condition of the patient, the disease or disorder being treated, and other factors that the treating physician may deem relevant. Acute, sub-acute and chronic administration of NO are contemplated by the present invention. NO can be delivered to the patient for a time (including indefinitely) sufficient to treat the condition and exert the intended pharmacological or biological effect. The concentration can be temporarily increased for short periods of time, e.g., 5 min at 200 ppm NO. This can be done when an immediate effect is desired. Preferred periods of time for exposure of a patient to NO include at least one hour, e.g., at least six hours; at least one day; at least one week, two weeks, four weeks, six weeks, eight weeks, ten weeks or twelve weeks; at least one year; at least two years; and at least five years. The patient can be exposed to the atmosphere continuously or intermittently during such periods. The administration of pharmaceutical compositions comprising NO (and/or CO) can be via spontaneous or mechanical ventilation.

When inhaled NO is administered, it is desirable to monitor the effects of the NO inhalation. Such monitoring can be used, in a particular individual, to verify desirable effects and to identify undesirable side effects that might occur. Such monitoring is also useful in adjusting dose level, duration and frequency of administration of inhaled NO in a given individual.

Gaseous NO can be dissolved in aqueous solution, and utilized in that form. For example, such a solution could be used to bathe an organ, tissue or cells ex vivo, or used to perfuse an organ or tissue in situ. The solution can contain other active agents such as CO, HO-1, heme, biliverdin, and/or bilirubin.

It may be desirable to prolong the beneficial effects of inhaled NO within the patient. In determining how to prolong the beneficial effects of inhaled NO, it is useful to consider that one of the in vivo effects of NO is activation of soluble guanylate cyclase, which stimulates production of cGMP. At least some of the beneficial effects of NO may result from its stimulation of cGMP biosynthesis. Accordingly, a phosphodiesterase inhibitor can be administered in conjunction with NO inhalation to inhibit the breakdown of cGMP by endogenous phosphodiesterases.

The phosphodiesterase inhibitor can be introduced into a patient by any suitable method, including via an oral, transmucosal, intravenous, intramuscular, subcutaneous or intraperitoneal route. Alternatively, the inhibitor can be inhaled by the patient. For inhalation, the phosphodiesterase inhibitor is advantageously formulated as a dry powder or an aerosolized or nebulized solution having a particle or droplet size of less than 10 μm for optimal deposition in the alveoli, and may optionally be inhaled in a gas containing NO.

It may be desirable to prolong the beneficial effects of inhaled NO within the patient. In determining how to prolong the beneficial effects of inhaled NO, it is useful to consider that one of the in vivo effects of NO is activation of soluble guanylate cyclase, which stimulates production of cGMP. At least some of the beneficial effects of NO may result from its stimulation of cGMP biosynthesis. Accordingly, a phosphodiesterase inhibitor can be administered in conjunction with NO inhalation to inhibit the breakdown of cGMP by endogenous phosphodiesterases.

The phosphodiesterase inhibitor can be introduced into a patient by any suitable method, including via an oral, transmucosal, intravenous, intramuscular, subcutaneous or intraperitoneal route. Alternatively, the inhibitor can be inhaled by the patient. For inhalation, the phosphodiesterase inhibitor is advantageously formulated as a dry powder or an aerosolized or nebulized solution having a particle or droplet size of less than 10 μm for optimal deposition in the alveoli, and may optionally be inhaled in a gas containing NO.

A suitable phosphodiesterase inhibitor is ZaprinastŎ (M&B 22948; 2-o-propoxyphenyl-8-azapurine-6-one; Rhone-Poulenc Rorer, Dagenham Essex, UK). ZaprinastŎ selectively inhibits the hydrolysis of cGMP with minimal effects on the breakdown of adenosine cyclic-monophosphate in vascular smooth muscle cells (Trapani et al., J Pharmacol Exp Ther 258:269, 1991; Harris et al., J Pharmacol Exp Ther 249:394, 1989; Lugnier et al., Biochem Pharmacol 35:1743, 1986; Souness et al., Br J Pharmacol 98:725, 1989). When using ZaprinastŎ according to this invention, the preferred routes of administration are intravenous or oral. The suitable dose range may be determined by one of ordinary skill in the art. A stock solution of ZaprinastŎ may be prepared in 0.05 N NaOH. The stock can then be diluted with Ringer's lactate solution to the desired final Zaprinast concentration, immediately before use.

This invention can be practiced with other phosphodiesterase inhibitors. Various phosphodiesterase inhibitors are known in the art, including Viagra® (sildenafil citrate) dipyridamole and theophylline. A suitable route of administration and suitable dose range can be determined by one of ordinary skill in the art.

Administration of NO with phosphodiesterase inhibitors can be performed as follows. The NO is administered at 20 ppm in air for 45 min. At the start of the 45 min period, 1.0 mg of ZaprinastŎ per kg body weight is administered by intravenous infusion over 4 min, followed by a continuous infusion of 0.004 mg/kg/min for the rest of the 45 min period. Alternatively, at the start of the 45 min period, 0.15 mg dipyridamole per kg body weight is administered over 4 min, followed by a continuous infusion of 0.004 mg/kg/min for the rest of the 45 min period. The ZaprinastŎ or dipyridamole is administered in a saline solution.

In the context of transplantation, the present invention further contemplates that other procedures known in the art for enhancing graft survival/function can be used along with the methods described herein. Such procedures include, but are not limited to immunosuppressive therapies and donor specific transfusions (DSTs). For example, a DST can be administered to a recipient prior to, during and/or after the administration of CO, HO-1, other heme-associated products, and/or NO to a recipient. Such administration, e.g., administration of DST(s) along with a treatment described herein, can be carried out prior to, during, and/or after transplantation.

EXAMPLE I

Carbon Monoxide Protects Pancreatic Beta Cells from Apoptosis and Improves Islet Function/Survival After Transplantation

Cell Cultures

The murine insulinoma cell line βTC3 (DSMZ, Braunschweig, Germany) was cultured in Dulbecco's Modified Eagle's Medium (DMEM) (Life Technologies, Grand Island, N.Y., USA) supplemented with 2 mM L-glutamine, 100 U/ml penicillin G, 100 U/ml streptomycin and 10%

Fetal Calf Serum (FCS) (Life Technologies) and incubated in humidified 5% $CO_2$/95% air at 37° C. This murine β-cell line, derived from transgenic mice carrying a hybrid insulin-promoter simian virus 40 tumor antigen, is known to maintain the features of differentiated β-cells for about 50 passages in culture. The cells produce mature insulin from proinsulin I and II in a manner comparable to β-cells in vivo and are inducible up to 30 fold by glucose (Efrat et al., Proc. Natl. Acad. Sci. USA 85:9037–41, 1988). Compared to other frequently used transformed β-cell lines such as RIN-m5F and HIT, levels of secreted insulin are closer to normal β-cells in the βTC3 cell line. Thus, these cells are useful for studying β-cell regulation and gene expression (D'Ambra et al., Endocrinology 726:2815–22, 1990).

Pancreatic islets of Langerhans of C57BL/6 mice were supplied by the islet isolation core facility of the Joslin Diabetes Center.

Crystal Violet Vital Staining

βTC3 were seeded at $2\times10^5$ cells (Nunc, Marsh Products, Rochester, N.Y., USA). Cells were washed once with 500 μl PBS and stained with 200 μl 0.05% Crystal Violet in 20% ethanol for 10 min at RT. Crystal Violet was rinsed. To elute stain from cells, 100 μl 50% acetic acid were added to each well. 50 μl were transferred into a 96 well microtiter plate and read with a microtiter plate reader (EL 340 biokinctics reader, Bio-Tek Instruments) at an absorbance of 562 nm.

Expression Plasmids

The β-galactosidase expression vector (Clontech Laboratories, Palo Alto, Calif.) was cloned into the pcDNA3 vector (Sato et al., J. Immunol. 166:4185–4194, 2001). (Invitrogen, Carlsbad, Calif.). A 1.0 kbp XhoI-HindIII fragment encoding the full length rat HO-1 cDNA was cut from the prHO-1 vector (Shibahara et al., J. Biochem. 113:214–218, 1993) and sub-cloned into the pcDNA3 vector.

Transient Transfections

βTC3 were seeded at $3\times10^5$ cells in 16 mm wells and transfected 15 to 20 hours later using Lipofectamine plus™ reagents (Life Technologies) according to the manufacturer's instructions. Total DNA was maintained constant using empty pcDNA3 vector. The percentage of viable cells was assessed by normalizing the percentage of viable cells of each DNA preparation to the number of control-transfected cells without the apoptotic stimulus (100% viability) (Soares et al., Nature Med. 4:1073–1077, 1998; Sato et al., J. Immunol. 166:4185–4194, 2001).

Flow Cytometry

βTC3 cultures were incubated with recombinant TNF-α (500 or 1000 U/ml) (R&D Systems) for 24 hours and islet cultures were stimulated with TNF-É (5000 U/ml) (R&D Systems) and cyclohexamide (CHX) (50 μg/ml) for 48 hours. βTC3 or islets were harvested, dispersed, fixed in 70% ethanol, and suspended in DNA staining buffer (PBS, pH 7.4, containing 0.1% Triton X-100, 0.1 mM EDTA, 50 μg/ml propidium iodide, 50 mg/ml Rnase A). DNA content was analyzed on a FACScan™ analyzer equipped with Cell QuestŎ Software (Becton Dickinson, Palo Alto, Calif.). Cells with a normal DNA content (2N) were scored as viable, whereas cells with a hypoploid DNA content (<2N, termed $A^0$) were scored as apoptotic. To exclude debris and apoptotic cell-free fragments, all events with an FL-2 area profile below that of chicken erythrocyte nuclei were excluded from analysis.

Cell Treatment and Reagents

Murine recombinant TNF-α (R&D Systems) was dissolved in PBS with 1% bovine serum albumin and added to the culture medium (17.5 ng/ml=500 U) 24 hours after transfection. The caspase-3 inhibitor Z-DEVD-FMK and the caspase-8 inhibitor IETD-CHO (Calbiochem, San Diego, Calif.) were dissolved in dimethyl sulphoxide (DMSO, Sigma) and added to the culture medium (10 μM and 1 μM respectively) two hours before treatment with TNF-α. Tin protoporphyrin (SnPPIX) (Porphyrin Products, Logan, Utah) was dissolved (10 mM) in 100 mM NaOH and added 6 hours after transfection to the culture medium (50 μM). The guanylyl cyclase inhibitor 1H[1,2,4]oxadiazolo[4,3-α] quinoxalin-1 (ODQ; Calbiochem) was dissolved in DMSO and added to the culture medium (100 μM) 6 hours after transfection. The cGMP analogue 8-bromoguanosine-3'-5'-cyclic-monophosphate (8-Br-cGMP) (Sigma) was dissolved in water and added to the culture medium (10 μM) 30 minutes before induction of apoptosis. The protein kinase G inhibitor KT5823 (Calbiochem) was dissolved in DMSO and added to the culture medium (1.6 μM) 6 hours after transfection.

CO Exposure

Cells and islets were exposed to 1% carbon monoxide in compressed air balanced with 5% $CO_2$, as described elsewhere (see, e.g., Otterbein et al., Nature Med. 6:422–428, 2000). Islets were incubated in RPMI medium pre-saturated with carbon monoxide (4° C. overnight, 1% CO, 5% $CO_2$) for two hours at 37° C. while treatment with 1% CO, 5% $CO_2$ was continued.

Mice and Induction of Diabetes

Male C57BL/6 were purchased from Charles River Laboratories (Wilmington, Mass.) and housed in accordance with guidelines from the NIH. The experiments were approved by the Institutional Animal Care and Use Committee (IACUC). Recipient mice (8 weeks old) were rendered diabetic by a single intraperitoneal injection (220 mg/kg) of StreptozotocinŎ (Sigma) dissolved in citrate buffer. Mice received transplants if 2 consecutive non-fasting blood glucose levels of greater than 350 mg/dl were obtained from a whole blood sample.

Islet Isolation

Pancreatic islets of Langerhans (C57BL/6 mice) were provided by the Islet Core Laboratory of the JDRF Center for Islet Transplantation at Harvard Medical School and isolated as described previously (Gotoh et al., Transplantation 40:437–438, 1985).

Syngeneic Marginal Mass Islet Transplantation 250 islets 150–250 îm in diameter were hand-picked using a dissecting microscope. Islets were transplanted under the kidney capsule as described previously (Kaufman et al., J. Exp. Med. 172:291–302, 1990). From each islet preparation the same numbers of control and treatment animals were transplanted.

Graft Functional Outcome Analysis

Graft function was defined as the point when the first of three consecutive days of non-fasting blood glucose levels <200 mg/dl was reached. The primary endpoint of the experiment was defined as time to normoglycemia.

Statistical Analysis

Blood glucose data were summarized as mean±standard deviation of mice receiving untreated or treated islets. Time to recovery of islet function was calculated using Kaplan-Meier life tables and differences between groups tested using a log-rank test, with the three islet preparations treated as separate strata in the analysis, and the median time to recovery, with 95% confidence interval, reported.

TNF-α Induces Apoptosis in βTC3 Cells

Figure 1B:
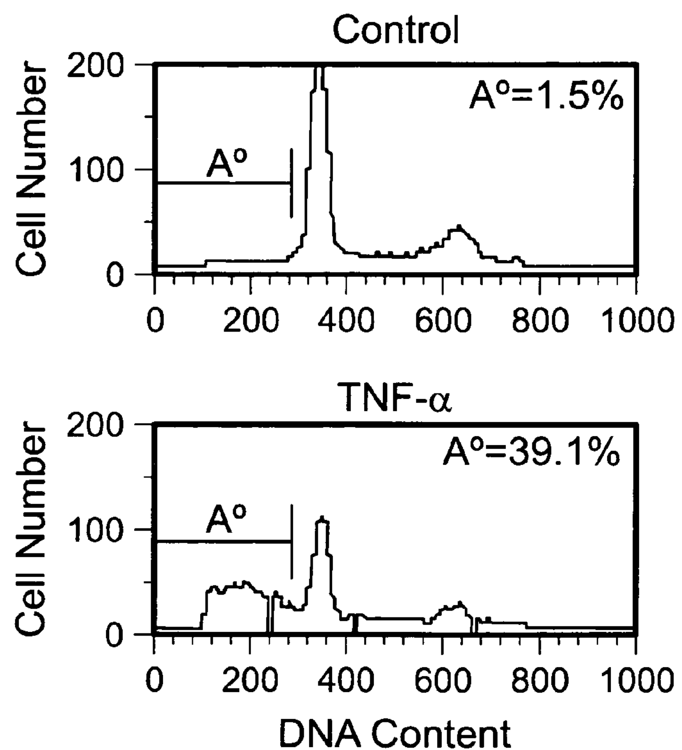
FIG. 1B is a graphical representation illustrating a FACScan™ analysis of DNA fragmentation in βTC3 cells following treatment with TNF-α.
Figure 1C:
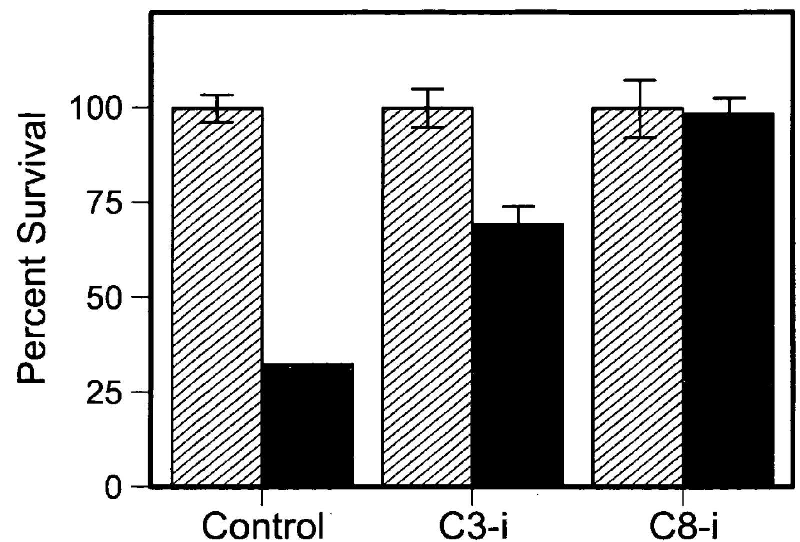
FIG. 1C is a bar graph that illustrates the effect of co-transfecting βTC3 with a β-gal expressing vector (pcDNA3/β-gal) plus control (pcDNA3), and treatment with either the caspase-3 inhibitor Z-DEVD-FMK (C3-i) or the caspase-8 inhibitor IETD-CHO (C8-i). Gray histograms represent untreated β-cells and black histograms represent β-cells treated with TNF-α for 24 hours. Results shown are the mean±standard deviation from duplicate wells taken from one representative experiment out of three.

The effect of TNF-α on βTC3 cells was investigated. The following procedures were utilized to generate the data illustrated in FIGS. 1A–C. FIG. 1A: βTC3 were treated with increasing concentrations of TNF-α. Viable cells were stained 24 hours after activation by crystal violet. The extinction was measured at 562 nm and normalized to untreated cells. FIG. 1B: βTC3 were treated with TNF-α, stained by propidium iodide 24 hours later and analyzed for DNA fragmentation (FACScan™). FIG. 1C: βTC3 were co-transfected with a β-gal expressing vector (pcDNA3/β-gal) plus control (pcDNA3). When indicated, cells were treated with the caspase-3 inhibitor Z-DEVD-FMK (C3-i) or the caspase-8 inhibitor IETD-CHO (C8-i). Gray histograms represent untreated β-cells and black histograms represent β-cells treated with TNF-α for 24 hours. Results shown are the mean±standard deviation from duplicate wells taken from one representative experiment out of three.

TNF-α induced high levels of cell death in the insulinoma cell line βTC3, in a dose-dependent manner (Stephens et al., Endocrinology 140:3219–3227, 1999) (FIG. 1A). DNA fragmentation was demonstrated by propidium iodide (PI) staining (FIG. 1B), suggesting that TNF-α induces β-cell death through apoptosis. TNF-α mediated apoptosis was strictly dependent on the activation of caspase-8 and partially dependent on that of caspase-3, as illustrated by the finding that blocking caspase-8 with a specific caspase-8 inhibitor (IETD-CHO) prevented apoptosis (96% inhibition) while blocking caspase-3 by a specific caspase-3 inhibitor (Z-DEVD-FMK) prevented apoptosis only partially (53% inhibition) (FIG. 1C).

Carbon Monoxide Protects βTC3 Cells

Figure 2A:
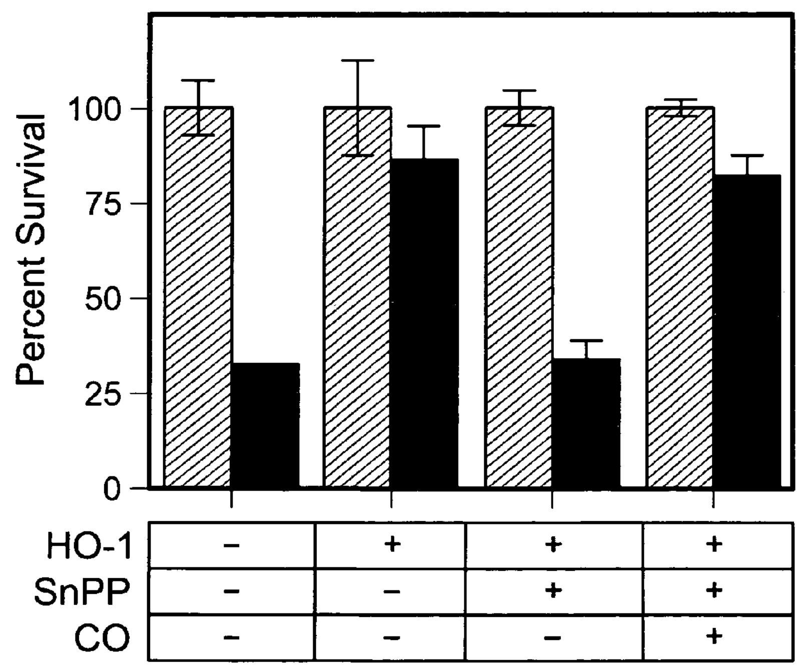
FIG. 2A is a bar graph showing that exogenous carbon monoxide can substitute for HO-1 (hemeoxygenase-1) when HO-1 activity is blocked. Gray histograms represent untreated β-cells and black histograms represent β-cells treated with TNF-α or etoposide or subjected to serum deprivation. Results shown are mean±standard deviation from duplicate wells taken from one representative experiment out of three.
Figure 2B:
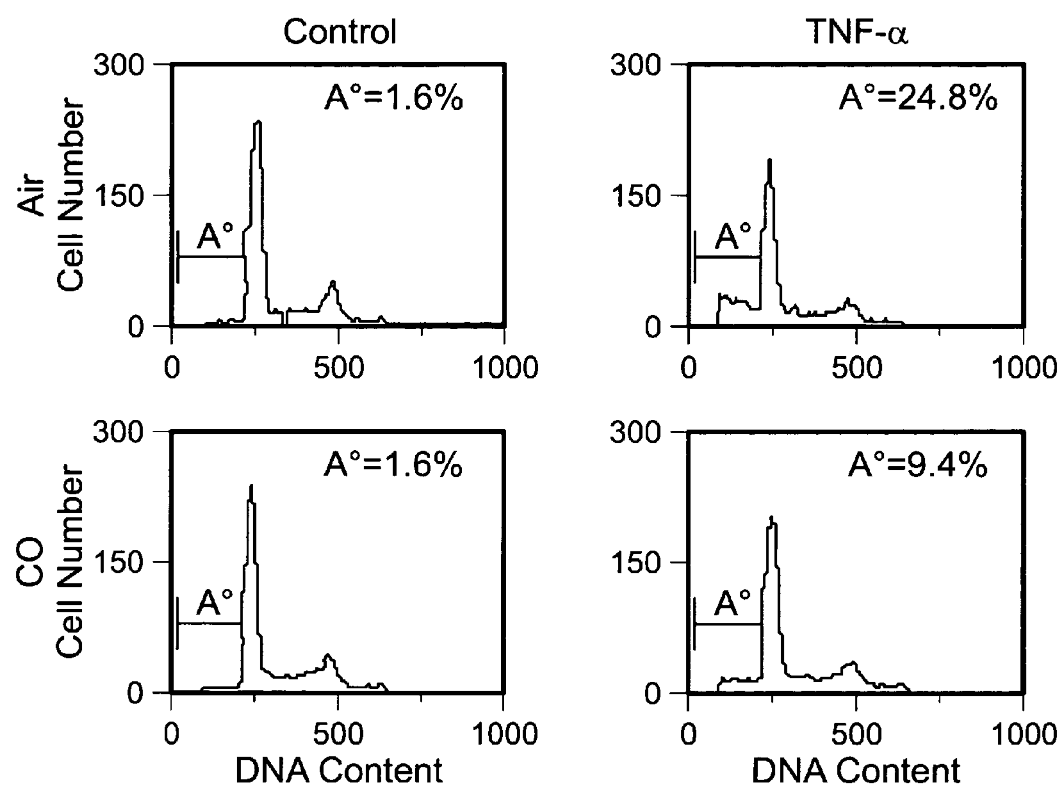
FIG. 2B is a graphical representation of a FACScan™ analysis of DNA fragmentation in βTC3 cells following 24 hour treatment with carbon monoxide after treatment with TNF-α.
Figure 2C:
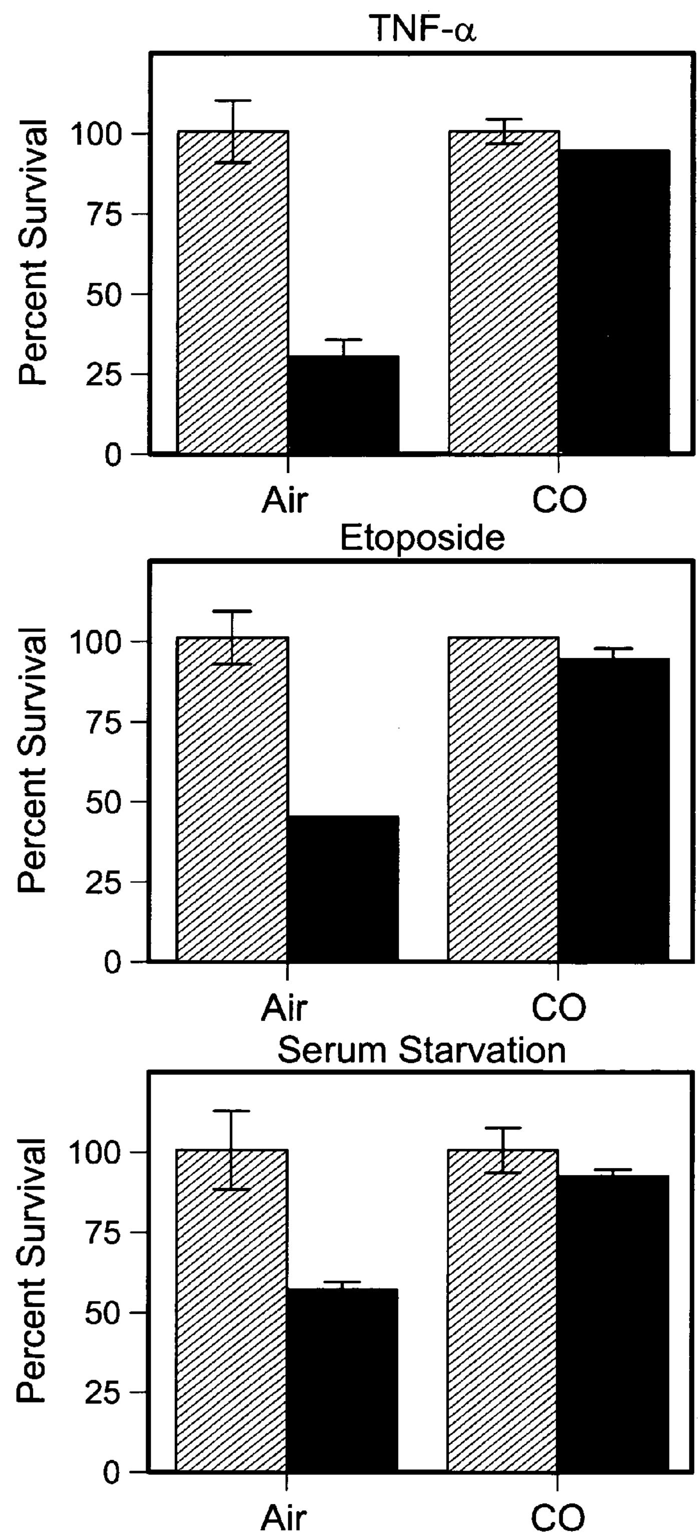
FIG. 2C is a bar graph illustrating that exogenous carbon monoxide protects β-cells from apoptosis in the absence of HO-1. βTC3 cells were transfected with β-gal expressing vectors and were exposed to exogenous carbon monoxide. Gray histograms represent untreated β-cells and black histograms represent β-cells treated with TNF-α or etoposide or subjected to serum deprivation as indicated. Results shown are mean±standard deviation from duplicate wells taken from one representative experiment out of three.

Whether exogenous carbon monoxide could protect β-cells from apoptosis was investigated (FIGS. 2A–C). The following procedures were utilized to generate the data illustrated in FIGS. 2A–C. FIG. 2A: Exogenous CO can substitute for HO-1 when HO-1 activity is blocked. βTC3 were co-transfected with a β-gal expressing vector plus control or HO-1-expressing rector (Brouard et al., J. Exp. Med. 192:1015–1026, 2000). When indicated, HO-1 enzymatic activity was inhibited by tin protoporphyrin (SnPP). When indicated, β-cells were exposed to exogenous carbon monoxide (1%) as described earlier (Otterbein et al., Nature Med. 6:422–428, 2000). Gray histograms represent untreated β-cells and black histograms represent β-cells treated with TNF-α. Results shown are mean±standard deviation from duplicate wells taken from one representative experiment out of three. FIG. 2B: Exogenous carbon monoxide protects β-cells from apoptosis in the DNA fragmentation analysis. βTC3 were treated with TNF-α. Directly after stimulation, βTC3 were exposed to exogenous carbon monoxide for 24 hours. Control βTC3 were treated in the same manner but not exposed to carbon monoxide. After 24 hours cells were stained by propidium iodide and analyzed for DNA fragmentation on a FACScan™. FIG. 2C: Exogenous carbon monoxide protects β-cells from apoptosis in absence of HO-1. βTC3 were transfected with β-gal expressing vectors and were exposed to exogenous carbon monoxide (Stephens et al., Endocrinology 740:3219–27, 1999). Gray histograms represent untreated β-cells and black histograms represent β-cells treated with TNF-α or etoposide or subjected to serum deprivation as indicated. Results shown are mean±standard deviation from duplicate wells taken from one representative experiment out of three.

To evaluate whether expression of HO-1 would protect β-cells from TNF-α mediated apoptosis, βTC3 cells were transiently transfected with a HO-1 expression vector and tested for their ability to survive when exposed to TNF-α. Over-expression of HO-1 protected βTC3 from TNF-α mediated apoptosis (Pileggi et al., Diabetes 50:1983–1991, 2001) (87% survival versus 33% in control) (FIG. 2A). When HO-1 activity was blocked by tin protoporphyrin IX (SnPPIX) (Kappas et al., Hepatology 4:336–341, 1994), the anti-apoptotic effect was suppressed (FIG. 2A), suggesting that the generation of at least one of the end products of heme catabolism by HO-1, i.e. iron, bilirubin and/or CO, is required for its anti-apoptotic function.

On the hypothesis that the anti-apoptotic effect of HO-1 could be mediated by carbon monoxide, whether exposure to exogenous carbon monoxide would substitute for HO-1 in protecting β-cells from apoptosis was tested. When the action of HO-1 was suppressed by SnPPIX, carbon monoxide exposure suppressed TNF-α mediated apoptosis to a similar extent as HO-1 (FIG. 2A). Exposure to exogenous carbon monoxide alone was protective (11.7% apoptotic cells versus 20.3% in controls not exposed to CO), as demonstrated by DNA fragmentation analysis (FIG. 2B). Similarly, β-cell apoptosis induced by etoposide or serum starvation was suppressed by carbon monoxide exposure (FIG. 2C).

Induction of HO-1 in Donors and Recipients Leads to Prolonged Islet Graft Survival Whether induction of HO-1 in donors and recipients would protect islet cell grafts was investigated. The following procedures were utilized to generate the data illustrated in Table 1, below. A mouse model was utilized for the experiments. Donors of islet cells were treated with cobalt protoporphyrin (CoPP) (20 mg/kg) once per day before islet cell isolation. Recipients of islet cell grafts were treated with CoPP (20 mg/kg) once per day on days 1, 3, 5, 7 or with CoPP (10 mg/kg) once per day on days 1, 3, 5, 7, 9, 11, 13, 15, and 17. Treatment with CoPP induces expression of heme oxygenase-1 (HO-1).

TABLE I

Induction of HO-1 in Donors and Recipients Leads to Prolonged Islet Graft Survival

| Treatment | No. of Islets | Rejection day | Mean ± SD | Rejection/ Total |
|---|---|---|---|---|
| CoPP 20 mg/ kg × 5 | 350–400 | 17, 33, 33, 48 >58 × 2, >67 × 1 | 44.85 ± 17.81 | 4/7 |
| CoPP 10 mg/ kg × 10 | 350–400 | 30, 30, >51 × 2 | 40.5 ± 12.12 | 2/4 |
| Control | 350–400 | 8, 8, 15, 15, 16, 22, 26 | 15.71 ± 6.65 | 7/7 |

Listed under "rejection day" are the days to which islets survived. For instance, ">51×2", means that islets in 2 recipients were still surviving after 51 days. The mean date of rejection is shown in the fourth column. These data demonstrate that induction of HO-1 results in longer survival of islets after transplantation.

Exogenous Carbon Monoxide Protects Murine Islet Cells from Apoptosis

Figure 3:
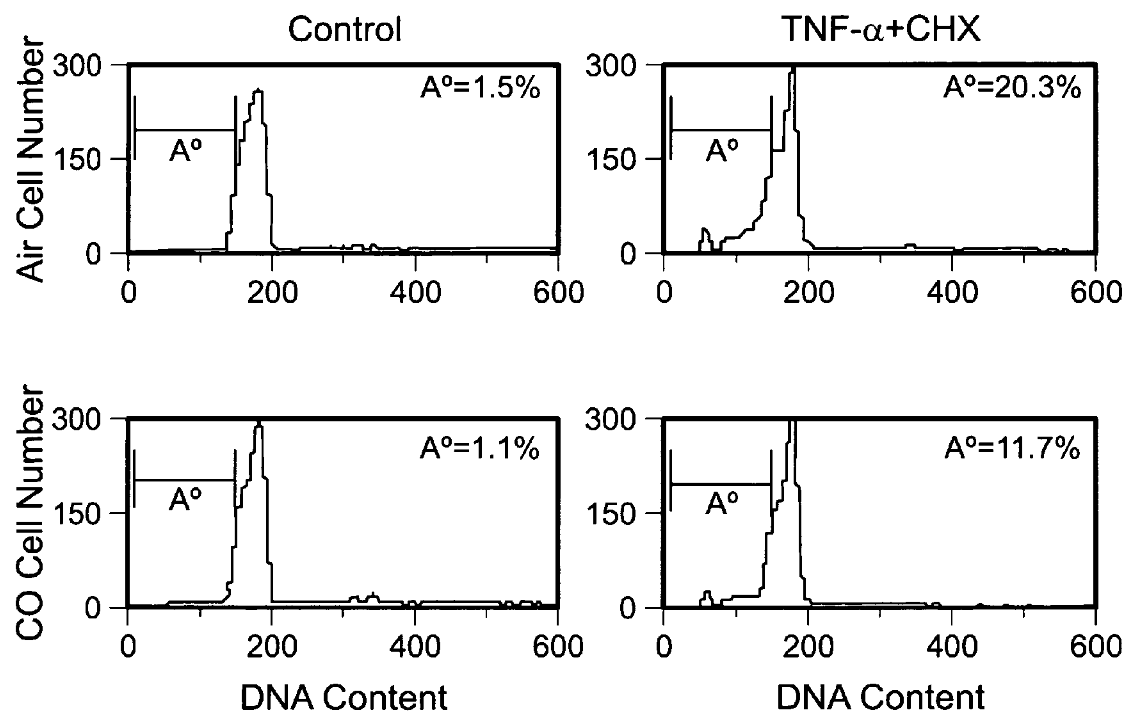
FIG. 3 is a DNA fragmentation analysis by FACScan™ that indicates that exogenous carbon monoxide protects murine islets of Langerhans from apoptosis. CHX=cycloheximide.

Whether exogenous carbon monoxide protects murine islet cells from apoptosis was also investigated (FIG. 3). The following procedures were utilized to generate the data illustrated in FIG. 3. Apoptosis was induced in freshly isolated murine islets (C57BL/6) by stimulation with TNF-α and cycloheximide (CHX). Directly after stimulation, islets were exposed to exogenous carbon monoxide for 24 hours. Control islets were treated in the same manner but not exposed to carbon monoxide. After 48 hours cells were analyzed on a FACScan™ for DNA fragmentation. This experiment was done twice with indistinguishable results.

Exposure to carbon monoxide for 24 hours protected isolated murine (C57/BL6) islets of Langerhans from TNF-α plus cycloheximide (CHX) mediated apoptosis (11.7% apoptotic cells versus 20.3% in controls not exposed to CO) as assayed by DNA fragmentation analysis (FIG. 3).

The Anti-apoptotic Effect of Exogenous Carbon Monoxide is Mediated by Guanylate Cyclase Activation and Signals Through cGMP-dependant Protein Kinases (cGK)

Figure 4A:
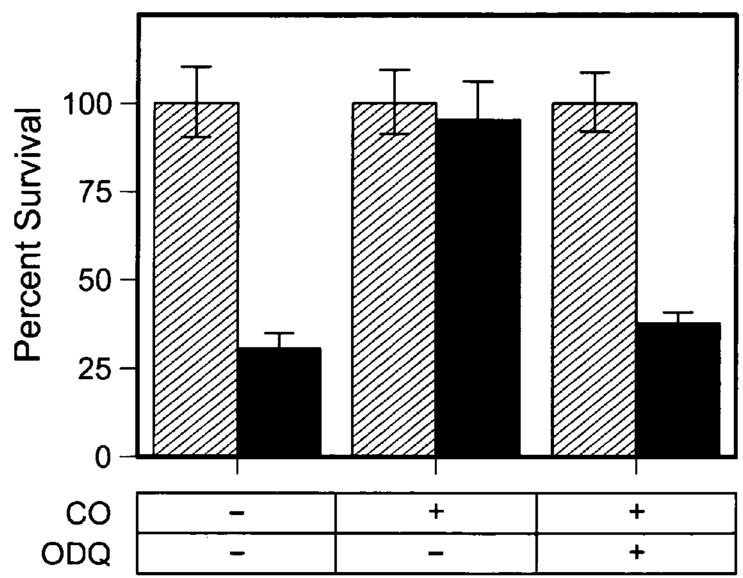
FIG. 4A is a bar graph illustrating that the anti-apoptotic effect of exogenous carbon monoxide is mediated by guanylate cyclase activation. ODQ=guanylyl cyclase inhibitor ODQ.
Figure 4B:
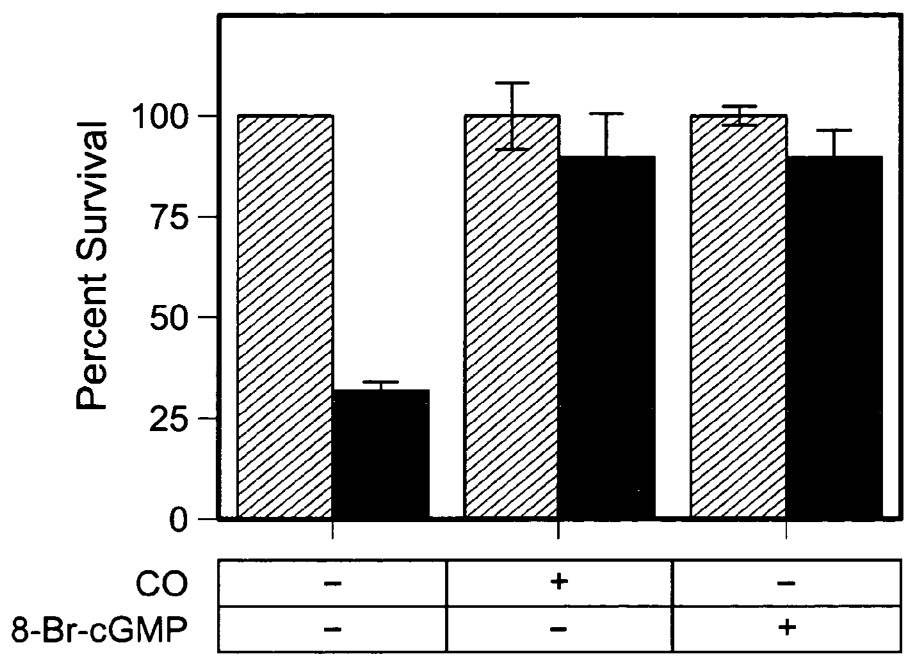
FIG. 4B is a bar graph illustrating that cGMP analogue can substitute for carbon monoxide in protecting cells from apoptosis. 8-Br-cGMP=cGMP analogue 8-Br-cGMP.
Figure 4C:
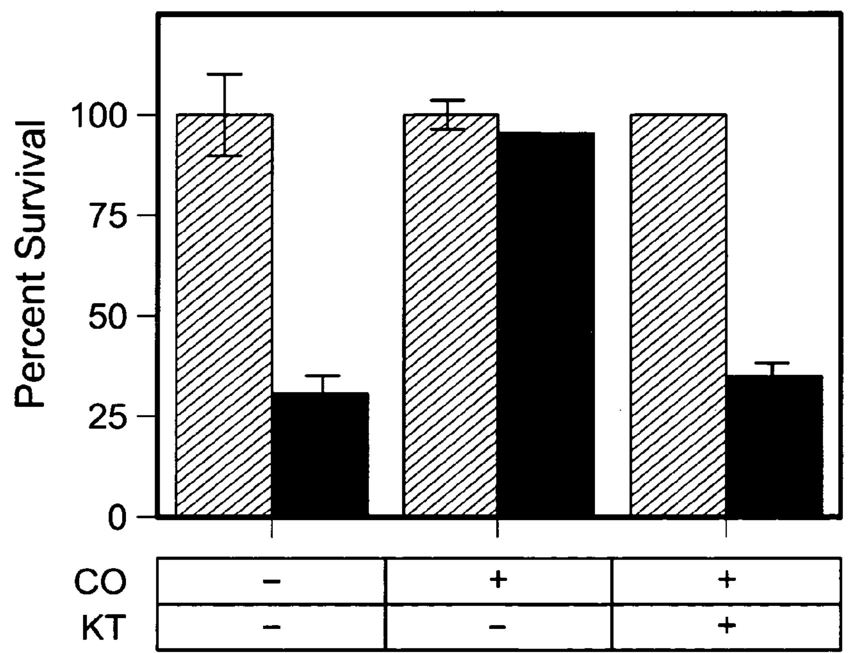
FIG. 4C is a bar graph illustrating that cGMP-dependent protein kinases (cGK) mediate the anti-apoptotic effect of carbon monoxide. βTC3 cells were co-transfected with β-gal expressing vector. For FIGS. 4A–C, gray histograms represent untreated β-cells and black histograms represent β-cells treated with TNF-α. Results shown are mean±standard deviation from duplicate wells taken from one representative experiment out of three. KT=protein kinase G inhibitor KT5823.

Whether the anti-apoptotic effect of carbon monoxide acted via activation of soluble guanylate cyclase (sGC) and generation of cGMP was investigated (FIGS. 4A–C). The following procedures were utilized to generate the data illustrated in FIGS. 4A–C. FIG. 4A: The anti-apoptotic effect of exogenous carbon monoxide is mediated by guanylate cyclase activation. βTC3 were transfected with β-gal expressing vectors and exposed to exogenous carbon monoxide (1%). Where indicated, βTC3 were treated with the guanylyl cyclase inhibitor ODQ. FIG. 4B: A cGMP analogue can substitute for carbon monoxide in protecting from apoptosis. βTC3 were transfected with β-gal expressing vectors. Where indicated, βTC3 were exposed to exogenous carbon monoxide. Where indicated, βTC3 were treated with the cGMP analogue 8-Br-cGMP but not exposed to carbon monoxide. FIG. 4C: cGMP-dependent protein kinases (cGK) mediate the anti-apoptotic effect of carbon monoxide. βTC3 were co-transfected with β-gal expressing vector. When indicated, βTC3 were exposed to exogenous carbon monoxide. When indicated, cells were treated with the protein kinase G inhibitor KT5823 (KT). Gray histograms represent untreated β-cells and black histograms represent β-cells treated with TNF-α. Results shown are mean±standard deviation from duplicate wells taken from one representative experiment out of three.

Whether the anti-apoptotic effect of carbon monoxide acted via activation of soluble guanylate cyclase and generation of cGMP (as described in fibroblasts) was investigated (Petrache et al., Am. J. Physiol. Lung Cell Mol. Physiol. 278:L312–319, 2000). Inhibition of sGC activity by oxadiazoloquinoxalin (ODQ) suppressed the anti-apoptotic effect of CO, suggesting that a soluble guanylate cyclase is a major mediator for carbon monoxide in this experimental system (FIG. 4A). The cGK activator/cGMP analogue, 8-Br-cGMP, suppressed βTC3 apoptosis to an extent similar to that seen with carbon monoxide (FIG. 4B). Also, inhibition of cGMP-dependent protein kinases by the specific inhibitor KT5823 suppressed the anti-apoptotic effect of exogenous carbon monoxide (FIG. 4C), suggesting that the anti-apoptotic effect of carbon monoxide is mediated through the activation of one or several cGMP-dependent protein kinases.

Figure 5A:
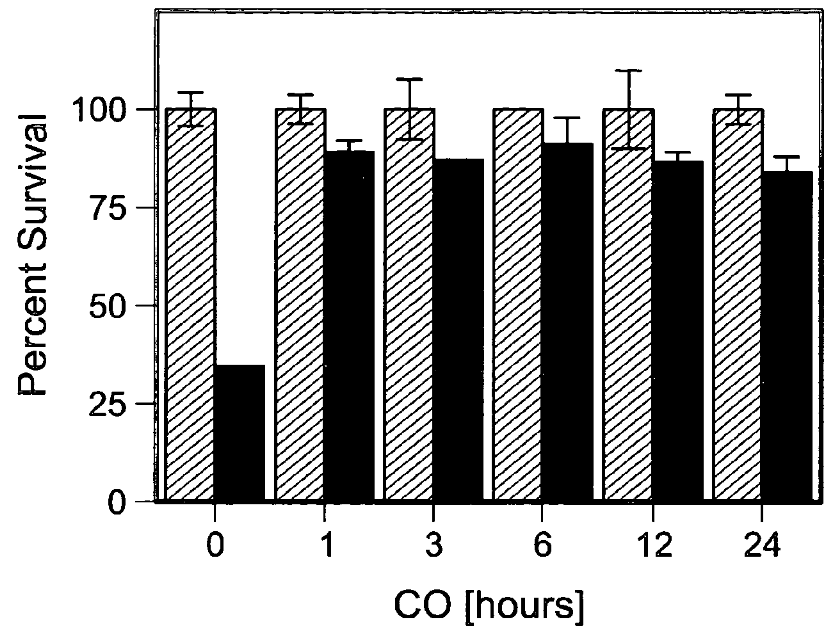
FIG. 5A is a bar graph showing that one hour of carbon monoxide exposure is sufficient to prevent apoptosis.
Figure 5B:
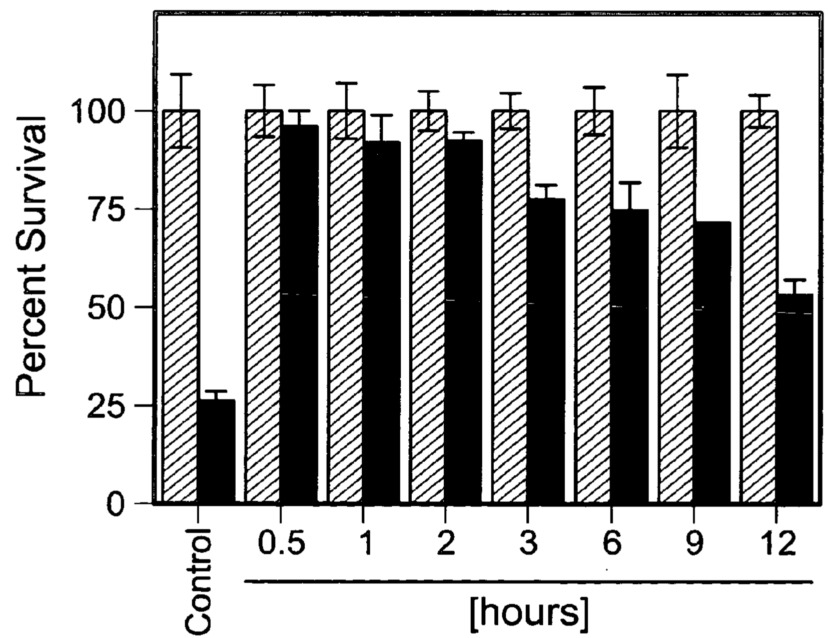
FIG. 5B is a bar graph showing that carbon monoxide protects β-cells after induction of apoptosis.
Figure 5C:
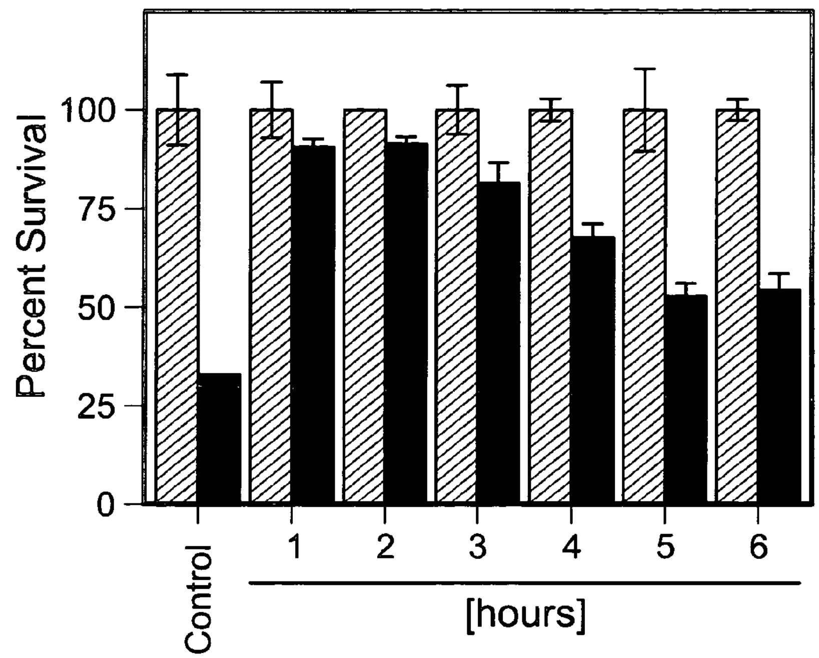
FIG. 5C is a bar graph showing that preincubation with carbon monoxide prevents β-cell apoptosis. For FIGS. 5A–C, gray histograms represent untreated β-cells and black histograms represent β-cells treated with TNF-α. Results shown are mean±standard deviation from duplicate wells taken from one representative experiment out of three.

Exogenous Carbon Monoxide Provided Anti-apoptotic Protection Under Various Protocols The ability of carbon monoxide to protect β-cells after induction of apoptosis was investigated (FIGS. 5A–C). The following procedures were utilized to generate the data illustrated in FIGS. 5A–C. FIG. 5A: one hour of carbon monoxide exposure is sufficient to prevent apoptosis. βTC3 were transfected with β-gal expressing vectors. Apoptosis of β-cells was induced by TNF-α. Immediately after TNF-α activation, cells were exposed to 1% carbon monoxide for varying periods (0–24 hours). Control βTC3 were treated in the same manner but were not exposed to carbon monoxide. Cell survival was determined 24 hours after application of TNF-α. FIG. 5B: carbon monoxide protects β-cells after induction of apoptosis. βTC3 were transfected with β-gal expressing vectors. Apoptosis was induced by TNF-α. After varying periods (0.5–12 hours, as indicated), βTC3 were exposed to 1% carbon monoxide (Otterbein et al., Nat. Med, 6:422–428, 2000). Control βTC3 were treated in the same manner but were not exposed to carbon monoxide. Cell survival was determined 24 hours after application of TNF-α. FIG. 5C: Preincubation with carbon monoxide prevents β-cell apoptosis. βTC3 were transfected with β-gal expressing vectors and apoptosis was induced by TNF-α. βTC3 were pre-exposed to 1% carbon monoxide for one hour. Control βTC3 were treated in the same manner but were not exposed to carbon monoxide. 1–6 hours after termination of the pre-exposure, apoptosis was induced by TNF-α. Gray histograms represent untreated β-cells and black histograms represent β-cells treated with TNF-α. Results shown are mean±standard deviation from duplicate wells taken from one representative experiment out of three.

βTC3 were exposed to carbon monoxide for different time periods (1–24 hours) immediately after the addition of TNF-α and tested for apoptosis 24 hours later. One hour of carbon monoxide exposure was sufficient to prevent β-cell apoptosis (FIG. 5A).

To investigate whether carbon monoxide exposure can block ongoing apoptosis, β-cells were exposed for one hour to CO, 0.5 to 12 hours after induction of apoptosis by TNF-β. Even when exposed two hours after TNF-α stimulation, carbon monoxide was still able to suppress β-cell apoptosis (FIG. 5B).

To investigate whether pre-incubation with carbon monoxide would protect β-cells from apoptosis, βTC3 were exposed to carbon monoxide for 0.5 to 3 hours before apoptosis induction. One hour pre-incubation in the presence of carbon monoxide was sufficient to prevent β-cell apoptosis (data not shown). To evaluate for how long this effect would last when the time between pre-incubation and the apoptotic stimulus was extended, β-cells were preexposed for one hour to CO, one to six hours before induction of apoptosis with TNF-α (FIG. 5C). One hour of pre-incubation with carbon monoxide prevented β-cell apoptosis in cells stimulated with TNF-α even two to three hours after the end of the one-hour treatment with carbon monoxide. These data indicate that relatively brief treatment with carbon monoxide can act in an anti-apoptotic manner and that this anti-apoptotic effect will last for an extended time period.

Exposure of Murine Islets to Carbon Monoxide Improves Islet Survival/Function Following Transplantation To determine whether carbon monoxide could also improve islet graft function in vivo, a marginal islet mass of 250 handpicked islets was transplanted in a syngeneic system, a model for primary non-function (Berney et al., Transplantation 71:125–32, 2001); Kaufman et al., Diabetes 43:778–83, 1994). Transplantation of a marginal (e.g., sub-optimal) number of islets (a "marginal mass") into a diabetic syngeneic recipient causes a delay in the return to normoglycemia without the effects of rejection or recurrence of auto-immune disease. In determining what would be a marginal islet mass in the C57/BL6 syngeneic system, it was observed that transplantation of 500 handpicked islets under the kidney capsule of the recipient led to rapid return to normoglycemia (1.5±0.5 days (n=4)) whereas transplantation of 250 islets resulted in a significant delay (14.2±2.94 days (n=9)). Thus 250 islets were defined as a marginal mass. Using a marginal mass in this manner does not involve rejection or recurrence of auto-immune disease (Berney et al., Transplantation 71:125–132, 2000).

Figure 6A:
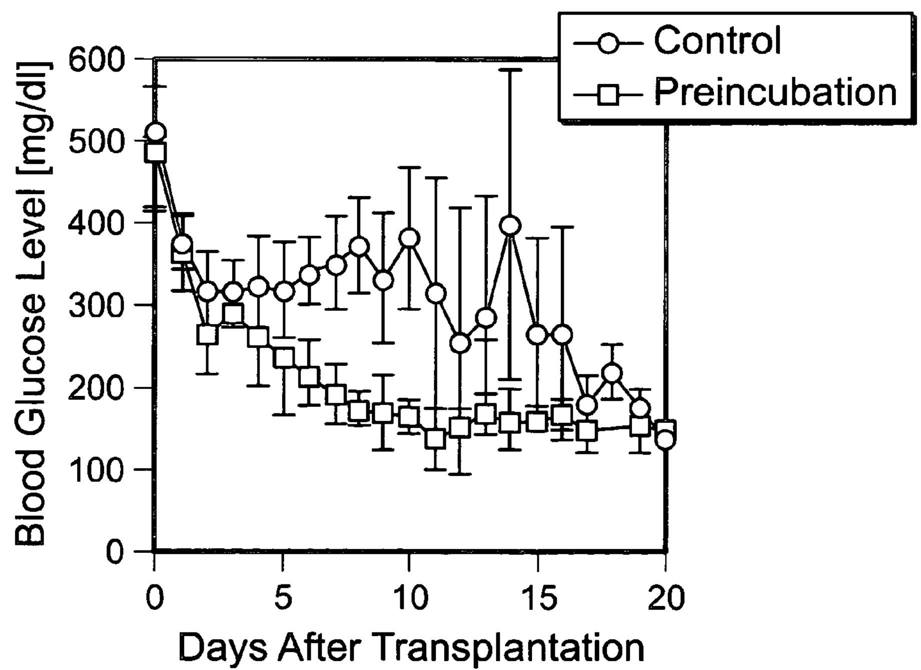
FIG. 6A is a line graph indicating that exposure of murine islets to carbon monoxide improves survival and function following transplantation.
Figure 6B:
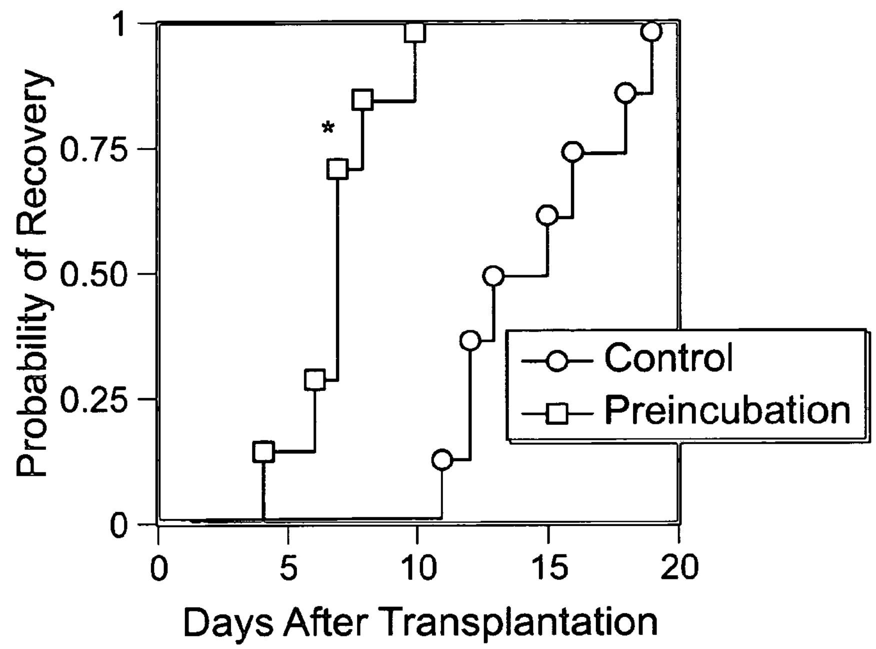
FIG. 6B is a line graph that indicates the probability of recovery (blood glucose level below 200 mg/dl) for animals receiving islets pre-exposed to carbon monoxide or control islets. *P=0.001 versus control.

Whether carbon monoxide pre-incubation of islet grafts prior to transplantation results in better functional performance in vivo was investigated (FIGS. 6A–B). The following procedures were utilized to generate the data illustrated in FIGS. 6A–B. FIG. 6A: Two hundred and fifty freshly isolated and hand-picked islets from C57BL/6 mice were incubated in medium pre-saturated with 1% carbon monoxide for two hours at 37° C. Control islets were treated in the same manner but were not exposed to carbon monoxide. The islets were transplanted under the kidney capsule of the diabetic syngeneic recipients as described previously. After transplantation, blood glucose levels were determined on a daily basis. A total of 16 animals (8 with pre-exposed islets; 8 controls) were transplanted. One animal receiving pre-exposed islets died on day 3 of non-exposure related technical reasons and was included in the statistical analysis as censored animal. The primary endpoint of these experiments was the first day of normoglycemia. Data are shown as mean±standard deviations. FIG. 6B: indicates the probability of recovery (blood glucose level below 200 mg/dl) for animals receiving islets pre-exposed to carbon monoxide or control islets. *P=0.001 versus control.

Based on the observation that the effects of carbon monoxide treatment last for an extended time period (FIGS. 5A and B) and that relatively brief pre-treatment with carbon monoxide (before the apoptotic stimulus is applied) is anti-apoptotic (FIG. 5C), whether pre-exposure of islets to carbon monoxide can improve islet survival and/or function following transplantation was evaluated. A marginal islet mass was transplanted under the kidney capsule of diabetic syngeneic recipients. The time needed to reach normoglycemia was reduced in a highly significant manner (P=0.0011) when islets were pre-incubated for two hours in medium pre-saturated with carbon monoxide (7 days, 95% confidence interval: 6–8 days) as compared to control islets not pre-exposed to carbon monoxide (14 days, 95% confidence interval 12–18 days) (FIG. 6). In total, three different islet preparations were used for these experiments. There was no statistically significant difference in the time to normoglycemia for islets among these three preparations (P>0.25).

Carbon Monoxide Exposures

For cell culture experiments, 5% $CO_2$ is present for buffering requirements. CO at a concentration of 1% (10,000 ppm) in compressed air is mixed with compressed air with or without $CO_2$ in a stainless steel mixing cylinder before delivery into the exposure chamber. Flow into the 3.70-$ft^2$ plexiglass animal chamber is maintained at 12 L/min and into the 1.2-$ft^2$ cell culture chamber at a flow of 2 L/min. The cell culture chamber is humidified and maintained at 37° C. A CO analyzer (Interscan, Chatsworth, Calif.) is used to measure CO levels continuously in the chambers. Gas samples were taken by the analyzer through a port in the top of the chambers at a rate of 1 L/min and analyzed by electrochemical detection, with a sensitivity of 10–600 ppm. Concentration levels are measured hourly. There are no fluctuations in the CO concentrations once the chamber had equilibrated (approximately 5 min).

Animals are exposed to >98% $O_2$ or 98% $O_2$+CO mixtures at a flow rate of 12 liters/min in a 3.70-cubic-foot glass exposure chamber. Animals are supplied food and water during the exposures. CO at a concentration of 1% (10,000 ppm) in compressed air is mixed with >98% $O_2$ in a stainless steel mixing cylinder prior to entering the exposure chamber. By varying the flow rates of CO into the mixing cylinder, concentrations delivered to the exposure chamber are controlled. Because the flow rate was primarily determined by the $O_2$ flow, only the CO flow was changed to generate the different concentrations delivered to the exposure chamber. $O_2$ concentrations in the chamber are determined using a gas spectrometer.

Cell Isolation Procedure

The following example illustrates a protocol used for the isolation of islet cells from rats or mice. One bottle of Rat LiberaseǑ (from Boehringer Manheim/Roche cat. # 1 815 032) was dissolved in 4 ml of sterile HBSS, chilled on ice for 30 min, aliquoted into 0.5 ml aliquots, and stored at −20° C. To each 0.5 ml aliquot, 33 ml of medium, e.g., M199, HBSS or RPMI 1640 without calf serum, was added.

Rats were overdosed with anesthesia (0.1 ml plus 0.1 ml/100 g body weight of Nembutol I.P.). For mice, 3 ml syringes were prepared with 2 ml of Liberase solution with a 27 g-needle bent at a 90-degree angle. For the surgery, 2 pairs of scissors were used; one large pair for the abdominal cut and one fine pair to snip the bile duct. Two pairs of forceps were used for excision of the pancreas. One hemostat was used to clamp off the bile duct.

The abdomen was opened and the pancreas was exposed as much as possible by making a v cut from the lower abdomen. The pancreatic duct was clamped off (with a hemostat in rats or a small bulldog clamp in mice) at its duodenal insertion, taking care not to injure the surrounding pancreatic tissue. The bile duct was isolated at the proximal end. Fat was removed before inserting the cannula, making sure not to puncture the portal vein. The duct was cut with the fine scissors one third of the way across and the cannula was inserted in the duct. The cannula was held in the duct by clamping the duct lightly with forceps. LiberaseǑ solution was injected rapidly. The pancreas appeared to be distended and fully dilated after 6 mls of fluid injection. In mice, the needle was inserted into the duct as proximal to the liver as possible and LiberaseǑ solution was injected. The rat or mouse was then sacrificed by cutting the diaphragm and heart or aorta.

After LiberaseǑ infiltration, the pancreas was removed, starting by removing from the intestines, then the stomach and then the spleen. When the pancreas was attached only by the bile duct, it was cut out of the rat. The pancreas was placed in a 50 ml conical tube, and placed in a water bath at 37° C. for 30 min.

Following incubation, 20 ml of medium+NCS were added to each tube. The remainder of the isolation was completed on ice. Tubes were shaken by hand vigorously for 5–10 seconds to break up the tissue. The islets were washed several times to remove the LiberaseǑ in a clinical centrifuge at 800 rpm (approx. 180×g) for 120 sec or 1200 rpm (approx. 200×g) for 90 sec. The supernatant was poured off and 25–35 ml of medium was added and vortexed gently (about ½ max.). The centrifugation step was repeated, followed by washing 2–3 times. The tissue was resuspended in 20 ml of medium, and the suspension was filtered through a 400 îm diameter wire mesh (Thomas scientific mesh 35 cat. # 8321-M22) to remove the remaining undigested tissue, fat and lymph. 5–10 ml more was added to the tube to wash any remaining islets off and filter through the mesh.

The cells were pelleted by spinning at 1200 rpm for 90 sec. The supernatant was removed, leaving as little excess medium as possible.

To make the gradient, the pellet was resuspended in 10–15 ml Histopaque 1077Ǒ (Sigma cat # H 1077) and vortexed until the suspension was homogeneous (same as for washes). 10 ml of medium was overlaid, without NCS, being careful to maintain the sharp interface between the HistopaqueÒ and the medium. The medium was added by pipetting slowly down the side of the tube. The gradient was centrifuged for 20 minutes at 2400 rpm (900 g) at 10° C. with very slow acceleration and no braking.

Following centrifugation, the islet layer was collected from the interface with a disposable 10 cc serologic pipette (Falcon), and placed in 50 cc conical tubes. Islets were washed several times to remove the HistopaqueÒ by adding 25–35 ml of the medium+NCS. The initial centifugation was performed at 1200 rpm for 2 min., but the subsequent centrifugations were performed for 90 sec. After the 3 washes, the islets were resuspended by pipetting up and down. 7–10 ml each were put on 60 mm sterile culture dishes for hand picking.

Hand picking of islet cells was performed using a 100 îl sterile pipette tip, under a microscope. Each islet was picked individually, and care was taken to avoid all other tissue. Only those islets between 50 and 225 îm in diameter exhibiting a smooth and round or oval shape were picked.

EXAMPLE II

Carbon Monoxide Suppresses the Rejection of Mouse-to-Rat Cardiac Transplants

Animals

BALB/c mouse hearts were used as donor organs for transplantation into inbred adult male Lewis rats (Harlan Sprague-Dawley, Indianapolis, Ind.). Animals were housed in accordance with guidelines from the American Association for Laboratory Animal Care, and research protocols were approved by the Institutional Animal Care and Use Committees of the Beth Israel Deaconess Medical Center.

Surgical Model

Animals were anesthetized by a combination of methoxyflurane (Pitman-Moore, Mundelain, Ill.) inhalation and pentobarbital (Abbott, North Chicago, Ill.) at a dose of 30–50 mg/kg i.p. during all procedures. Heterotopic cardiac transplants were performed as described previously (Berk et al., Physiol Rev. 8:999–1030, 2001; Petkova et al., J Biol. Chem. 276:7932–7936, 2001). Graft survival was assessed daily by palpation. Rejection was diagnosed by cessation of ventricular contractions and confirmed by histologic examination.

Experimental Reagents

Cobra venom factor (CVF; which blocks complement activation) (Quidel, San Diego, Calif.) was administered i.p. on day −1 (60 U/kg) and on day 0 (20 U/kg) with respect to the day of transplantation (day 0). Cyclosporin A (CsA; Novartis, Basel, Switzerland), which blocks T cell activation, was administered i.m. (15 mg/kg) starting at day 0 and daily thereafter until the end of each experiment. Tin protoporphyrin (SnPPIX), cobalt protoporphyrin (CoP-PIX), and iron protoporphyrin (FePPIX; Porphyrin Products, Logan, Utah) were diluted in 100 mM NaOH to a stock solution of 50 mM and kept at −70° C. until used. Light exposure was limited as much as possible. Both SnPPIX and FePPIX were administered i.p. (30 μM/kg) in PBS. FePPIX and SnPPIX were administered to the donor at days −2 and −1 (30 μM/kg) and to the recipient at the time of transplantation (day 0) and daily thereafter (30 μM/kg).

CO Exposure

Briefly, CO at a concentration of 1% (10,000 parts per million; ppm) in compressed air was mixed with balanced air (21% oxygen) in a stainless steel mixing cylinder before entering the exposure chamber. CO concentrations were controlled by varying the flow rates of CO in a mixing cylinder before delivery to the chamber. Because the flow rate is primarily determined by the $O_2$ flow, only the CO flow was changed to deliver the final concentration to the exposure chamber. A CO analyzer (Interscan Corporation, Chatsworth, Calif.) was used to measure CO levels continuously in the chamber. Graft donors were placed in the CO exposure chamber 2 days before transplantation. Graft recipients were placed in the exposure chamber immediately following transplantation and were kept in the exposure chamber for 14 (n=3) or 16 (n=3) days. CO concentration was maintained between 250 and 400 ppm at all times. Animals were removed daily from the chamber to assess graft survival and to administer CsA, SnPPIX, or FePPIX, as described above.

HO Enzymatic Activity

HO enzymatic activity was measured by bilirubin generation in heart and liver microsomes. Animals were sacrificed, and the liver and hearts were flushed with ice-cold PBS and frozen at −70° C. until used. Organs were homogenized in four volumes of sucrose (250 mM) Tris-HCl (10 mM/L) buffer (pH 7.4) on ice and centrifuged (28,000 RPM 3×, 20 min, 4° C.). The supernatant was centrifuged (105,000 RPM 3×, 60 min, 4° C.), and the microsomal pellet was resuspended in $MgCl_2$ (2 mM)-potassium phosphate (100 mM) buffer (pH 7.4) and sonicated on ice. The samples (1 mg of protein) were added to the reaction mixture (400 îl) containing rat liver cytosol (2 mg of protein), hemin (50 îM), glucose-6-phosphate (2 mM), glucose-6-phosphate dehydrogenase (0.25 U), and NADPH (0.8 mM) for 60 min at 37° C. in the dark. The formed bilirubin was extracted with chloroform and, OD was measured at 464–530 nm (extinction coefficient, 40 mM/cm for bilirubin). Enzyme activity is expressed as picomoles of bilirubin formed per milligram of protein per 60 min (pmol/mg/h). The protein concentration was determined by the bicinchoninic acid protein assay (Pierce, Georgetown). The background was ~5 pmol/mg/h. All reagents used in this assay were purchased from Sigma (St. Louis, Mo.), unless otherwise indicated. Carboxyhemoglobin was measured 2 days after transplantation by using a Corning 865 blood gas analyzer (Clinical Chemistry, Massachusetts General Hospital, Boston, Mass.).

Histomorphometric Analysis

Grafts were harvested 3 days after transplantation, embedded in paraffin, fixed in formalin, and serially sectioned (5 îm) in toto from the apex to the base. Ten sections were placed per slide in a total of about 20–25 slides. Every fifth slide was stained with hematoxylin and eosin (H&E) for histomorphometric analysis. Two images per slide were captured by using a Nikon Eclipse E600Ò microscope (Nikon, Melville, N.Y.) connected to a Hitachi 3-CCD Color Camera (model HV-C20; Hitachi, Tokyo, Japan) and to a Power MacintoshÒ 7300/200 computer (Apple Computer, Cupertino, Calif.) equipped with IPLab Spectrum digital imaging software (Signal Analytics Corporation, Vienna, Va.). About 50 images were captured from each transplanted heart from two to three animals per group. Images were analyzed by manual segmentation, tracing the infarcted and noninfarcted areas from the right and left ventricles in each section. Areas corresponding to infarcted and noninfarcted tissue were calculated by digital imaging software as number of pixels corresponding to those areas. Infarcted and noninfarcted areas were then calculated as percentage of total area. Pooled data for each group, expressed as area in pixels or as percentage of infarction, was analyzed by using ANOVA. Results obtained in this manner were similar whether using either pixels or percentage of infarction and only the results obtained using percentage of infarction are shown (see Table II). Results are expressed as mean=SD.

Immunohistology

Grafts were harvested 3 days after transplantation, snap-frozen in liquid nitrogen, and stored at −80° C. Cryostat sections were fixed and stained as described previously (Soares et al, Nature Med. 4:1073, 1998). Rat leukocyte populations were analyzed by using anti-rat leukocyte common Ag (LCA, CD45; OX-1), Éé TCR (TCRÉé-chains; R73), B cell (CD45RB; OX-33), NK cell (NKR-P1; 3.2.3), and MΦ (CD68; ED-1), mAbs (Serotec, Harlan Bioproducts for Science, Indianapolis, Ind.). Detection of fibrin/fibrinogen was conducted by using a rabbit anti-human fibrin/fibrinogen polyclonal Ab (Dako, Carpinteria, Calif.). Intragraft complement activation was detected by using an anti-rat Clq (The Binding Site, Birmigham, U. K.), C3 (ED11; Serotec), or C5b-9 mAb (Dako). Rat IgM was detected by using the mouse anti-rat IgM mAb MARM-4 (a kind gift of Dr. H. Bazin, University of Louvain, Brussels, Belgium). Isotype-matched mAbs or purified Ig, as well as a control for residual endogenous peroxidase activity, were included in each experiment. Detection of apoptosis was carried out by using ApopTagŎ in situ apoptosis detection kit (Oncor, Gaithersburg, Md.) according to the manufacturer's instructions.

Complement Hemolytic Assay (CH50)

CH50 units were defined as the dilution of rat serum required to produce 50% maximal lysis of Ab-sensitized sheep erythrocytes. Briefly, Ab-sensitized sheep erythrocytes ($1\times10^8$ cells/ml; Sigma) were incubated (30 min, 37° C.) with rat serum in gelatin Veronal buffer (GVB$^{++}$; Sigma). Cells were centrifuged and hemoglobin release was measured (1 Î=550 nm). Background was measured in the absence of sheep erythrocytes or in the absence of serum and subtracted from all samples.

Cellular ELISA

Serum levels of rat anti-mouse Abs were measured by cellular-based indirect ELISA. The mouse 2F–2B endothelial cell line (CRL-2168; American Type Culture Collection (ATCC), Manassas, Va.) was used as an antigenic target. Briefly, 2F–2B cells were cultured in DMEM (Life Technologies, Rockville, Md.), 10% FCS, 100 U/ml penicillin, and 100 îg/ml streptomycin (Life Technologies). Glutaraldehyde-fixed 2F–2B cells were incubated (1 h, 37° C.) in the presence of rat serum serially diluted in PBS 0.05% Tween 20 (Sigma) and rat anti-mouse Abs were detected by using mouse anti-rat IgM (MARM-4), IgG1 (MARG1-2), IgG2a (Marg2a-1), IgG2b (MARGb-8), or IgG2c (MARG2c-5) (kind gifts from Prof. H. Bazin, University of Louvain, Brussels, Belgium). Mouse anti-rat Abs were detected by using HRP-labeled goat anti-mouse Fab' depleted of anti-rat Ig cross reactivity (0.1 îg/ml, 1 h, room temperature; Pierce, Rockford, Ill.). HRP was revealed by using ortho-phenyldiamine (Sigma) and $H_2O_2$ (0.03%) in citrate buffer (pH 4.9). Absorbance was measured at Î=490 nm. The relative amount of circulating anti-graft Abs in the serum was expressed as OD (Î=490) taken from one serial dilution in the linear range of the assay (1:32–1:1024).

Binding of rat C3 to mouse endothelial cells was measured by a modified cellular ELISA with mouse 2F–2B endothelial cells as antigenic targets (Miyatake et al, J. Immunol. 160:4114, 1998). Briefly, nonfixed 2F–2B endothelial cells were incubated in the presence of rat serum serially diluted in GVB$^{++}$ buffer (1 h, 37° C.). Cells were fixed in PBS, 0.05% glutaraldehyde, and rat C3 deposition was detected by using a mouse anti-rat C3 mAb (Serotec).

Platelet Aggregation Assay

Mouse 2F–2B endothelial cells were cultured on 0.2% gelatin (Sigma) coated six-well plates in 88% DMEM (Life Technologies), 10% FCS (FCS), 100 U/ml penicillin, and 100 îg/ml streptomycin (Life Technologies). Confluent endothelial cells either were left untreated or were treated with the HO-inducing agent CoPPIX (50 îM; 18 h), the HO inhibitor SnPPIX (50 îM, 18 h), or both CoPPIX (50 îM, 15 h) and SnPPIX (50 îM, 3 h). Platelet-rich plasma was obtained by centrifugation (290-g, 12 min, 19° C.) of normal rat plasma in 3.8% sodium citrate. Rat platelets ($3–10^8$ cells ml) were resuspended in HT buffer (8.9 mM $NaHCO_3$, 0.8 mM $KH_2PO$, 5.6 mM dextrose, 2.8 mM KCl solution, 0.8 mM $MgCl_2$, 129 mM NaCl, 10 mM HEPES). Platelets were overlaid (5 min; 37° C.) on mouse endothelial cells, and platelet aggregation assays were conducted as described before (Kaczmarek et al, J. Biol. Chem. 271:33116, 1996) by using an aggregometer (Chrono-Log, Harestown, Pa.) and ADP (0.5–4 μM) as an agonist.

Cell Extracts and Western Blot Analysis

Endothelial cells were washed in PBS (pH 7.2), harvested by scraping, and lysed in Laemmli buffer. Electrophoresis was conducted under denaturing conditions with 10% polyacrylamide gels. Proteins were transferred onto a polyvinyldifluoridine membrane (immobilon P; Millipore, Bedford, Mass.) by electroblotting and detected with rabbit polyclonal Abs directed against human HO-1 or HO-2 (StressGen, Victoria, Canada) or é-tubulin (Boehringer Mannheim, Mannheim, Germany). Proteins were visualized by using HRP-conjugated donkey anti-rabbit IgG or goat anti-mouse IgG (Pierce) and the ECL assay (Amersham Life Science, Arlington Heights, Ill.) according to manufacturer's instructions.

Transient Transfections and Apoptosis Assay

The murine 2F–2B endothelial cell line (ATCC) was transiently transfected as described elsewhere (Soares et al., Nature Med. 4:1073, 1998; Brouard et al, J. Exp. Med. 192:1015, 2000). All experiments were conducted 24–48 h after transfection. é-galactosidase-transfected cells were detected as described elsewhere (Soares et al., Nature Med. 4:1073, 1998; Brouard et al., J. Exp. Med. 192:1015, 2000). Percentage of viable cells was assessed by evaluating the number of é-galactosidase-expressing cells that retained normal morphology as described elsewhere (Soares et al., Nature Med. 4:1073, 1998; Brouard et al., J. Exp. Med. 192:1015, 2000). The number of random fields counted was determined to have a minimum of 200 viable transfected cells per control well. The percentage of viable cells was normalized for each DNA preparation to the number of transfected cells counted in the absence of the apoptosis-inducing agent (100% viability). All experiments were performed at least three times in duplicate. Actinomycin D (Act. D; Sigma) was dissolved in PBS and added to the culture medium (10 îg/ml) 24 h after transfection. SnPPIX (Porphyrin Products) was dissolved (10 îM) in 100 mM NaOH and conserved at −20° C. until used. SNPPIX was added to the culture medium (50 îM) 6 h after transfection. Human recombinant TNF-α (R&D Systems, Minneapolis, Minn.) was dissolved in PBS, 1% BSA, and added to the culture medium (10–100 ng/ml) 24 h after transfection.

Exposure of Cultured Endothelial Cells to CO

Cells were exposed to compressed air or varying concentration of CO (250 and 10,000 ppm), as described elsewhere (Otterbein et al., Nature Med. 6:422, 2000; and Brouard et al., J. Exp. Med. 192:1015, 2000).

Aortic Transplant Model

Aortic transplantation was carried out done as described elsewhere (Plissonnier et al., Transplantation 60:414–424, 1995). Briefly, the aorta and the inferior vena cava were cut to be bled after heparinization. After additional left thoracotomy, three or four pairs of the inter-costal arteries were ligated using 7-0 nylon suture (Keisei Medical Industrial Co., LTD, Tokyo, Japan), and 2 cm of the descending aorta was harvested. The graft was inserted between the renal arteries and the aortic bifurcation by standard microsurgery technique using 9-0 Nylon sutures (Ethilon™, Ethicon, Inc, Somerville, N.J.). The native abdominal aorta was left after both edges were ligated.

CO at a concentration of 1% (10,000 parts per million; ppm) in compressed air was mixed with balanced air (21% oxygen) as described previously (Otterbein et al., Am J Physiol 276(4 Pt 1):L688–L694, 1999). For the transplant model, graft donors were placed in the CO chamber two days before transplantation. Recipients were placed in the chamber immediately following transplantation and kept there 56 days. CO concentration was maintained at 250 ppm at all times.

Adult male (250–350 g) Brown Norway rats (RT1 were used as aortic graft donors and adult male (250–350 g) Lewis rats (RT1) as recipients (Charles River Lab. Wilmington, Mass.). Male C57BL/6, $p21^{-/-}$ and $p53^{-/-}$ null mice were purchased from Jackson Laboratory (Bar Harbor, Me.). The $MKK3^{(-/-)}$ null mice were generated as previously described (Lu et al., EMBO. J. 18:1845–1857, 1999). Mice were allowed to acclimate for one week with rodent chow and water ad libitum.

RT-PCR

RT-PCR was conducted after RNA isolation from the transplanted hearts by using an RNA extracting kit, according to the manufacturer's instructions (Qiagen, Chatsworth, Calif.). Primers used for mouse β-actin were: sense (5'-3'), CCTGACCGAGCGTGGCTACAGC (SEQ ID NO:1); antisense (3'-5'), AGCCTCCAGGGCATCGGAC (SEQ ID NO:2); and for mouse HO-1: sense (5'-3'), TCCCAGACACCGCTCCTCCAG (SEQ ID NO:3); antisense (3'-5'), GGATTTGGGGCTGCTGGTTTC (SEQ ID NO:4).

Enzymatic Activity is Critical to Suppress Acute Vascular Rejection

Figure 7:
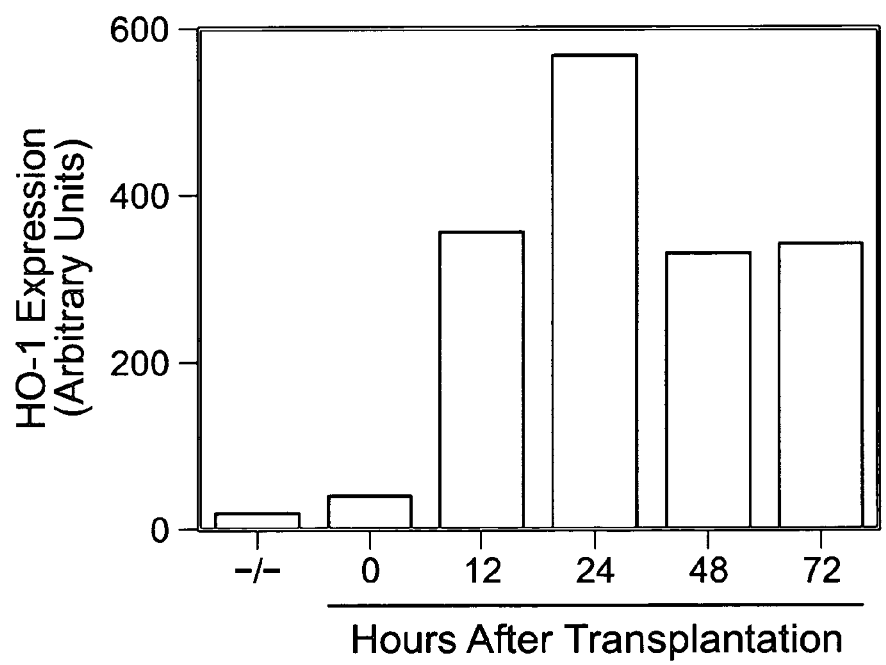
FIG. 7 is a bar graph that illustrates expression of HO-1 in mouse hearts transplanted into CVF plus CsA-treated rats. Mouse hearts were transplanted into rats treated at the time of transplantation with cobra venom factor (CVF) plus daily treatments after transplantation with cyclosporin A (CsA). Expression of HO-1 and β-actin mRNA were detected by RT-PCR. The symbol −/− indicates RNA from HO-1 −/− mouse hearts used as a negative control. Histograms represent relative level of HO-1 mRNA expression normalized for expression of mactin mRNA.

Mouse hearts transplanted into untreated rats underwent acute vascular rejection 2–3 days after transplantation, an observation consistent with previous reports (Soares et al., Nature Med. 4:1073, 1998; and Koyamada et al., Transplantation 65:1210, 1998). Under cobra venom factor (CVF) plus cyclosporin A (CsA) treatment, mouse cardiac grafts survived long term (see Table II, below), a finding also consistent with previous reports. Under CVF plus CsA treatment, graft survival was associated with up-regulation of HO-1 expression by graft endothelial and smooth muscle cells as well as by cardiac myocytes (FIG. 7). Expression of HO-1 mRNA was detected by RT-PCR 12–24 h after transplantation and HO-1 protein 24–72 h after transplantation (FIG. 7). Long-term graft survival did not occur when the HO inhibitor SnPPIX was administered to the donor and then to the recipient, despite treatment with CVF plus CsA. Under these conditions, all grafts were rejected in 3–7 days (Table II). Control treatment with FePPIX, a protoporphyrin that does not inhibit HO activity, did not lead to graft rejection (Table II).

TABLE II

Inhibition of HO-1 activity by SnPPIX precipitates graft rejection.

| Treatment | Survival Time |
| --- | --- |
| CVF + CsA | >50 (n = 8) |
| CVF + CsA + FePPIX | >50 (n = 4) |
| CVF + CsA + SnPPIX | 3, 4, 5 (n = 2); 6 (n = 4); 7 (n = 2) |

To generate the data in Table II, mouse hearts were transplanted into CVF plus CsA-treated rats. Graft recipients were treated with FePPIX or SnPPIX. Treatment with SnPPIX induced graft rejection 3–7 days after transplantation ($p<0.0001$ as compared to rats treated with CVF plus CsA alone or with CVF plus CsA plus FePPIX). Statistical analyses were carried out using Fisher's exact test.

Figure 8:
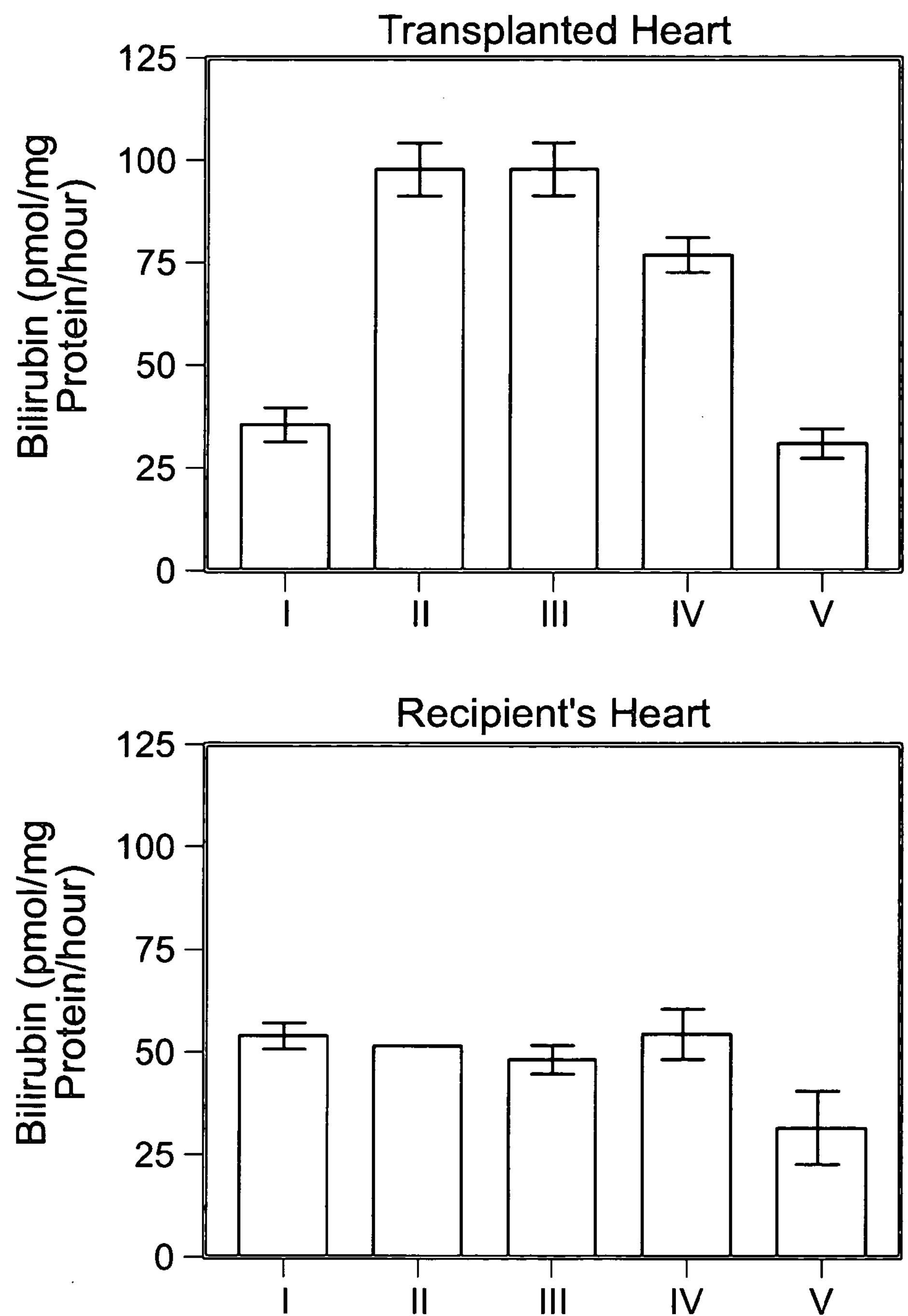
FIG. 8 is a set of bar graphs illustrating that SnPPIX inhibits HO-1 enzymatic activity in vivo. Mouse hearts were transplanted into untreated rats (II) or into rats treated with, CVF and CsA (III) plus FePPIX (IV) or SnPPIX (V). Total HO activity in donor and recipient hearts was measured 2 days after transplantation and compared with basal HO activity in normal mouse and rat hearts, respectively (I). Results shown are the mean±standard deviation (SD) of three animals analyzed for each treatment. Statistical analyses were conducted by using unpaired Welsh t test.

To demonstrate that SnPPIX, but not FePPIX, blocked HO-1 function in vivo, total HO enzymatic activity was quantified in transplanted and recipient hearts 2 days after transplantation (FIG. 8). Naive mouse hearts produced 35.5±4 picomols of bilirubin per milligram of total protein per hour (pmol/mg/h; FIG. 8). HO activity was significantly increased in mouse hearts transplanted into untreated (98±7.21 pmol/mg/h; $p=0.001$), CVF plus CsA-treated (98.3±7.23 pmol/mg/h), or CVF plus CsA plus FePPIX-treated (77.3±5.51 pmol/mg/h; $p=0.0009$) rats, as compared with naive hearts (FIG. 8). HO activity was inhibited to basal levels, as present in naive hearts, in mouse hearts transplanted into rats treated with CVF plus CsA plus SnPPIX (32.37±7.23 pmol/ mg/h). This represented a highly significant inhibition as compared with mouse hearts transplanted into untreated ($p=0.0009$), CVF plus CsA-treated ($p=0.0009$), or CVF plus CsA plus FePPIX-treated rats ($p=0.0018$; FIG. 8). HO activity in the recipient's livers was also up-regulated after transplantation in a manner that mimicked that of the transplanted hearts (data not shown). However, this was not the case for the recipient's own heart, in which HO activity was not up-regulated following transplantation (FIG. 8). In grafts transplanted into SnPPIX-treated rats, there was progressive myocardial infarction, which became apparent as early as 2 days after transplantation (data not shown). This was not observed in grafts transplanted into control rats treated with FePPIX (data not shown).

Figure 9:
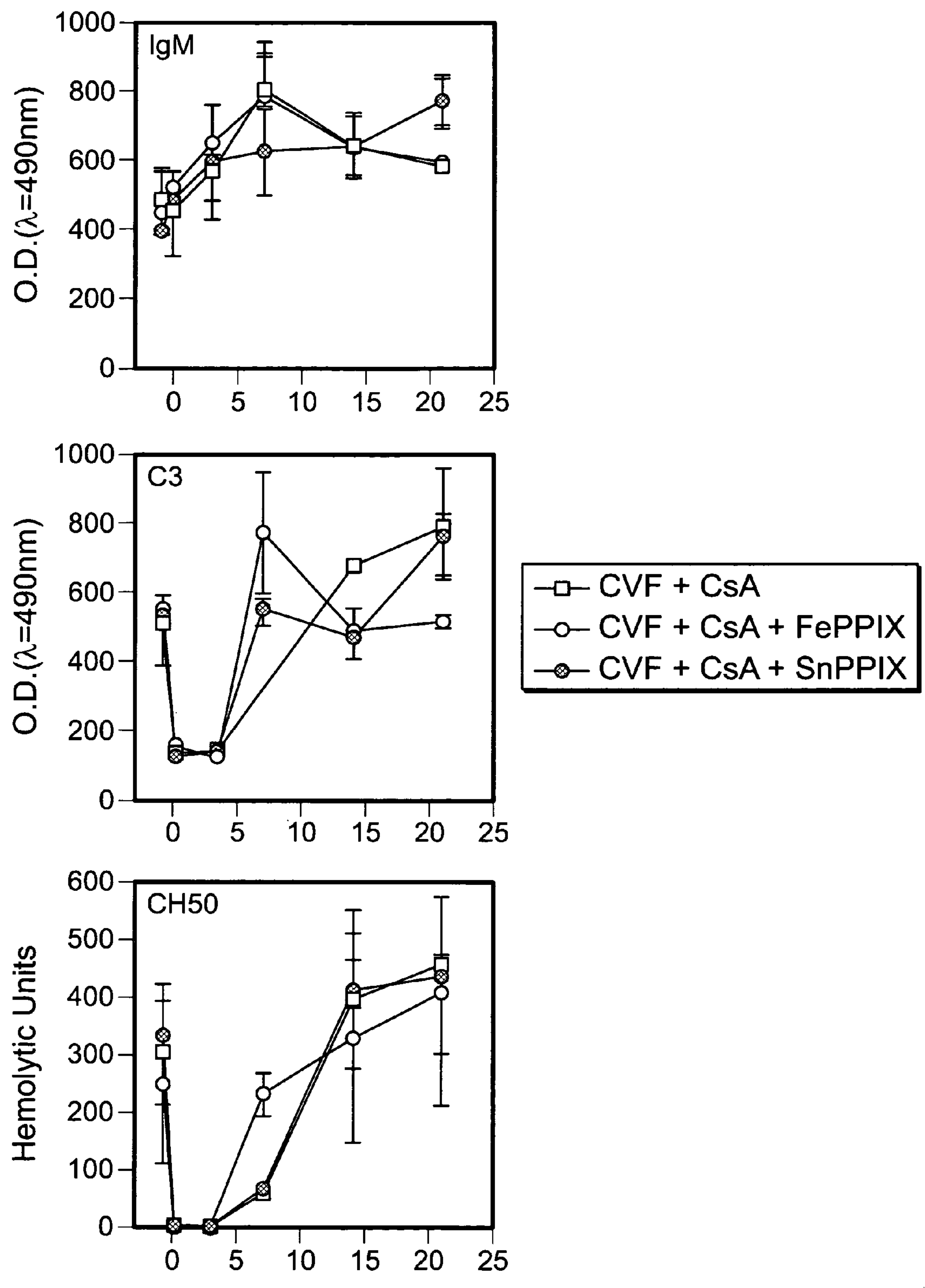
FIG. 9 is a set of line graphs illustrating that SnPPIX and FePPIX do not interfere with the generation of anti-graft antibodies (Abs). Mouse hearts were transplanted into rats treated with CVF plus CsA, as described above. Serum level of anti-graft IgM Abs was evaluated by a cellular ELISA. Binding of rat complement component C3 to mouse endothelial cells was evaluated by cellular ELISA. Complement hemolytic activity (CH50) was evaluated by a standard hemolytic assay. Results shown are the mean±SD (n=3).

It has previously been shown that rats that receive a mouse cardiac graft under CVF plus CsA treatment generate anti-mouse Abs that are exclusively of the IgM isotype (Koyamada et al., Transplantation 65:1210, 1998). Additional treatment with SNPPIX or FePPIX did not influence this Ab response (FIG. 9). Generation of antigraft Abs was correlated with complement activation, as demonstrated by C3 deposition on mouse endothelial cells (FIG. 9). Neither SnPPIX or FePPIX treatment influenced C3 deposition on mouse endothelial cells (FIG. 9).

Exogenous CO Fully Substitutes for HO-1 Enzymatic Activity in Suppressing Acute Vascular Rejection All mouse hearts transplanted into rats treated with SnPPIX and exposed to CO (400 ppm; 0.04%) survived long term (see Table III, below). The dose of CO used (400–500 ppm) corresponds to approximately one-twentieth of the lethal dose (data not shown). Rats and mice exposed to CO did not exhibit untoward reactions. CO exposure was discontinued 14 (n=3) or 16 (n=3) days after transplantation without influencing graft survival, i.e., grafts continued to function for >50 days (Table III).

TABLE III

Exogenous CO fully substitutes for HO-1 in suppressing graft rejection

| Treatment | Survival Time (days) |
|---|---|
| CVF + CsA + SnPPIX | 3, 4, 5, (n = 2); 6 (n = 4); 7 (n = 2) |
| CVF + CsA + SnPPIX + CO | >50 (n = 6) |

To generate the data in Table III, mouse hearts were transplanted into CVF plus CsA-treated rats. When indicated, graft recipients were treated with SNPPIX with or without exposure to CO. Graft rejection observed in SnPPIX-treated rats was suppressed under exposure to exogenous CO ($p<0.0001$ as compared to recipients treated with CVF plus CsA plus SnPPIX). Statistical analyses were carried out using Fisher's exact test.

Figure 10A:
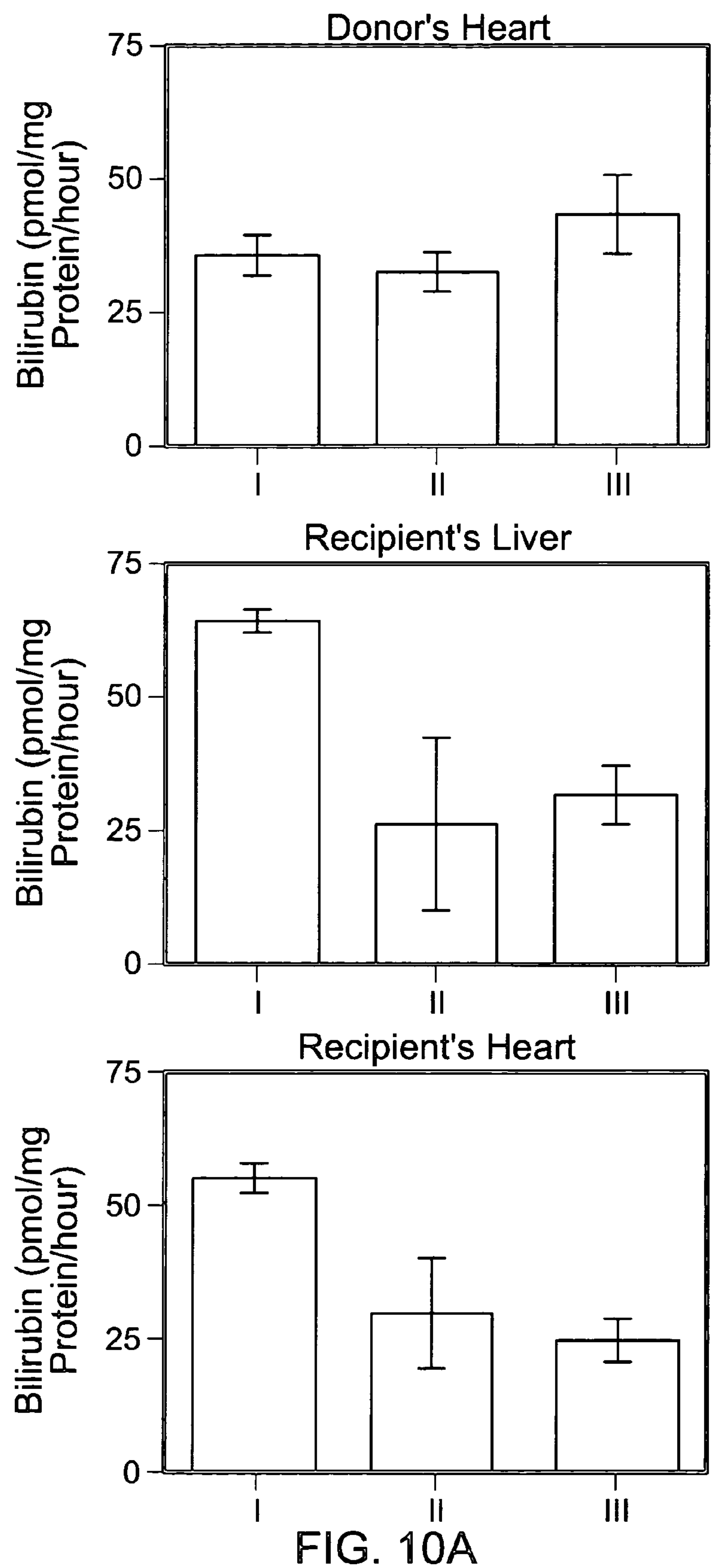
FIG. 10A is a set of bar graphs illustrating that exogenous CO does not affect the ability of SnPPIX to suppress HO-1 enzymatic activity. Mouse hearts were transplanted into rats treated with CVF plus CsA plus SnPPIX (II) or SNPPIX and CO (III). Total HO activity was measured in donors' and recipients' hearts as well as in recipients' livers 2 days after transplantation. HO activity in different specimens was compared with basal HO activity in normal mouse hearts (I), rat hearts (I), or livers (I), according to the sample analyzed. Results shown are the mean ±SD of three animals analyzed for each treatment. Statistical analyses were conducted by using unpaired Welsh t test.
Figure 10B:
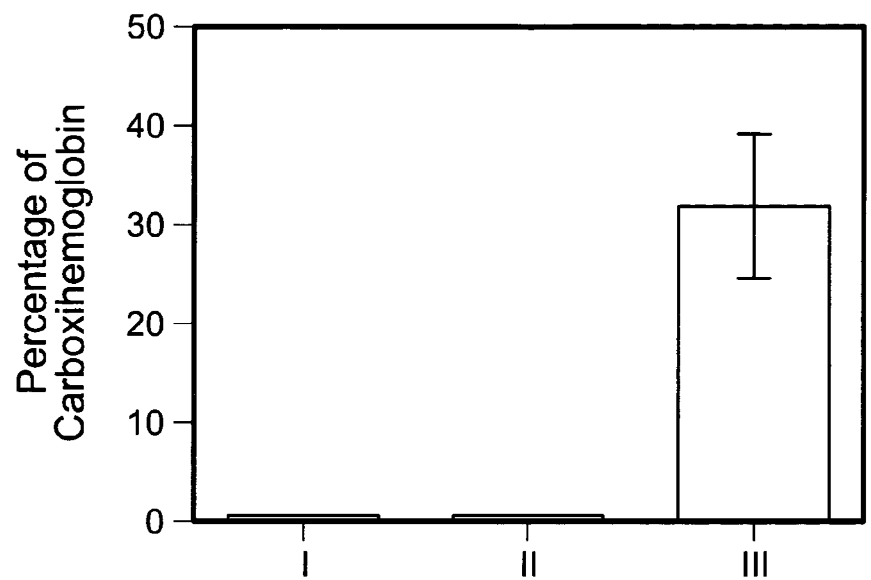
FIG. 10B is a bar graph that illustrates that exogenous CO does not affect the ability of SnPPIX to suppress HO-1 activity. The animals used to generate the data of FIG. 10A were analyzed for carboxyhemoglobin content 2 days after transplantation. Results shown are the mean±SD (n=3).

To determine whether exogenous CO interfered with inhibition of HO-1 enzymatic activity by SnPPLX, which could account for the ability of CO to suppress graft rejection, it was investigated whether CO affected HO enzymatic activity in hearts transplanted into SnPPIX-treated rats. As shown in FIG. 10, this was not the case. Total HO enzymatic activity in hearts transplanted under SnPPIX treatment (32.37±7.23 pmol/mg/h) was not significantly different from that of hearts transplanted into rats treated with SnPPIX and exposed to CO (43.6±7.57 pmol/mg/h; p=0.1095; FIG. 10). Similar results were obtained in the recipient's livers and hearts (FIG. 10).

Exogenous CO may substitute for HO-1 activity in preventing graft rejection. This might work by a mechanism that involves "loading" of exogenous CO by inhalation into RBC and then delivery through the circulation into the graft at an adequate concentration. According to this theory, when endogenous HO-1 activity is being inhibited by SnPPIX, exogenous CO would mimic the effect of endogenous CO that is produced when HO-1 enzymatic activity is not impaired. Exposure of the transplant recipient to 400 ppm of exogenous CO increased carboxyl hemoglobin from 0.5±1.5% to 32.1±6.9% (FIG. 10). The fact that the transplanted hearts survived in animals exposed to CO, even under these suppressive effects of SnPPIX, may indicate that this level of CO was sufficient to adequately "charge" RBC, deliver CO into the graft, and suppress graft rejection (FIG. 10). Alternatively, carbon monoxide may be delivered to the graft, and all tissues of the body, dissolved in plasma.

Whether exogenous CO suppressed the development of myocardial infarction that characterizes graft rejection in SnPPIX-treated rats was investigated. Grafts were harvested 3 days after transplantation and quantified for the percentage of infarcted area. Hearts transplanted into untreated rats showed nearly complete transmural infarction of the right ventricle (87.1±4.9% of the right ventricle area) with extensive endomyocardial and transmural infarction of the left ventricle (32.0±6.7% of the left ventricle area; data not shown). Infarctions showed nonviable eosinophic myocardium lacking nuclei with interstitial hemorrhage, edema, and neutrophils. Left ventricle infarctions were always endomyocardial with transmural extension depending on the degree of infarction, and those in the right ventricle were more diffuse in origin. The percentage of infarcted area in both ventricles generally increased from the apex to the base of the heart. Hearts transplanted into CVF plus CsA-treated rats showed only small, diffuse, nontransmural areas of infarction in the right (4.5±4.9%) but not in the left (0.7±2.1%) ventricle (see Table IV, below). Hearts transplanted into CVF plus CsA plus FePPIX-treated rats showed small diffuse areas of infarction in the right (12.2±9.5%) but not in the left (0.7±1.3%) ventricle (Table IV). These hearts were indistinguishable from those transplanted into CVF plus CsA treated rats without FePPIX treatment (data not shown). Hearts transplanted into CVF plus CsA plus SnPPIX-treated rats showed significant transmural right ventricular infarctions (26.1±12.7%) with extensive endomyocardial and transmural left ventricular infarctions (37.6±15.5%) (Table IV) in a pattern that was indistinguishable from that of hearts transplanted into untreated rats (data not shown). These lesions were specific to the transplanted heart. The recipients' native hearts did not develop any infarction. The percentage of infarcted area in hearts transplanted into SnPPIX-treated rats was significantly higher ($p<0.001$) as compared with that of hearts transplanted into rats treated with CVF plus CsA with or without FePPIX treatment (Table IV). Hearts transplanted into SnPPIX treated rats that received exogenous CO showed very little infarction of the right (8.4±5.3%) and left (1.8±3.4%) ventricles (Table IV), with patterns that were similar to those of hearts transplanted into CVF plus CsA-treated rats with or without FePPIX treatment (data not shown). The percentage of infarcted area in hearts transplanted into SnPPIX-treated rats that received exogenous CO was not significantly different from that of hearts transplanted into CVF plus CsA-treated rats with or without FePPIX treatment. However, the percentage of infarcted area in these hearts was significantly different ($p<0.001$) from that of hearts transplanted under the same treatment but that did not receive exogenous CO.

TABLE IV

Morphometric analysis

| Treatment | Right Ventricle | Left Ventricle |
|---|---|---|
| CVF + CsA | 4.5 ± 4.9 | 0.7 ± 2.1 |
| CVF + CsA + FePPIX | 12.2 ± 9.5 | 0.7 ± 1.3 |
| CVF + CsA + SnPPIX | 26.1 ± 12.7* | 37.6 ± 15.5* |
| CVF + CsA + SnPPIX + CO | 8.4 ± 5.3 | 1.8 ± 3.4 |

To generate the data in Table IV, mouse hearts were transplanted into (n=3 per group) CVF plus CsA-treated rats. When indicated, graft recipients were treated with FePPIX or SnPPIX and exposed to CO. Results are shown as percentage of infarcted area. Statistical analyses were carried out using ANOVA test. An asterisk indicates significant difference as compared to all other treatments.

Exogenous CO Suppresses Vascular Thrombosis and Monocyte/Macrophage Infiltration that Characterize Acute Vascular Rejection Mouse hearts were transplanted into CVF plus CsA-treated rats. SnPPIX or FePPIX was administered and graft recipients were exposed to CO (250–400 ppm). Grafts were harvested 3 days after transplantation (n=3 per group) and stained for rat IgM, rat and mouse complement C1q, rat and mouse P-selectin, rat and mouse fibrin/fibrinogen, and rat CD45 expressing leukocytes. Mouse hearts transplanted into CVF plus CsA-treated rats with or without FePPIX treatment showed extensive intravascular deposition of rat IgM and C1q (data not shown) but no detectable IgG, C3, or C5b-9 (data not shown). HO-2, HO-1, and ferritin were detected in graft endothelial and smooth muscle cells as well as in cardiac myocytes (data not shown). There was only minimal vascular thrombosis or infiltration by host leukocytes usually associated with focal areas of infarction (data not shown). There was low but detectable P-selectin expression on the vascular endothelium (data not shown). Hearts transplanted into CVF plus CsA-treated rats, under inhibition of HO-1 activity by SnPPIX, showed similar levels of intravascular deposition of IgM and C1q as compared with control FePPIX-treated rats and no detectable IgG, C3, or C5b-9 (data not shown). There was widespread vascular thrombosis of large coronary vessels associated with P-selectin-expressing platelet aggregates and intravascular fibrin. Thrombi were consistently observed in large coronary vessels at the base of the heart. There were no detectable P-selectin-expressing platelet aggregates in the microvasculature (data not shown). There was extensive graft infiltration by host neutrophils as well as by $CD45^{++}$ leukocytes expressing the monocyte/MΦ marker CD68/ED-1 and MHC class II Ags (data not shown). Infiltrating monocyte/MΦ were found near arterioles and scattered throughout the myocardium, associated with areas of infarction.

Hearts transplanted into SnPPIX-treated rats that were exposed to CO were essentially indistinguishable from those transplanted into rats treated with CVF plus CsA with or without FePPIX (data not shown). These hearts showed similar level of IgM and C1q vascular deposition as compared with hearts transplanted into recipients treated with SnPPIX but not exposed to CO (data not shown). Under CO exposure, there were no signs of vascular thrombosis as revealed by the lack of detectable P-selectin-expressing platelet aggregates or intravascular fibrin. P-selectin was detected on the graft vascular endothelium. There was some level of monocyte/MΦ infiltration associated with small focal areas of infarction (data not shown).

Up-regulation of HO-1 in Endothelial Cells Inhibits Platelet Aggregation

Figure 11:
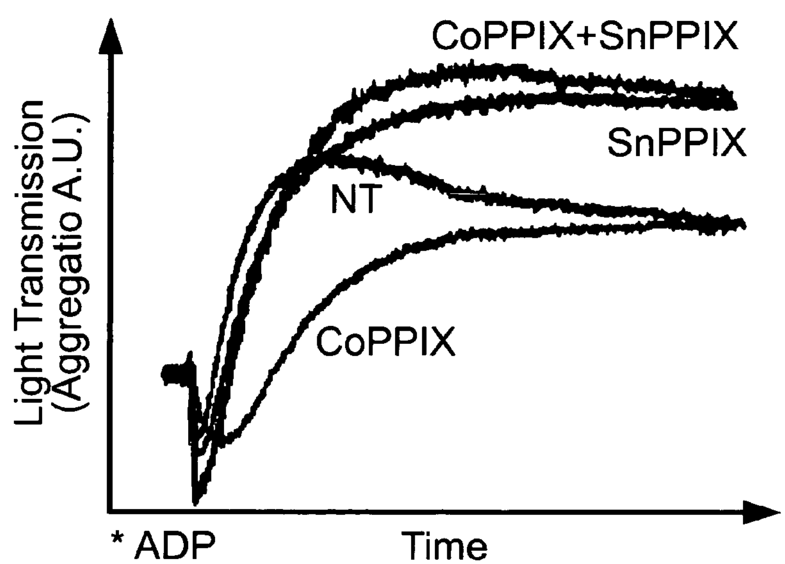
FIG. 11 is a line graph illustrating that up-regulation of HO-1 in endothelial cells inhibits platelet activation. Mouse 2F–2B endothelial cells were left untreated (NT) or were treated with CoPPIX (50 μM, 16 h) to up-regulate HO-1 activity, SnPPIX to suppress HO-1 activity (50 μM, 16 h), or CoPPIX (50 μM, 12 h) plus SnPPIX (50 μM, 4 h) to control for the specificity of CoPPIX in up-regulating HO-1 activity. Rat platelets were isolated, overlaid onto the mouse endothelial cells for 5 min, and tested for aggregation after stimulation with 2 μM of adenosine diphosphate (ADP).

Given the absence of platelet aggregation in grafts transplanted into rats exposed to CO, whether expression of HO-1 in endothelial cells would inhibit platelet aggregation in vitro was investigated. Mouse endothelial cells were exposed to CoPPIX or SnPPIX to induce or suppress HO activity in these cells, respectively. Platelets were overlaid on the endothelial cells and tested for their ability to aggregate on stimulation by ADP (2 μM). Platelets overlaid on untreated endothelial cells aggregated normally when stimulated with ADP (FIG. 11). When platelets were exposed to endothelial cells pretreated with SnPPIX, platelet aggregation was enhanced as compared with platelets exposed to untreated endothelial cells (FIG. 11). This observation indicates that untreated endothelial cells have a basal level of HO activity presumably attributable to constitutive expression of HO-2 in these cells (FIG. 11). When platelets were exposed to endothelial cells pretreated with CoPPIX, platelet aggregation was significantly inhibited as compared with platelets exposed to untreated or SnPPIX-treated endothelial cells (FIG. 11). This inhibitory effect was suppressed when platelets were exposed to endothelial cells treated with both CoPPIX and SnPPIX (FIG. 11). Both CoPPIX and SnPPIX up-regulated the expression of HO-1 in cultured endothelial cells (data not shown). The differential effects of these protoporphyrins should be attributed to the ability of SnPPIX to act as a potent inhibitor of HO-1 enzymatic activity.

HO-1 Generates CO that Suppresses Endothelial Cell Apoptosis

Figure 12:
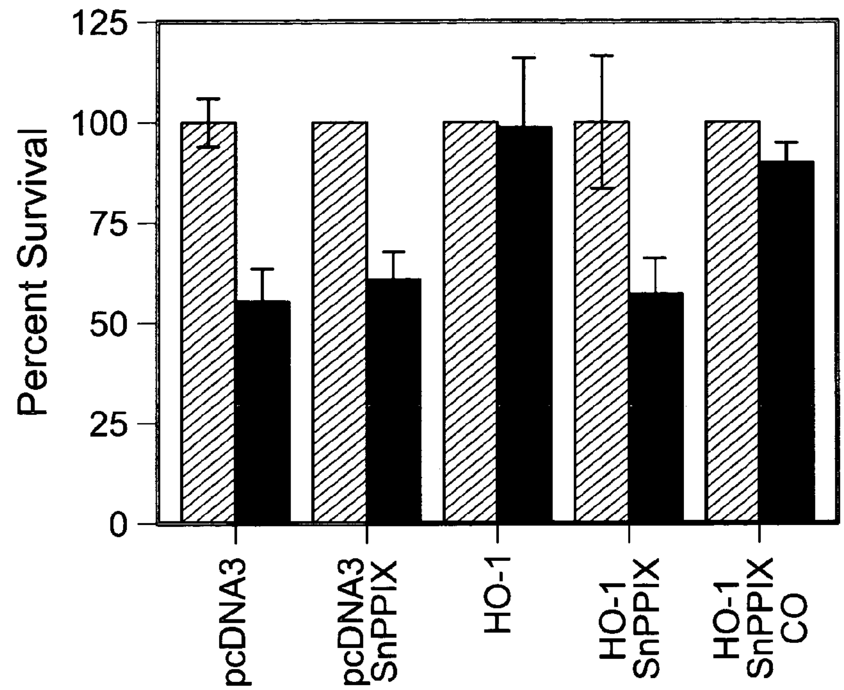
FIG. 12 is a bar graph illustrating that carbon monoxide suppresses endothelial cell apoptosis. Gray histograms represent cells treated with Act.D alone and black histograms represent cells treated with Act.D plus TNF-α. Where indicated, endothelial cells were treated with SnPPIX (50 μM) and exposed to exogenous CO (10,000 parts per million (ppm)).
Figure 13A:
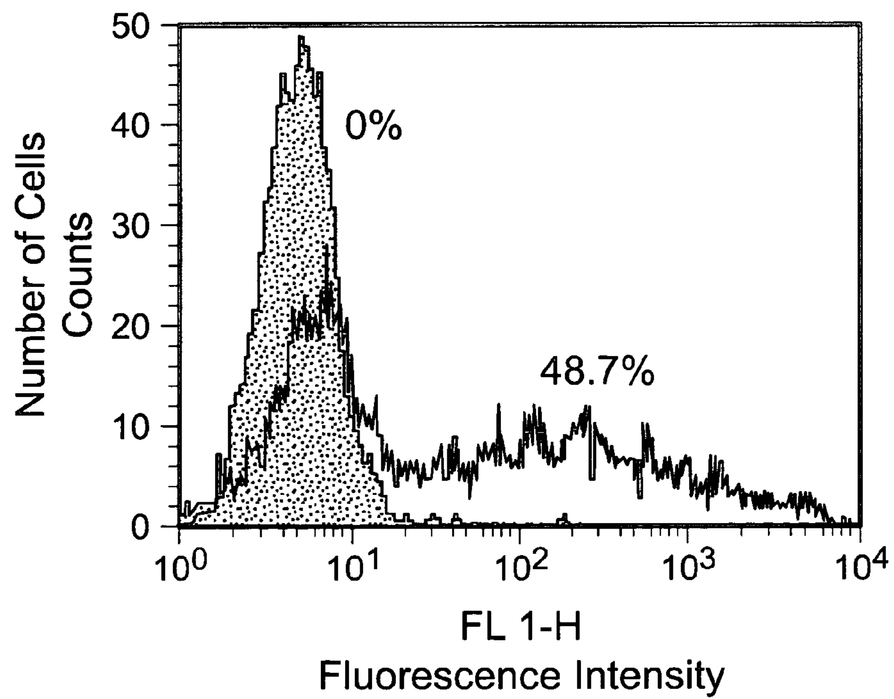
FIG. 13A is a histogram illustrating the ability of ECs to be transiently transfected. Filled histogram=cells transfected with pcDNA3 control; open histogram=cells transfected with green fluorescent protein (GFP) expression plasmids.
Figure 13B:
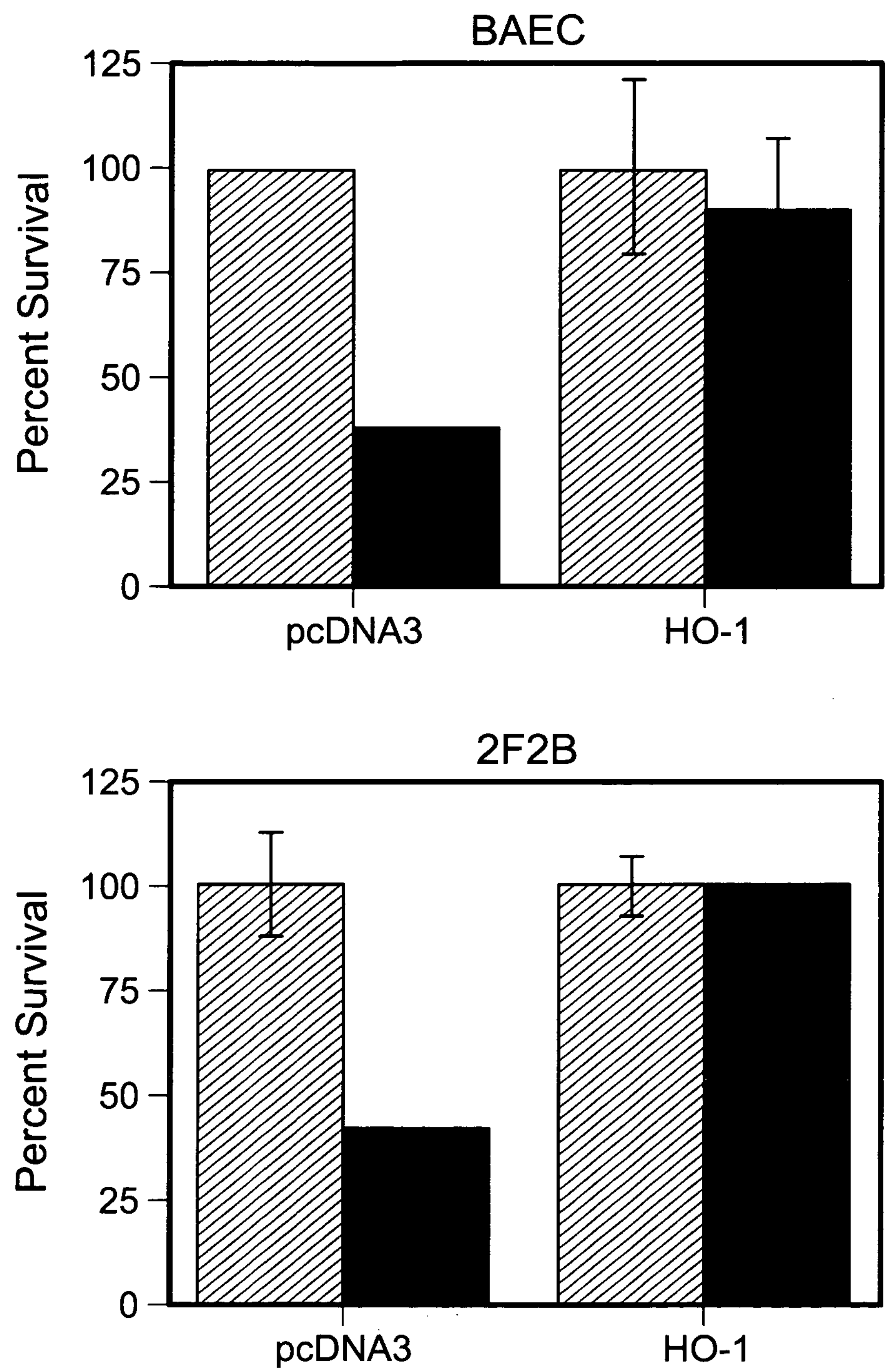
FIG. 13B is a set of bar graphs illustrating that HO-1 overexpression in ECs prevents EC apoptosis. Gray bars represent ECs treated with Act.D and black bars represent ECs treated with TNF-α plus Act.D. BAEC=bovine aortic endothelial cells.
Figure 13C:
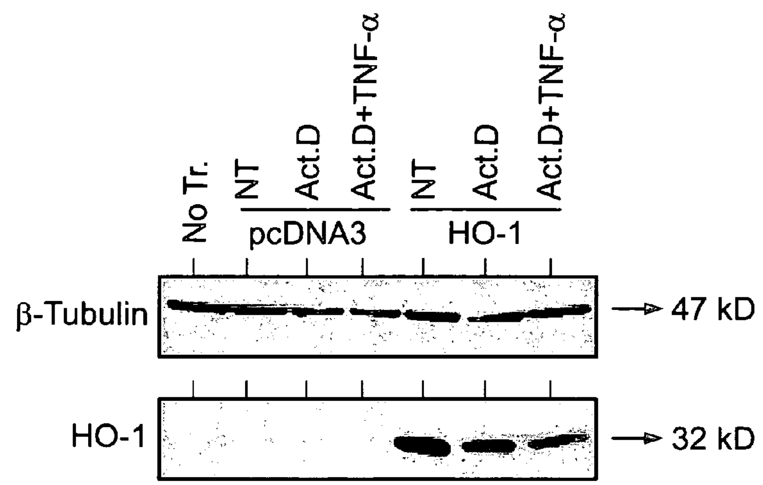
FIG. 13C is a set of Western blots illustrating that BAECs transfected with HO-1 overexpress HO-1. No Tr=nontransfected. NT=nontreated.
Figure 13D:
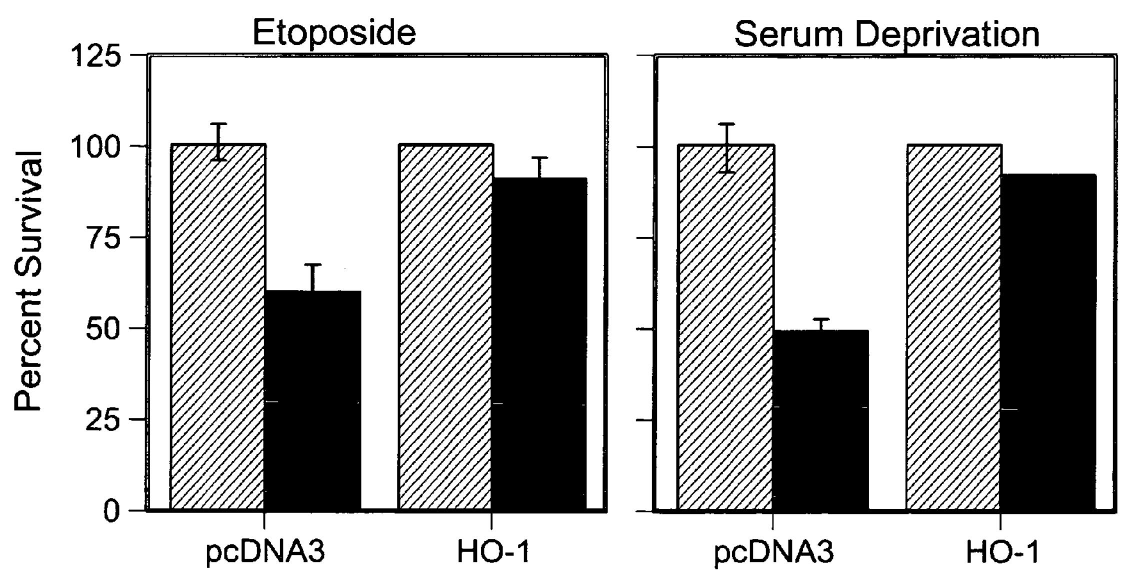
FIG. 13D is a set of bar graphs illustrating that overexpression of HO-1 prevents EC apoptosis induced by proapoptotic stimuli such as etoposide or serum deprivation. Gray bars represent untreated ECs and black bars represent ECs treated with etoposide (200 μM, 8 h) or subjected to serum deprivation (0.1% FCS for 24 h).

One of the main features that characterizes the rejection of mouse hearts transplanted into rats treated with SnPPIX is the widespread apoptosis of endothelial cells and cardiac myocytes (FIG. 12). Apoptosis did not occur in mouse hearts transplanted into rats treated with FePPIX (FIG. 12). Given the ability of HO-1 to suppress endothelial cell apoptosis in vitro (Soares et al., Nature Med. 4:1073–1077, 1998; and Brouard et al., J. Exp. Med. 192:1015, 2000), whether this cytoprotective effect was mediated via the generation of CO was investigated. Apoptosis did not occur in mouse hearts transplanted into rats treated with SnPPIX and exposed to CO, suggesting that this was the case (FIG. 12). It was investigated in vitro whether under inhibition of HO-1 activity by SnPPIX, exogenous CO would prevent endothelial cells from undergoing TNF-É-mediated apoptosis. The data illustrated in FIG. 6 suggest that this is the case. Overexpression of HO-1 suppressed TNF-α-mediated endothelial cell apoptosis, such as it occurs in the presence of actinomycin D (FIG. 12). The antiapoptotic effect of HO-1 is mediated through its enzymatic activity because exposure of endothelial cells to SnPPIX blocked the anti-apoptotic effect of HO-1 (FIG. 12). Under inhibition of HO-1 activity by SnPPIX, exogenous CO (10,000 ppm) suppressed TNF-É-mediated apoptosis, suggesting that HO-1 suppresses endothelial cell apoptosis via the generation of CO (FIG. 12).

Carbon Monoxide Suppresses the Development of Transplant-associated Arteriosclerosis Brown Norway aortas were transplanted into Brown Norway rats (syngeneic), untreated Lewis rats (allogeneic), or Lewis rats exposed to carbon monoxide (250 ppm; allogeneic with carbon monoxide). Samples were harvested 56 days after transplantation and stained by a modified elastic tissue-masson trichrome, or by eosin hematoxylin. Brown Norway aortic segments transplanted into Lewis rats developed arteriosclerotic lesions that are consistent with those associated with chronic graft rejection (data not shown). These lesions became apparent 20–30 days after transplantation and were significantly more pronounced by 50–60 days (data not shown). For this reason, all analyses were carried out 56 days following transplantation. These lesions were characterized by intimal hyperplasia, loss of medial smooth muscle cells (SMC) and accumulation of leukocytes in the adventitia, and were not observed in aortas of the transplant recipient (data not shown). No signs of these lesions were observed when rat aortic segments were transplanted into syngeneic recipients. To test whether CO would suppress the development of these lesions, aortic grafts were transplanted into allogeneic recipients that were then exposed to CO (250 ppm) immediately following transplantation and for the subsequent 56 days. Intimal hyperplasia was inhibited in aortic grafts transplanted into recipients exposed to CO, as compared to those transplanted into recipients exposed to air, as was the accumulation of leukocytes into the adventitia (data not shown). CO had no significant effect on loss of medial SMC as compared to grafts transplanted into untreated recipients (data not shown).

EXAMPLE III

Carbon Monoxide Suppresses Endothelial Cell Apoptosis

Cell Culture

The murine 2F–2B EC line and primary bovine aortic ECs (BAECs) were cultured as described previously.

Expression Plasmids

β-galactosidase cDNA was cloned into the pcDNA3 vector (Invitrogen). Two vectors encoding rat HO-1 cDNA were used. The original vector encoding the full-length rat HO-1 cDNA under the control of a the β-actin enhancer/promoter (β-actin/HO-1) has been described elsewhere. A 1.0-kbp XhoI-HindIII fragment encoding the full-length rat HO-1 cDNA was cut from the prHO-1 vector and subclones into the pcDNA3 vector to achieve expression of the HO-1 cDNA under the control of the CMV enhancer/promoter (pcDNA3/HO-1). The mouse Bcl-2 cDNA was cloned in the pac vector. p38/CSBP1 MAPK was amplified from HeLa cell cDNA by PCR and cloned into the pcDNA3/HA vector derived from pcDNA3 by inserting a DNA fragment coding for an epitope derived from the hemagglutinin protein of the human influenza virus hemagglutinin (HA; MYPYDVPDYASL). A dominant negative mutant of p38/CSBP1, harboring a T180A and a Y182F substitution, was generated by overlap extension mutagenesis. Green fluorescent protein (GFP) cDNA (CLONTECH Laboratories, Inc.) was cloned into the pcDNA3-expressing vector.

Transient Transfections

BAECs and 2F–2B ECs were transiently transfected. All experiments were carried out 24–48 h after transfection. The percentage of viable cells was assessed by evaluating the number of β-galactosidase-expressing cells that retained normal morphology. The number of random fields counted was determined to have a minimum of 200 viable transfected cells per control well. The percentage of viable cells was normalized for each DNA preparation to the number of transfected cells counted in the absence of the apoptosis-inducing agent (100% viability). All experiments were performed at least three times in duplicate.

Adenovirus

The recombinant HO-1 adenovirus has been described previously. The recombinant β-galactosidase adenovirus was a gift of Dr. Robert Gerard (University of Texas Southwestern Medical Center, Dallas, Tex.). Adenoviruses were produced, extracted, purified, and titrated. Confluent BAECs were infected with a multiplicity of infection of 200 PFU/cell.

Cell Extracts and Western Blot Analysis

Cell extracts were prepared, electrophoresed under denaturing conditions (10–12.5% polyacrylamide gels), and transferred into polyvinyldifluoridine membranes (Immobilon P™; Millipore). HO-1 was detected using a rabbit anti-human HO-1 polyclonal antibody (StressGen Biotechnologies). Vasodilatator-stimulated phosphoprotein (VASP) was detected using a rabbit anti-human VASP polyclonal antibody (Calbiochem-Novabiochem). Total and activated/phosphorylated forms of extracellular signal-regulated kinases (ERK-1 and -2), c-Jun $NH_2$-terminal kinases (JNK-1, -2, and -3), and p38 MAPK were detected using rabbit polyclonal antibodies directed against the total or phosphorylated forms of these MAPKs, according to the manufacturer's suggestions (New England Biolabs, Inc.). β-Tubulin was detected using anti-human β-tubulin monoclonal antibody (Boehringer). Primary antibodies were detected using horseradish peroxidase-conjugated donkey anti-rabbit or goat anti-mouse IgG secondary antibodies (Pierce Chemical Co.). Peroxidase was visualized using the enhanced chemiluminescence assay (Amersham Pharmacia Biotech) according to the manufacturer's instructions, and stored in the form of photoradiographs (Biomax™ MS; Eastman Kodak Co.). Digital images were obtained using an image scanner (Arcus II; Agfa) equipped with FotoLook™ and Photoshop® software. The amount of phosphorylated ERK, JNK, and p38 MAPK was quantified using ImageQuant® software (Molecular Dynamics). When indicated, membranes were stripped (62.5 mM Tris-HCl, pH 6.8, 2% SDS, and 100 mM β-mercaptoethanol, 30 min, 50° C.). Phosphorylated ERK, JNK, and p38 MAPK were normalized to the total amount of total ERK, JNK, and p38 MAPK detected in the same membrane.

Flow Cytometry

2F–2B ECs were transfected with the GFP expression plasmid and harvested 24 h after transfection by trypsin digestion (0.05% in PBS). ECs were washed in PBS, pH 7.2, 5% FCS, and fluorescent labeling was evaluated using a FACSort™ equipped with CELLQuest™ software (Becton Dickinson).

Cell Treatment and Reagents

Actinomycin D (Act.D; Sigma-Aldrich) was dissolved in PBS and added to the culture medium 24 h after transfection. The Act.D concentration used corresponded to the optimal concentration necessary to sensitize ECs to TNF-α mediated apoptosis, e.g., 10 μg/ml for 2F–2B ECs and 0.1 μg/ml for BAECs. When indicated, EC apoptosis was induced by etoposide (200 μM, 8 h; Calbiochem-Novabiochem) or by serum deprivation (0.1% FCS for 24 h). The iron chelator deferoxamine mesylate (DFO; Sigma-Aldrich) was dissolved in water and added to culture medium (1–100 μM) 1 h before the induction of apoptosis. Hemoglobin (Hb; Sigma-Aldrich) was dissolved (1 mM) in PBS, 10 mM $Na_2S_2O_4$, dialyzed against PBS (2 h, 4° C., 1:800 dilution), and added to the culture medium (1–100 μM) 6 h after transfection. The guanylcyclase inhibitor 1H(1,2,4)oxadiazolo(4,3)quinoxalin-1 (ODQ; Calbiochem-Novabiochem) was dissolved in DMSO (Sigma-Aldrich) and added to the culture medium (10–100 μM) 6 h after transfection. Iron protoporphyrin ([FePP]/heme), cobalt protoporphyrin (CoPPIX), and tin protoporphyrin (SnPPIX; all from Porphyrin Products, Inc.) were dissolved (10 mM) in 100 mM NaOH and held at −20° C. until use. Metalloporphyrins were added to the culture medium (50 μM) 6 h after transfection. The cGMP analogue 8-bromo-cGMP sodium salt (8-Br-cGMP; Sigma-Aldrich) was dissolved in water and added to the culture medium (10–100 gM) 30 min before the induction of apoptosis. Human recombinant TNF- (R&D Systems) was dissolved in PBS and 1% BSA, and added to the culture medium (10–100 ng/ml) 24 h after transfection. The p38 MAPK inhibitor pyridinyl imidazol SB203580 was dissolved in DMSO and added to the culture medium (5–20 μM) 6 h after transfecion.

CO Exposure

Cells were exposed to compressed air from a compressed air tank or varying concentrations of CO (250 and 10,000 ppm).

HO-1 Protects ECs from Apoptosis

TNF-α induces apoptosis of cultured ECs when transcriptional activity is inhibited by Act.D. We have used this experimental system to ask whether transient overexpression of HO-1 could prevent ECs from undergoing apoptosis. The data in FIGS. 13A–D were generated as follows: (A) 2F–2B ECs were transfected with a GFP-expressing plasmid and monitored for GFP expression by flow cytometry. The percentage of transfected ECs was assessed by measuring fluorescence intensity in ECs transfected with control (pcDNA3; filled histogram) versus GFP (open histogram) expression plasmids; (B) ECs were cotransfected with β-galactosidase plus control (pcDNA3) or HO-1 (β-actin/HO-1) expression vectors. EC apoptosis was induced by TNF-α plus Act.D and apoptosis of β-galactosidase-transfected ECs was quantified. Gray bars represent ECs treated with Act.D and black bars represent ECs treated with TNF-α plus Act.D. Results shown are the mean±SD from duplicate wells taken from 1 representative experiment out of 10; (C) HO-1 expression was detected in BAECs by Western blot. No Tr, nontransfected. NT, nontreated; (D) 2F–2B ECs were cotransfected with β-galactosidase plus control (pcDNA3) or HO-1 (β-actin/HO-1) expression vectors. Gray bars represent untreated ECs and black bars represent ECs treated with etoposide (200 μM, 8 h) or subjected to serum deprivation (0.1% FCS for 24 h). Results shown are the mean±SD from duplicate wells taken from one representative experiment out of three independent experiments. Similar results were obtained using BAECs. We first evaluated the ability of ECs to be transiently transfected. To do so, ECs were transfected with a GFP-expressing plasmid and the percentage of GFP-expressing ECs was evaluated by flow cytometry. As illustrated in FIG. 13, 45% of ECs expressed the GFP protein 24 h after transfection. We then tested whether transfection of HO-1 would prevent ECs from undergoing TNF-α mediated apoptosis. To do so, ECs were cotransfected with HO-1 and β-galactosidase and apoptosis was evaluated by counting the number of viable β-galactosidase-expressing ECs. TNF-α plus Act.D induced apoptosis of control ECs transfected with the pcDNA3 (60–70% apoptotic ECs). Overexpression of HO-1 prevented EC apoptosis (5–10% apoptotic ECs; FIG. 13). The expression of HO-1 was confirmed by Western blot (FIG. 13). Overexpression of HO-1 also prevented EC apoptosis induced by other proapoptotic stimuli such as etoposide or serum deprivation, which is in keeping with similar observations in 293 cells.

Figure 14A:
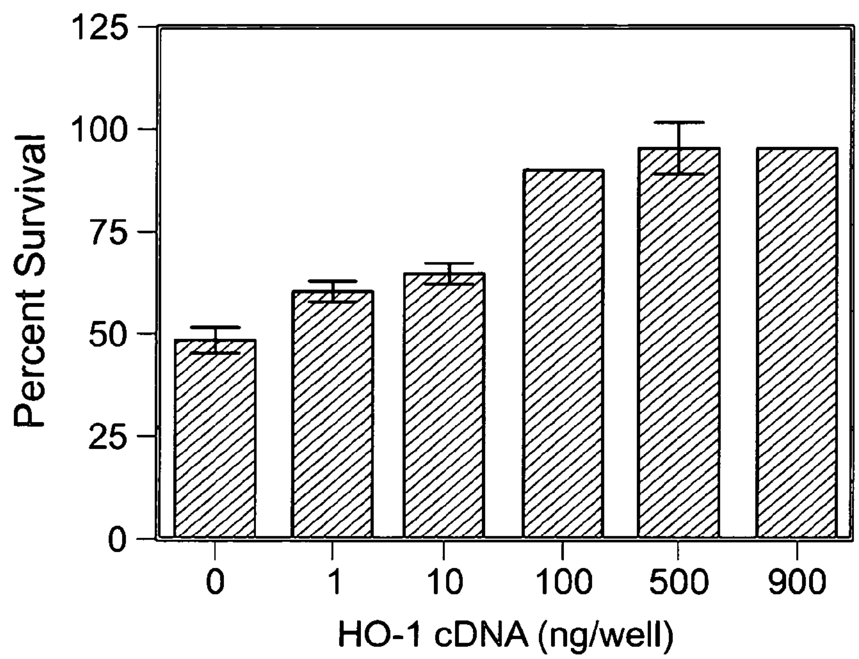
FIG. 14A is a bar graph illustrating that the antiapoptotic effect of HO-1 is dose dependent. Results shown are the mean±SD from duplicate wells taken from one representative experiment out of three.
Figure 14B:
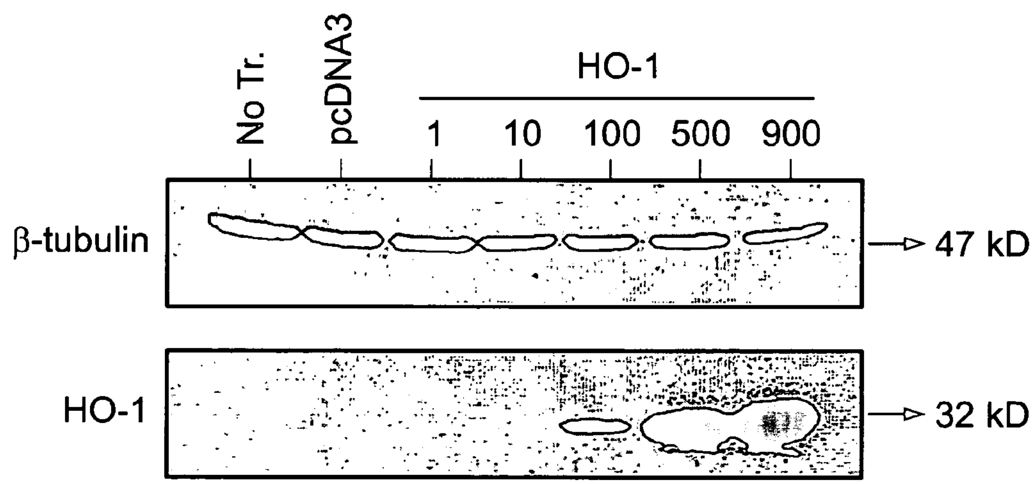
FIG. 14B is a set of Western blots illustrating the expression of HO-1 in BAECs transfected with increasing amounts of HO-1 expression vector. Values indicate the amount of HO-1 vector (pcDNA3/HO-1) used in each transfection (ng of DNA per $3\times10^5$ cells). No Tr.=nontransfected.

The antiapoptotic effect of HO-1 was dose dependent in that increasing levels of HO-1 expression resulted in increased protection from TNF-α plus Act.D-mediated apoptosis (FIG. 14). The data in FIGS. 14A–B were generated as follows: (A) 2F–2B ECs were cotransfected with increasing doses of HO-1 expression vector (β-actin/HO-1). EC apoptosis was induced by TNF-α plus Act.D. Results shown are the mean±SD from duplicate wells taken from one representative experiment out of three. Similar results were obtained using BAECs; (B) The expression of HO-1 was detected in BAECs by Western blot. Values indicate the amount of HO-1 vector (pcDNA3/HO-1) used in each transfection (ng of DNA per $3\times10^5$ cells). No Tr., nontransfected. The maximal antiapoptotic effect of HO-1 (90–100% protection) was reached using 500–1,000 ng of the β-actin/HO-1 expression vector per $3\times10^5$ cells (FIG. 14). All subsequent experiments were carried out using these experimental conditions.

The Antiapoptotic Function of HO-1 Requires its Enzymatic Activity

Figure 15A:
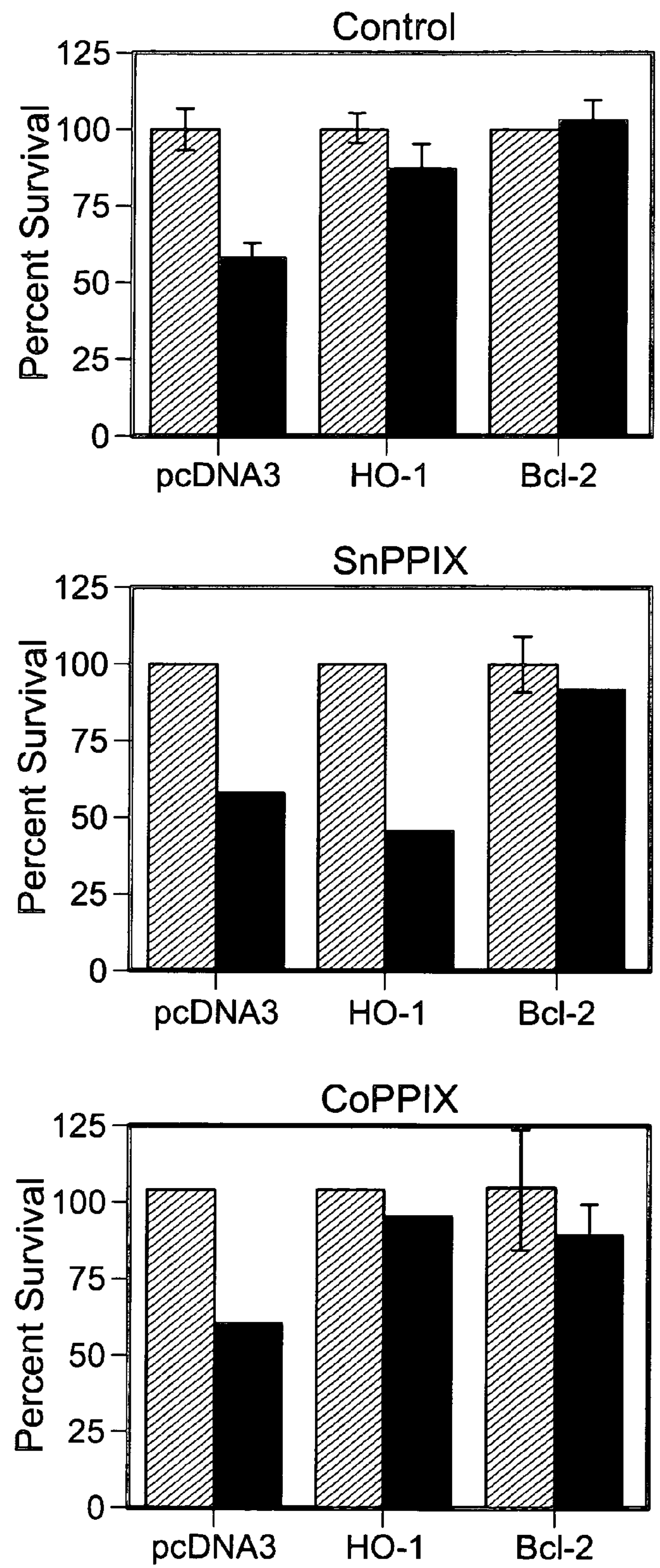
FIG. 15A is a set of bar graphs illustrating that the antiapoptotic effect of HO-1 is dependent on HO enzymatic activity. Control=untreated cells; SnPPIX=cells treated with tin protoporphyrin; CoPPIX=cells treated with cobalt protoporphyrin. Gray bars represent ECs treated with Act.D. Black bars represent ECs treated with TNF-α plus Act.D.
Figure 15B:
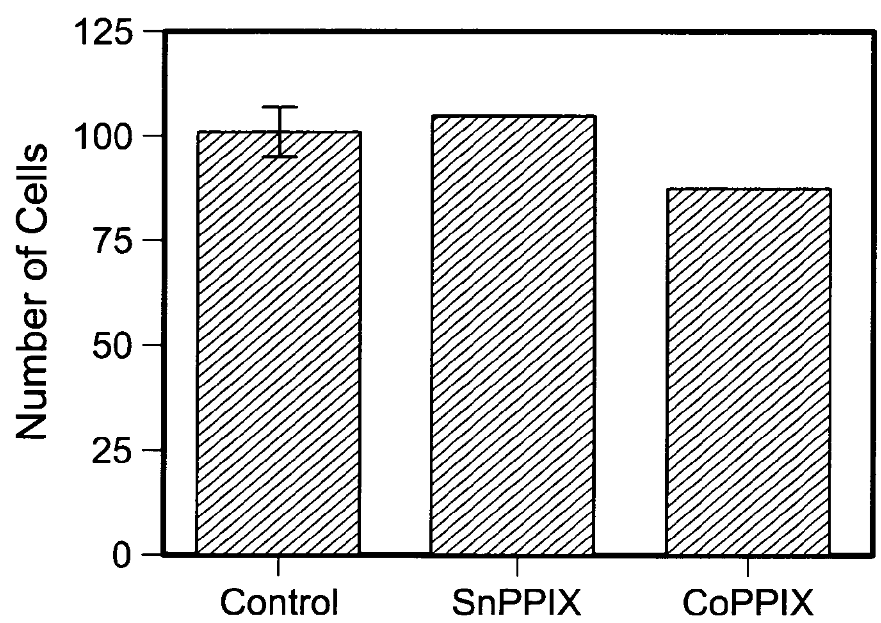
FIG. 15B is a bar graph illustrating that protoporphyrins alone have no detectable effect on EC viability. Control=untreated cells; SnPPIX=cells treated with tin protoporphyrin; CoPPIX=cells treated with cobalt protoporphyrin.

To test whether the antiapoptotic action of HO-1 was dependent on its enzymatic action, HO-1 activity was blocked using SnPPIX (FIGS. 15A–B). The data in FIGS. 15A–B were generated as follows: (A) 2F–2B ECs were cotransfected with β-galactosidase plus pcDNA3, HO-1 (β-actin/HO-1), or bcl-2 expression vectors. Cells were either left untreated (Control) or treated with the inhibitor of HO enzymatic activity SnPPIX. CoPPIX, a protoporphyrin that does not inhibit HO enzymatic activity, was used as a control treatment. Gray bars represent ECs treated with Act.D and black bars represent ECs treated with TNF-α plus Act.D. Results shown are the mean±SD from duplicate wells taken from one representative experiment out of three. (B) 2F–2B ECs were transfected with β-galactosidase plus pcDNA3 expression vectors. ECs were either left untreated (Control) or were treated with SnPPIX and CoPPIX as in A. The results shown are the mean±SD from duplicate wells taken from one representative experiment out of three. When HO-1 activity was blocked by SnPPIX, HO-1 was no longer able to prevent EC apoptosis (FIG. 15), and the antiapoptotic effect of bcl-2 was not impaired by SNPPIX (FIG. 15). CoPPIX, which has a similar structure to SnPPIX but does not inhibit HO activity, did not suppress the antiapoptotic effect of HO-1 or that of bcl-2 (FIG. 15). These protoporphyrins had no detectable effect per se on EC viability (FIG. 15).

Endogenous CO Mediates the Antiapoptotic Effect of HO-1

Figure 16:
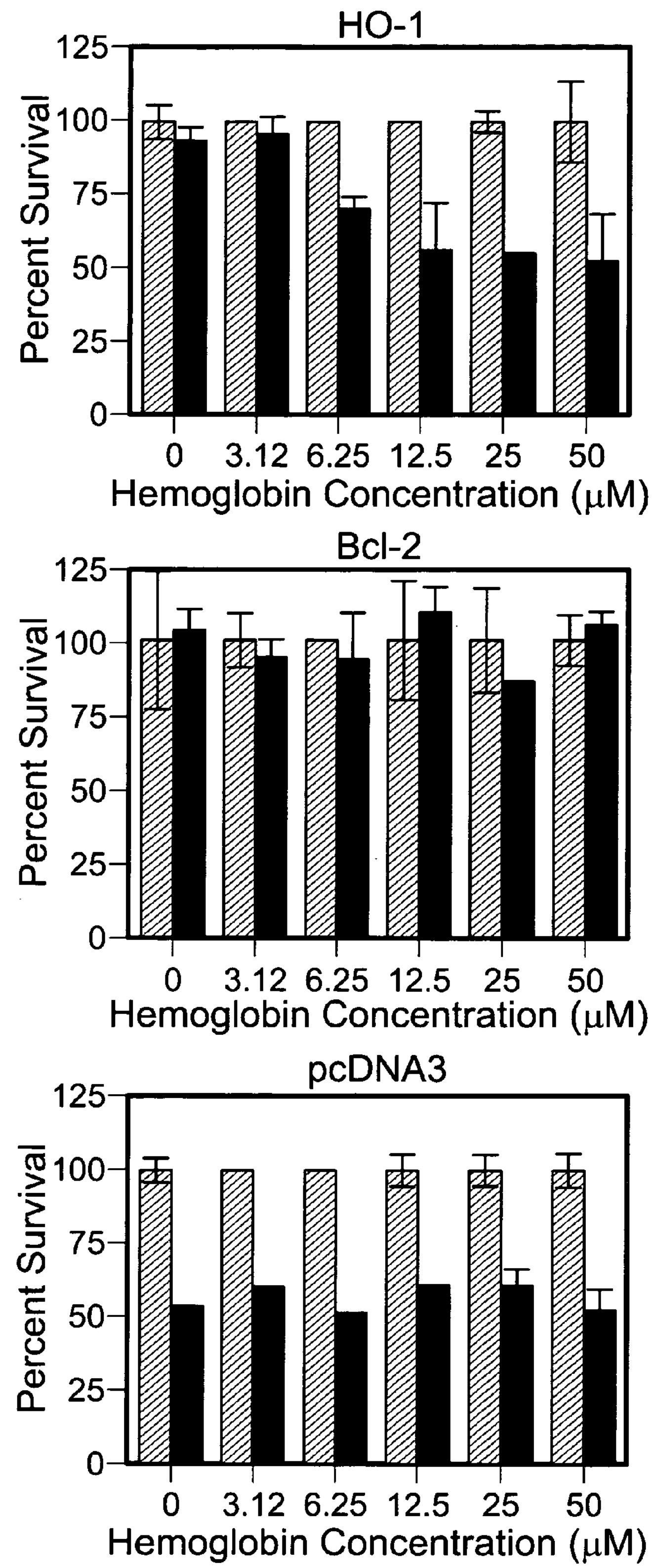
FIG. 16 is a set of bar graphs illustrating that scavenging of CO by hemoglobin (Hb) suppresses the antiapoptotic effect of HO-1. pcDNA3=β-galactosidase plus control expression vector, HO-1=β-galactosidase plus β-actin/HO-1 expression vector, Bcl-2=β-galactosidase plus bcl-2 expression vector. ECs were either left untreated (0) or were treated with increasing concentrations of Hb. Gray bars represent ECs treated with Act.D. Black bars represent ECs treated with TNF-α plus Act.D.

Since HO-1 enzymatic activity is needed for its antiapoptotic effect, this suggests that this antiapoptotic effect is mediated through one or more end products of heme catabolism by HO-1, i.e., bilirubin, iron, and/or CO. We tested whether CO would account for the antiapoptotic effect of HO-1. ECs were transiently transfected with HO-1 and treated with Hb to scavenge CO (FIG. 16). The data in FIG. 16 were generated as follows: 2F–2B ECs were cotransfected with β-galactosidase plus control (pcDNA3), HO-1 (β-actin/HO-1), or bcl-2 expression vectors. ECs were either left untreated (0) or were treated with increasing concentrations of Hb. Gray bars represent ECs treated with Act.D and black bars represent ECs treated with TNF-α plus Act.D. The results shown are the mean±SD from duplicate wells taken from one representative experiment out of four. Under these conditions, the antiapoptotic effect of HO-1 was suppressed (FIG. 16). The ability of Hb to block the antiapoptotic effect of HO-1 was dose dependent, in that increasing concentrations of Hb (3–50 μM) decreased the ability of HO-1 to prevent EC apoptosis (FIG. 16). Hb did not impair the antiapoptotic effect of bcl-2 (FIG. 16), nor did it sensitize control ECs (pcDNA3) to apoptosis (FIG. 16).

Exogenous CO can Substitute for HO-1 in Preventing EC Apoptosis

Figure 17A:
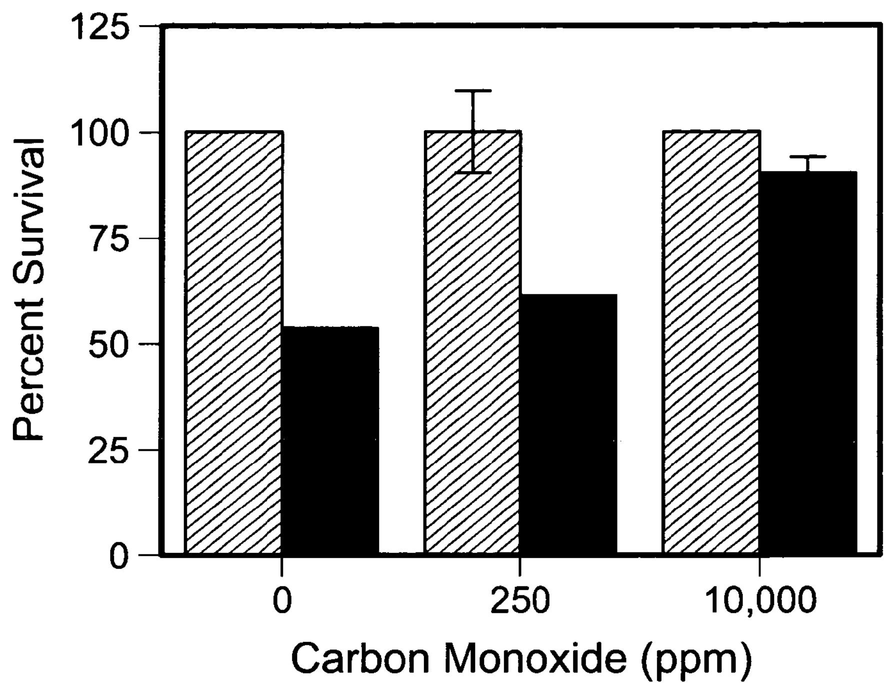
FIG. 17A is a bar graph illustrating that exogenously administered CO suppresses TNF-α-mediated apoptosis in ECs. Gray bars represent ECs treated with Act.D. Black bars represent ECs treated with TNF-α plus Act.D.
Figure 17B:
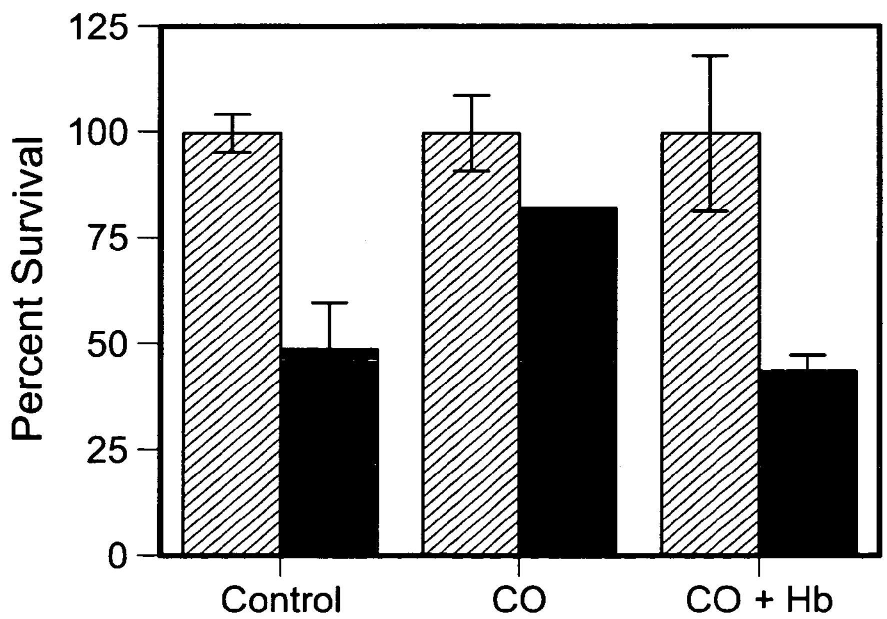
FIG. 17B is a bar graph illustrating that exogenously administered CO (10,000 ppm) suppresses TNF-α-mediated apoptosis in ECs in the presence of tin protoporphyrin, but not in the presence of Hb. Control=untreated cells; CO=cells treated with CO; CO+Hb=cells treated with both CO and Hb. Gray bars represent ECs treated with Act.D. Black bars represent ECs treated with TNF-α plus Act.D.
Figure 17C:
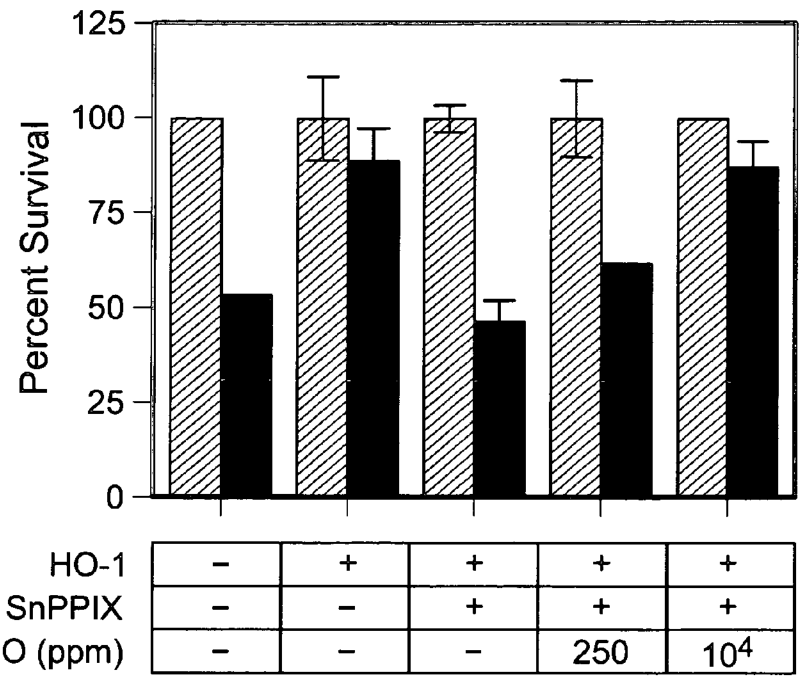
FIG. 17C is a bar graph and grid illustrating that exogenously administered CO (10,000 ppm) suppressed TNF-α-mediated apoptosis in ECs in the presence of tin protoporphyrin. (+)=HO-1 transfected cells treated with tin protoporphyrin and/or exogenous CO. Gray bars represent ECs treated with Act.D. Black bars represent ECs treated with TNF-α plus Act.D.

If CO mediates the antiapoptotic action of HO-1, then exogenous CO should prevent EC apoptosis. The data illustrated in FIGS. 17A–C show that this is the case. The data in FIGS. 17A–C were generated as follows: (A) 2F–2B ECs were transfected with a β-galactosidase expression vector and exposed to exogenous CO. Gray bars represent ECs treated with Act.D alone and black bars represent ECs treated with TNF-α plus Act.D. (B) 2F–2B ECs were transfected with a β-galactosidase expression vector and exposed to exogenous CO (10,000 ppm) with or without Hb. Gray bars represent ECs treated with Act.D and black bars represent ECs treated with TNF-α plus Act.D. (C) 2F–2B ECs were cotransfected with β-galactosidase and HO-1 (β-actin/HO-1) expression vectors. Where indicated (+), HO-1 enzymatic activity was inhibited by SnPPIX and/or exposed to exogenous CO. Gray bars represent ECs treated with Act.D and black bars represent ECs treated with TNF-α plus Act.D. Results shown (A, B, and C) are the mean±SD from duplicate wells taken from one representative experiment out of three. When control ECs (transfected with pcDNA3) were exposed to exogenous CO (10,000 ppm), TNF-α mediated apoptosis was suppressed (FIG. 17). Exogenous CO also suppressed EC apoptosis when HO-1 activity was inhibited by SnPPIX, suggesting that CO can prevent EC apoptosis in the absence of other biological functions of HO-1 (FIG. 17). We then tested whether the level of exogenous CO used (10,000 ppm) was comparable to that produced when HO-1 is expressed in ECs. Given that Hb (50 μM) blocks the protective effect of endogenously produced CO (FIG. 16), we reasoned that if were the case for exogenous CO, then the effects of exogenous CO may mimic those of endogenous CO. The antiapoptotic effect of exogenous CO was suppressed by Hb (50 μM), suggesting that the concentration of exogenous CO (10,000 ppm) used in these experiments is not supraphysiologic (FIG. 17).

ECs that Express HO-1 can Suppress Apoptosis of ECs that do not Express HO-1

Figure 18:
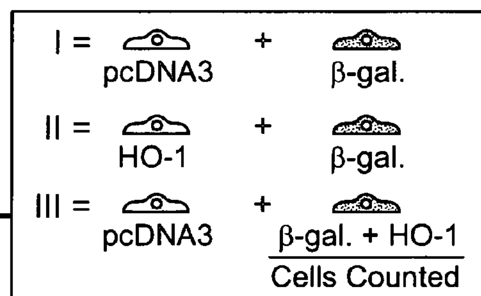
FIG. 18 is a bar graph and diagram illustrating that ECs that express HO-1 suppress apoptosis of ECs that do not express HO-1. ECs were transfected with control (pcDNA3; I and II) or HO-1 (III) expression vectors. ECs were then transfected with β-galactosidase (I and II) or with β-galactosidase plus HO-1 (III). Gray bars represent ECs treated with Act.D. Black bars represent ECs treated with TNF-α plus Act.D.
Figure 18:
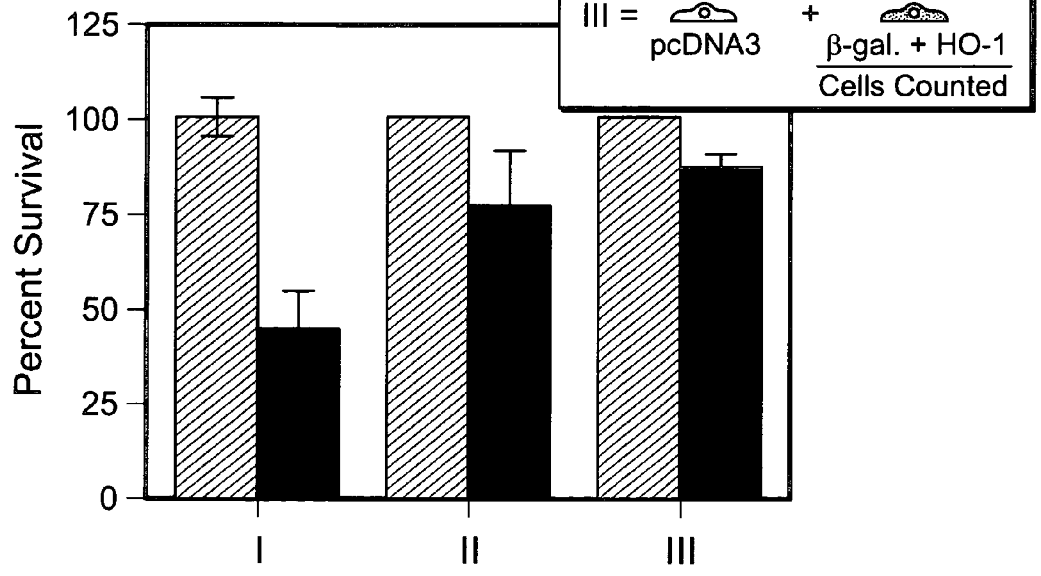

Given that CO can act as an intercellular signaling molecule, we hypothesized that ECs that express HO-1 may generate sufficient levels of CO to protect neighboring ECs that do not express HO-1 from undergoing apoptosis. To test this hypothesis, ECs were transfected with control (pcDNA3) or HO-1 expression vectors and cocultured with β-galactosidase-transfected ECs (FIG. 18). The data in FIG. 18 were generated as follows: 2F–2B ECs were transfected with control (pcDNA3; I and II) or HO-1 (III) expression vectors. 16 h after transfection, ECs were harvested, washed, and cocultured at a ratio of 1:1 with ECs transfected with β-galactosidase (I and II) or with β-galactosidase plus HO-1 (III). Cocultures were maintained for an additional 24 h before induction of apoptosis by TNF-α plus Act.D. The percentage of survival was evaluated by counting the number of β-galactosidase-positive cells that retained normal morphology. Gray bars represent ECs treated with Act.D and black bars represent ECs treated with TNF-α plus Act.D. Results shown are the mean±SD from duplicates taken from one representative experiment out of three. When cocultured with control ECs (pcDNA3), TNF-α plus Act.D induced apoptosis of β-galactosidase-transfected ECs (that do not express HO-1). However, when cocultured with ECs expressing HO-1, β-galactosidase-transfected ECs were protected from TNF-α plus Act.D-mediated apoptosis (FIG. 18).

Expression of Endogenous HO-1 Inhibits EC Apoptosis Via CO

Figure 19A:
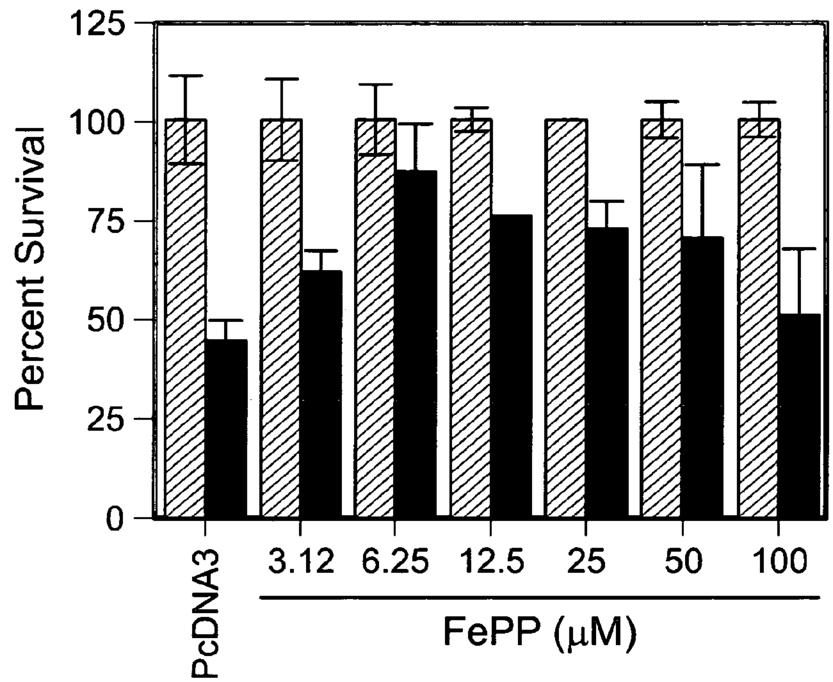
FIG. 19A is a bar graph illustrating that upregulation of endogenous HO-1 expression by heme inhibits EC apoptosis via CO. pcDNA=control; FePP=iron protoporphyrin (heme). Gray bars represent ECs treated with Act.D. Black bars represent ECs treated with TNF-α plus Act.D.
Figure 19B:
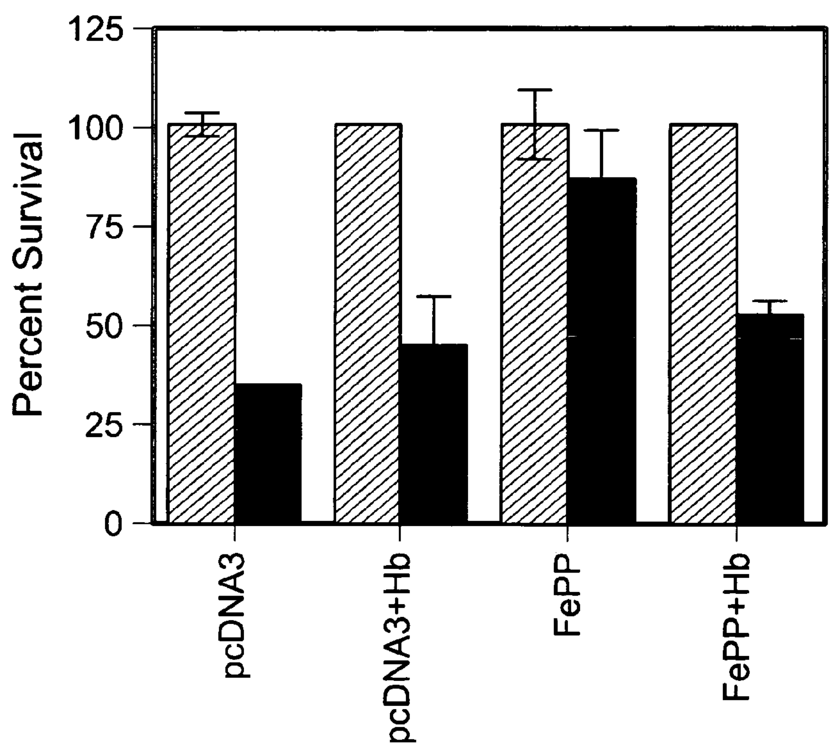
FIG. 19B is a bar graph illustrating that heme is unable to suppress EC apoptosis when CO is scavenged by Hb. pcDNA=control; pcDNA+Hb=control cells treated with Hb (50 μM); FePP=cells treated with iron protoporphyrin; FePP+Hb=cells treated with iron protoporphyrin and Hb (50 μM). Gray bars represent ECs treated with Act.D. Black bars represent ECs treated with TNF-α plus Act.D.

We questioned whether upregulation of endogenous HO-1 by heme would suppress EC apoptosis. The data illustrated in FIGS. 19A–B suggest that this is the case. The data in FIGS. 19A–B were generated as follows: (A) 2F–2B ECs were cotransfected with a β-galactosidase expression vector and exposed to FePP. Apoptosis was induced by TNF-α and Act.D. Gray bars represent ECs treated with Act.D and black bars represent ECs treated with TNF-α plus Act.D. The results shown are the mean±SD from duplicate wells taken from one representative experiment out of three. (B) 2F–2B ECs were cotransfected with a β-galactosidase expression vector and exposed to FePP (6.25 μM). Where indicated, ECs were treated with Hb (50 μM). The results shown are the mean±SD from duplicate wells taken from one representative experiment out of three. Exposure to heme protected ECs from TNF-α plus Act.D-mediated apoptosis (FIG. 19). This protective effect was observed only at heme concentrations ranging from 5 to 7 μM and was lost at higher concentrations, suggesting that heme becomes cytotoxic at concentrations higher than 10 μM (FIG. 19). The antiapoptotic effect of heme was dependent on the generation of CO, since heme was no longer able to suppress EC apoptosis when CO was scavenged by Hb (FIG. 19).

Iron Chelation Protects ECs from Apoptosis

Figure 20A:
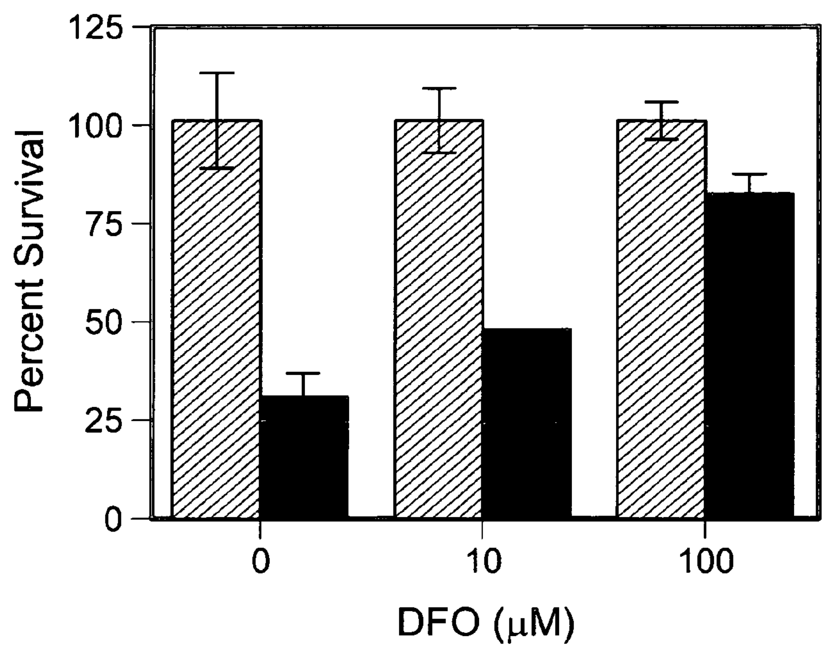
FIG. 20A is a bar graph illustrating that iron chelation by deferoxamine mesylate (DFO) suppresses EC apoptosis. Gray bars represent ECs treated with Act.D. Black bars represent ECs treated with TNF-α plus Act.D.
Figure 20B:
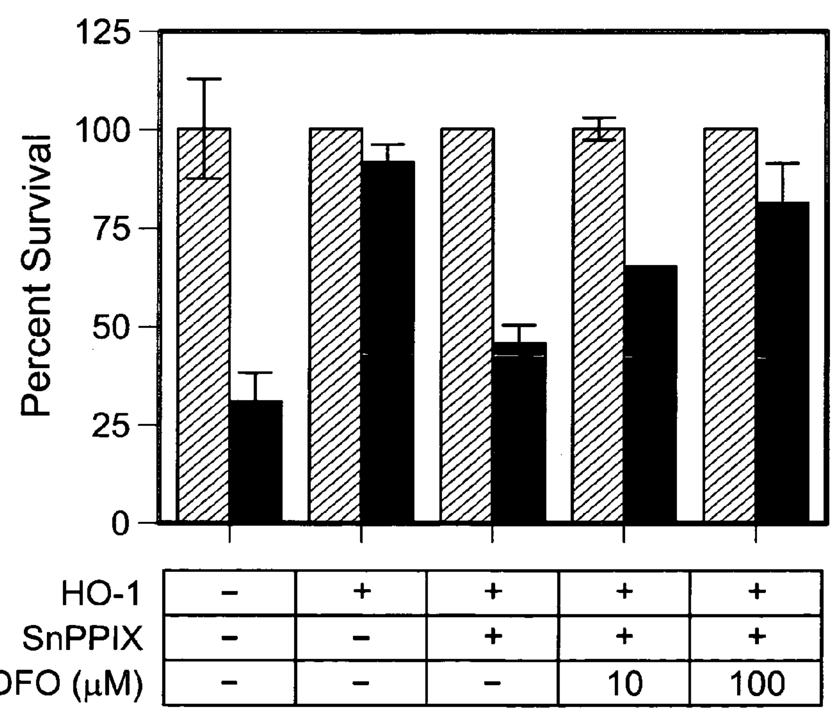
FIG. 20B is a bar graph and grid illustrating that DFO suppresses EC apoptosis in the presence of tin protoporphyrin. (+)=HO-1 transfected cells treated with tin protoporphyrin and/or exogenous DFO. Gray bars represent ECs treated with Act.D. Black bars represent ECs treated with TNF-α plus Act.D.
Figure 20C:
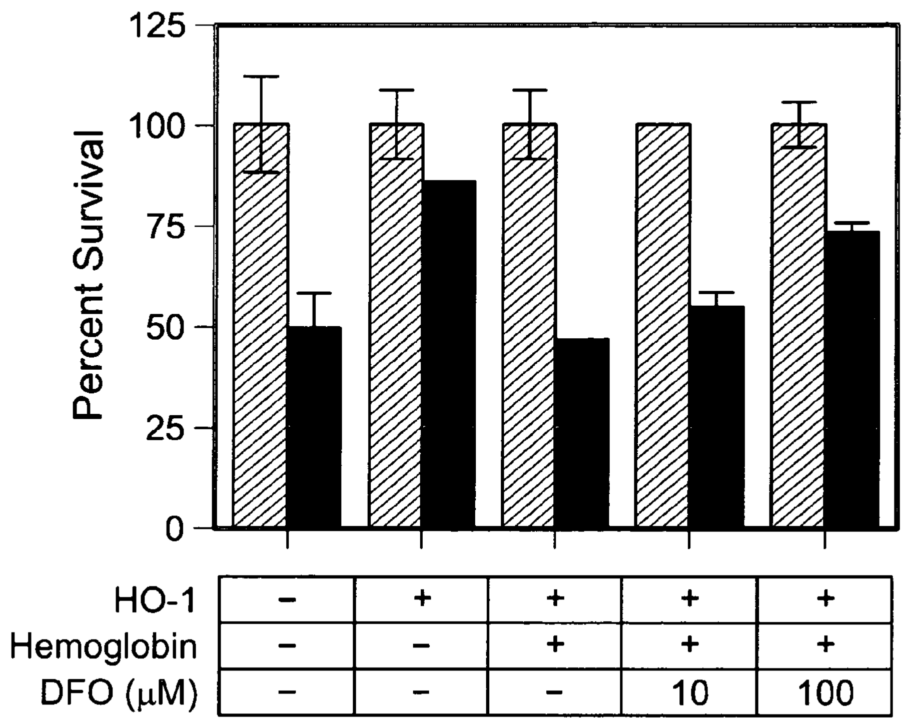
FIG. 20C is a bar graph and grid illustrating that DFO suppresses EC apoptosis in the presence of heme. (+)=HO-1 transfected cells treated with tin protoporphyrin and/or exogenous DFO. Gray bars represent ECs treated with Act.D. Black bars represent ECs treated with TNF-α plus Act.D.

The observation that CO can prevent EC apoptosis (FIGS. 16 and 17) contrasts with the notion that the antiapoptotic effect of HO-1 derives exclusively on its ability to prevent intracellular iron accumulation. Given that overexpression of HO-1 in ECs resulted in significant upregulation of ferritin expression (data not shown), we questioned whether elimination of reactive intracellular iron such as it occurs when ferritin is expressed would contribute to prevent TNF-α-mediated apoptosis of ECs. To mimic the iron chelator effect of ferritin, we used the iron chelator DFO and tested whether DFO would suppress EC apoptosis. The data illustrated in FIGS. 20A–C suggest that this is the case. The data in FIGS. 20A–C were generated as follows: (A) 2F–2B ECs were transfected with a β-galactosidase expression vector and exposed to DFO. Gray bars represent ECs treated with Act.D alone and black bars represent ECs treated with TNF-α plus Act.D. (B) 2F–2B ECs were cotransfected as described above in A. Where indicated (+), HO-1 enzymatic activity was inhibited by SnPPIX and iron was chelated by DFO, as described above in A. Gray bars represent ECs treated with Act.D and black bars represent ECs treated with TNF-α plus Act.D. (C) 2F–2B ECs were cotransfected as described above in A. Where indicated (+), CO was removed from the culture medium by Hb and/or iron was chelated by DFO as described above in A and B. Gray bars represent ECs treated with Act.D and black bars represent ECs treated with TNF-α plus Act.D. Results shown (A, B, and C) are the mean±SD from duplicate wells taken from one representative experiment out of three. Induction of EC apoptosis by TNF-α plus Act.D was suppressed by DFO (FIG. 20). When HO-1 activity was inhibited by SnPPIX or the action of CO was suppressed by Hb, DFO was still able to prevent EC apoptosis (FIG. 20).

CO and Iron Chelation have Additive Effects in Protecting ECs from Apoptosis

Figure 21:
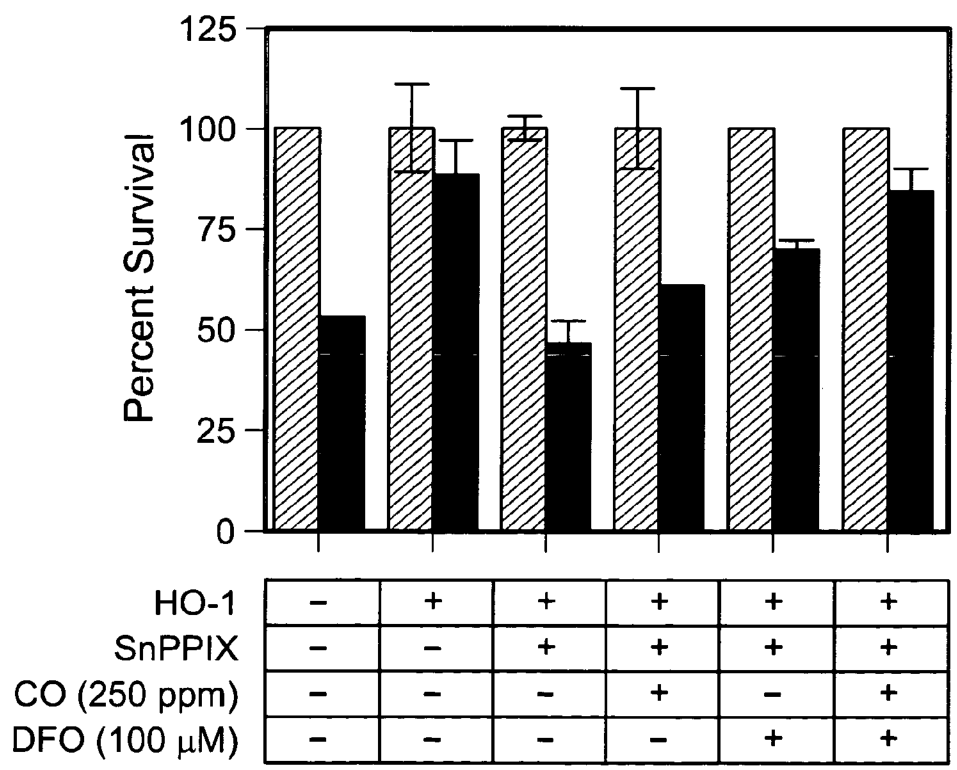
FIG. 21 is a bar graph and grid illustrating that iron chelation and CO have additive effects in suppressing EC apoptosis. (+)=HO-1 transfected cells treated with tin protoporphyrin and/or exogenous DFO (100 μM) and/or CO (250 ppm). Gray bars represent ECs treated with Act.D. Black bars represent ECs treated with TNF-α plus Act.D.
Figure 22A:
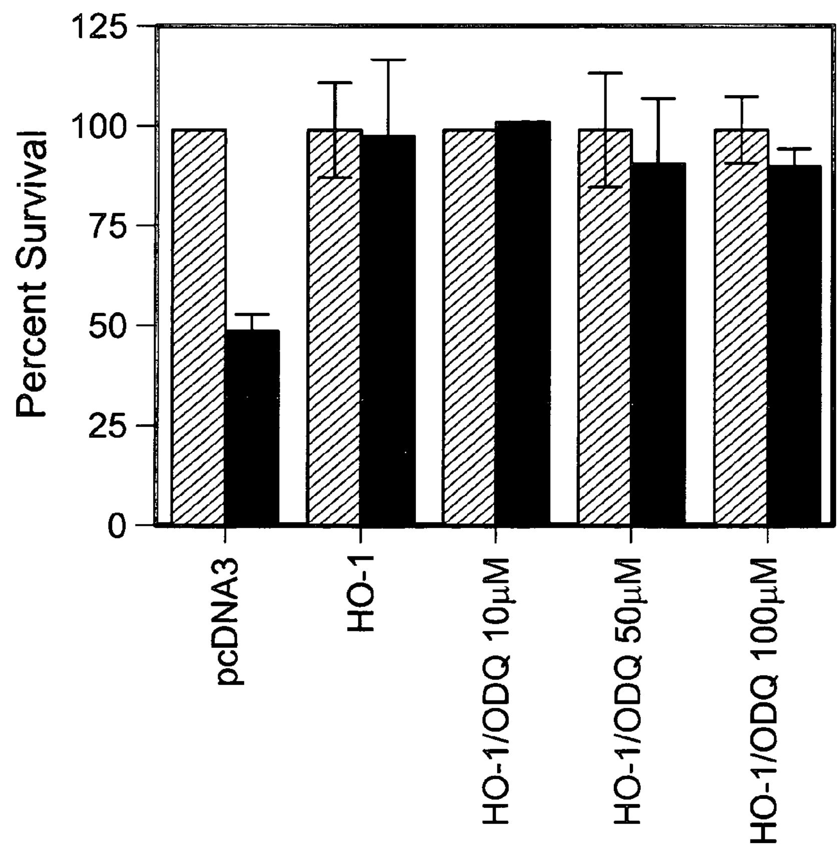
FIG. 22A is a bar graph illustrating that the antiapoptotic effect of HO-1 does not involve a cGMP-dependent pathway. HO-1-transfected cells were exposed to increasing doses of the guanylcyclase inhibitor ODQ. Gray bars represent ECs treated with Act.D alone and black bars represent ECs treated with TNF-α plus Act.D.
Figure 22B:
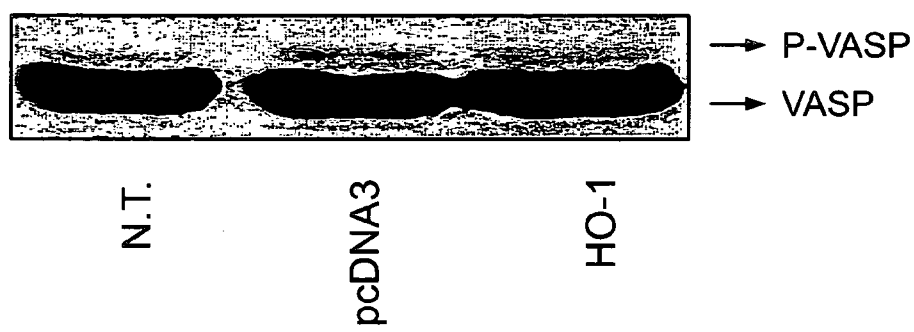
FIG. 22B is a picture of a Western blot illustrating that expression of HO-1 in ECs did not result in a detectable increase of vasodilatator-stimulated phosphoprotein (VASP) phosphorylation. P-VASP (50 kD) and VASP (46 kD) are the phosphorylated and nonphosphorylated forms of VASP, respectively. N.T.=not treated; pcDNA3=cells transfected with pcDNA3; and HO-1=cells transfected with HO-1.
Figure 22C:
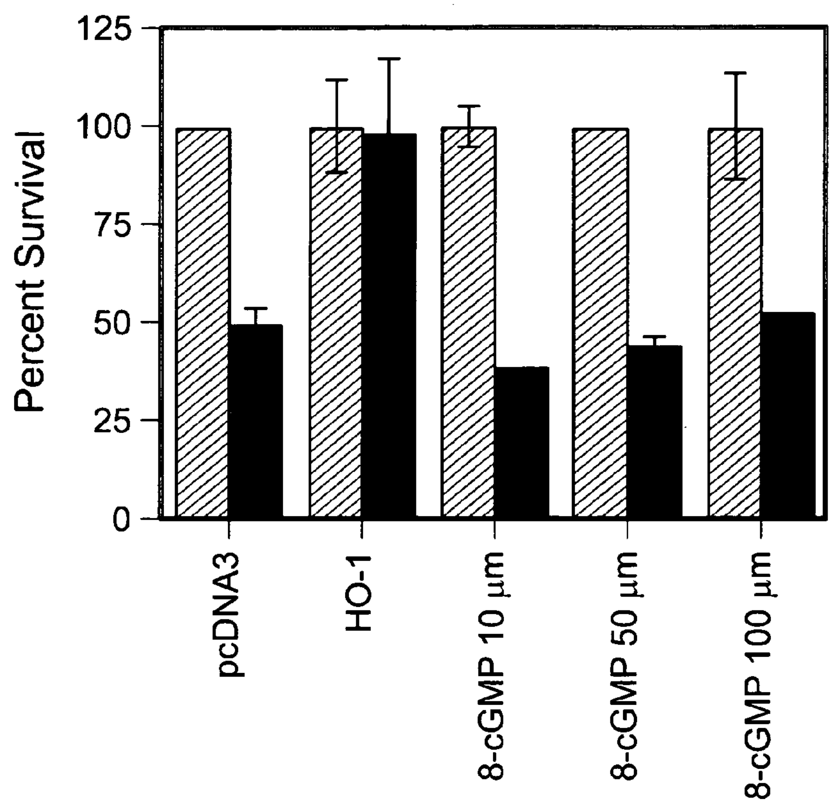
FIG. 22C is a bar graph that illustrates that the cGMP analogue 8-Br-cGMP does not suppress EC apoptosis. Gray bars represent ECs treated with Act.D and black bars represent ECs treated with TNF-α plus Act.D.
Figure 22D:
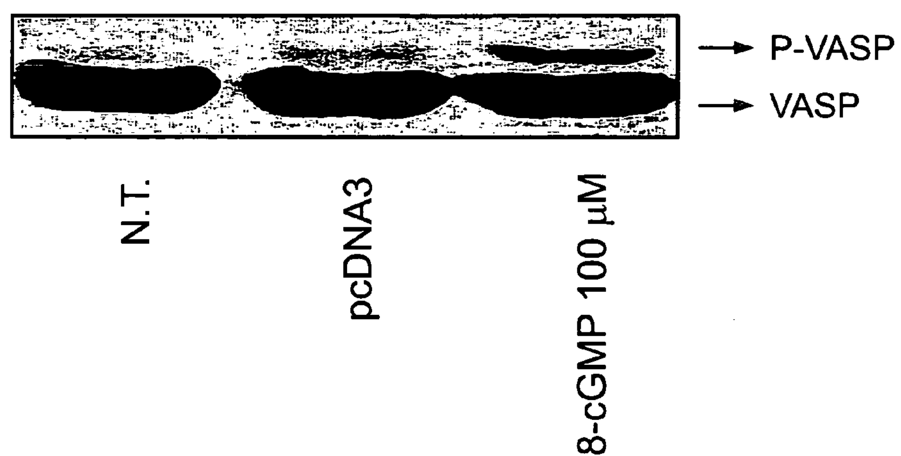
FIG. 22D is a picture of a Western blot illustrating that exposure of ECs to 8-Br-cGMP results in a detectable increase of VASP phosphorylation. N.T.=not treated; pcDNA3=cells transfected with pcDNA3; and HO-1=cells transfected with HO-1.

Given the ability of both CO and iron chelation to suppress EC apoptosis, we asked whether these two biological functions, both engendered by HO-1, would act together to suppress EC apoptosis (FIG. 21). The data in FIG. 21 were generated as follows: 2F–2B ECs were cotransfected with β-galactosidase and HO-1 (β-actin/HO-1) expression vectors. Where indicated (+), cells were treated with the inhibitor of HO enzymatic activity SnPPIX. ECs were exposed to CO (250 ppm) and to the iron chelator DFO. Gray bars represent ECs treated with Act.D and black bars represent ECs treated with TNF-α plus Act.D. The results shown are the mean±SD from duplicate wells taken from one representative experiment out of three. Under inhibition of HO activity by SnPPIX, exposure to low levels of CO (250 ppm) did not suppress EC apoptosis significantly. When used alone, DFO (100 μM) suppressed EC apoptosis, but to a lesser extent than HO-1 (FIG. 21). However, when ECs were exposed to both CO (250 ppm) and DFO (100 μM), inhibition of EC apoptosis was comparable to that achieved with the expression of HO-1.

The Antiapoptotic Effect of HO-1 is not Mediated by Guanylcyclase Activation or cGMP Generation Most biological functions attributed to CO have been linked to its ability to bind guanylcyclase and increase the generation of cGMP. Since cGMP can regulate apoptosis, we tested whether or not the antiapoptotic effect of HO-1 acted via the activation of guanylcyclase and/or the generation of cGMP. The data illustrated in FIGS. 22A–D suggest that this is not the case. The data in FIGS. 22A–D were generated as follows: A) 2F–2B ECs were cotransfected with β-galactosidase and HO-1 (β-actin/HO-1) expression vectors. HO-1-transfected cells were exposed to increasing doses of the guanylcyclase inhibitor ODQ. Gray bars represent ECs treated with Act.D alone and black bars represent ECs treated with TNF-α plus Act.D. The results shown are the mean±SD from duplicate wells taken from one representative experiment out of three. (B) Activation of guanylcyclase was monitored in BAECs by analyzing the phosphorylation of VASP. P-VASP (50 kD) and VASP (46 kD) are the phosphorylated and nonphosphorylated forms of VASP, respectively. (C) 2F–2B ECs were transfected with β-galactosidase or with β-galactosidase plus HO-1 (β-actin/HO-1) expression vectors as described above in A. Where indicated, ECs were exposed to the cGMP analogue 8-Br-cGMP, as described above. Gray bars represent ECs treated with Act.D and black bars represent ECs treated with TNF-α plus Act.D. The results shown are the mean±SD from duplicate wells taken from one representative experiment out of three. (D) Phosphorylation of VASP was analyzed by Western blot as described above in B. N.T., nontreated. Expression of HO-1 in ECs did not result in a detectable increase of cGMP-related functions as illustrated by the absence of VASP phosphorylation, a protein phosphorylated by cyclic nucleotide-dependent protein kinases (protein kinase G-α/β; FIG. 22). This finding is in keeping with that reported by others. Inhibition of guanylcyclase activity by ODQ did not suppress the antiapoptotic effects of HO-1, and the cGMP analogue 8-Br-cGMP failed to suppress EC apoptosis (FIG. 22). That 8-Br-cGMP acted as a cGMP analogue was shown by its ability to induce VASP phosphorylation (FIG. 22). That ODQ was efficient in suppressing guanylcyclase activity in ECs was shown by its ability to prevent constitutive VASP phosphorylation in 2F–2B ECs (data not shown).

HO-1 Increases TNF-α-mediated Activation of p38 MAPK in ECs

Figure 23A:
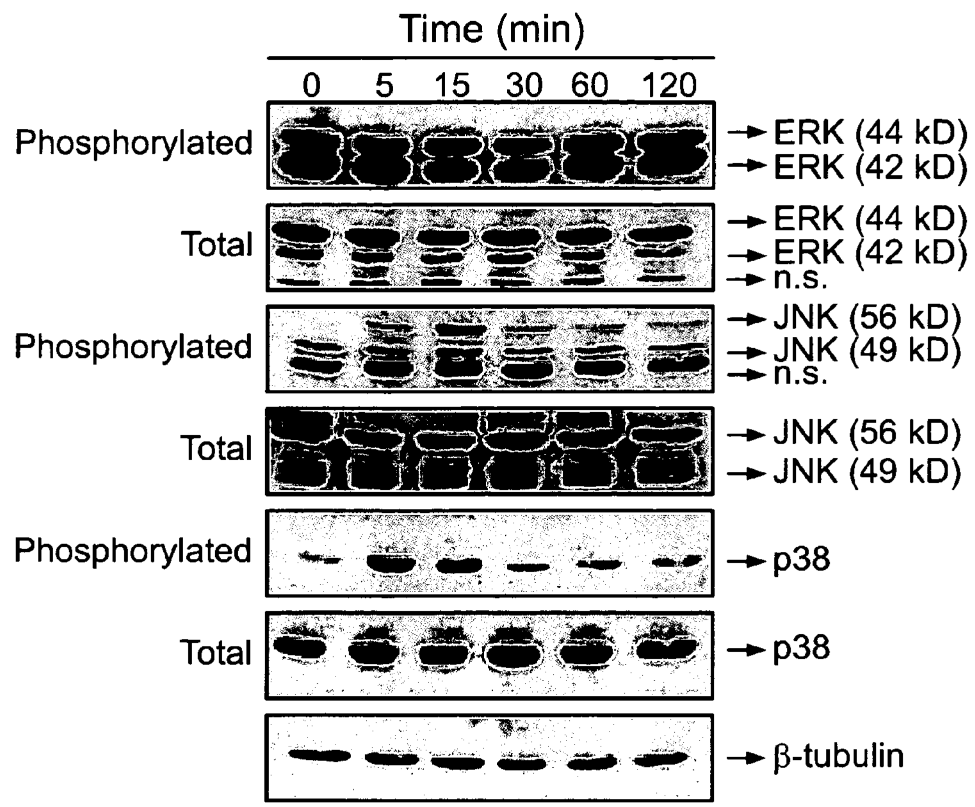
FIG. 23A are pictures of Western blots illustrating that HO-1 increases TNF-α-mediated activation of p38 MAPK in ECs. BAECs were stimulated with TNF-α (10 ng/ml; time 0) and MAPK phosphorylation was monitored by Western blot (0, 5, 15, 30, 60, and 120 min after TNF-α stimulation). "n.s."=nonspecific band.
Figure 23B:
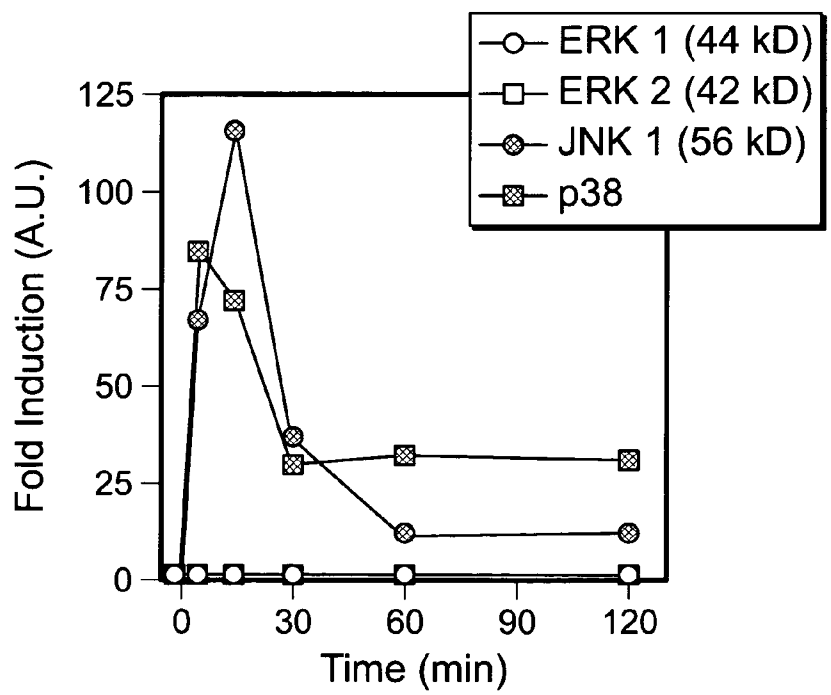
FIG. 23B is a line graph illustrating the quantification of phosphorylation of several MAPKs. The results are presented as fold induction in arbitrary units (A.U.), compared with time 0, before TNF-α stimulation.

Given that HO-1 and/or CO can modulate p38 MAPK activation in monocyte/macrophages (MΦ), we tested whether HO-1 and/or CO would have similar effects in ECs (FIGS. 23A–B). The data in FIG. 23 were generated as follows: (A) BAECs were stimulated with TNF-α (10 ng/ml; time 0) and MAPK phosphorylation was monitored by Western blot (0, 5, 15, 30, 60, and 120 min after TNF-α stimulation) using antibodies directed against the phosphorylated forms of each MAPK. One single membrane was used for all the stainings shown. Experiments were repeated three times with virtually identical results. n.s., nonspecific band. (B) Phosphorylation of different MAPKs was quantified. The results were presented as fold induction in arbitrary units (A.U.), compared with the amount induction at time 0, before TNF-α stimulation. The results in B correspond to the membranes shown in A. Stimulation of ECs with TNF-α resulted in transient activation of JNK and p38 MAPK (FIG. 23), a finding consistent with those of others. ERKs (42 and 44 kD) were constitutively active in resting ECs, and no significant upregulation was detectable after TNF-α stimulation (FIG. 23).

Figure 24A:
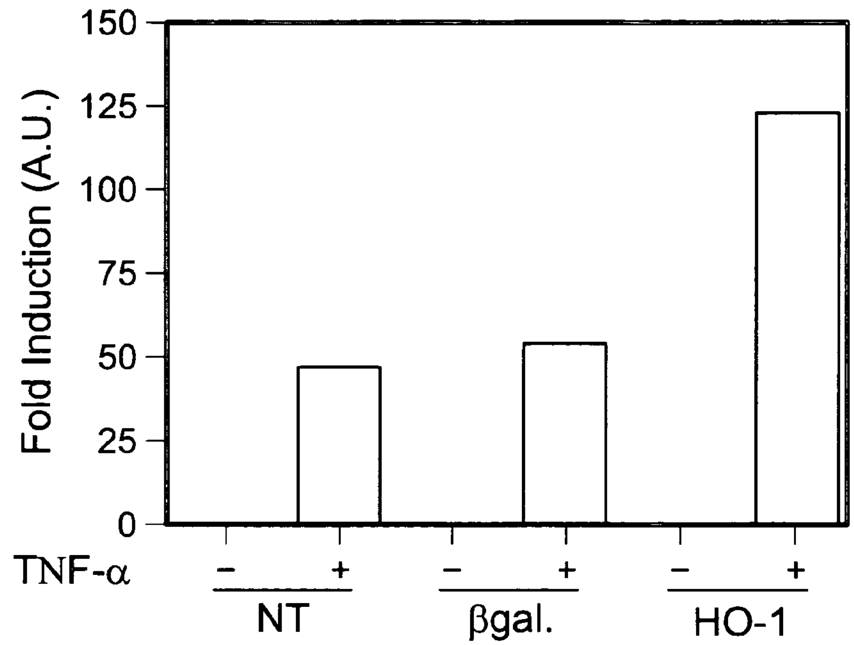
FIG. 24A is a bar graph illustrating that HO-1 modulates p38 MAPK activation in ECs. BAECs were either nontransduced (NT) or transduced with a β-galactosidase (βgal.) or HO-1 recombinant adenovirus, and were left untreated (−) or treated (+) with TNF-α (10 ng/ml for 15 min). Results are presented as fold induction of MAPK activation by TNF-α in arbitrary units (A.U.), compared with time 0, before TNF-α stimulation.
Figure 24B:
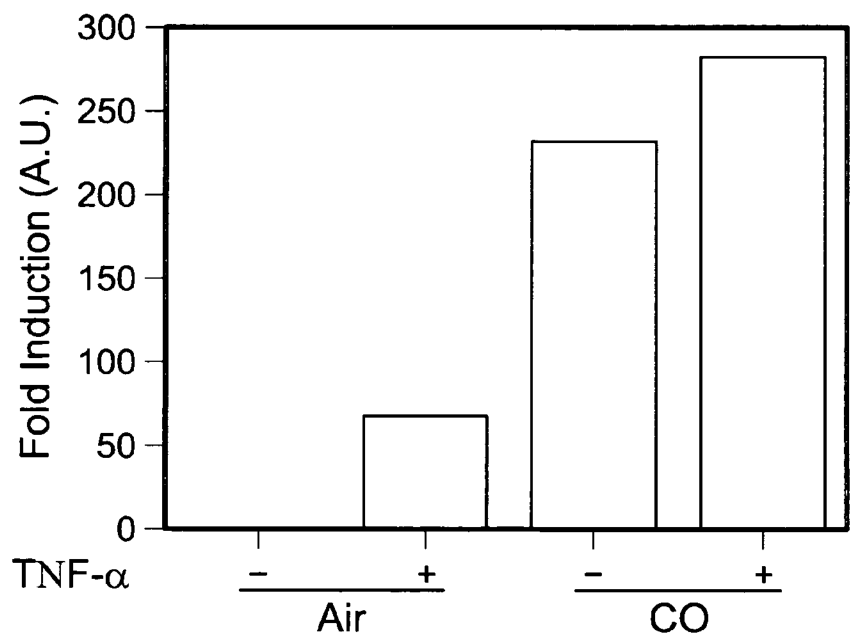
FIG. 24B is a bar graph illustrating that CO modulates p38 MAPK activation in ECs. BAECs were stimulated (+) or not (−) by TNF-α (10 ng/ml, 30 min) in the presence or absence of CO (10,000 ppm). Results are presented as fold induction of MAPK activation by TNF-α in arbitrary units (A.U.), compared with time 0, before TNF-α stimulation.
Figure 25A:
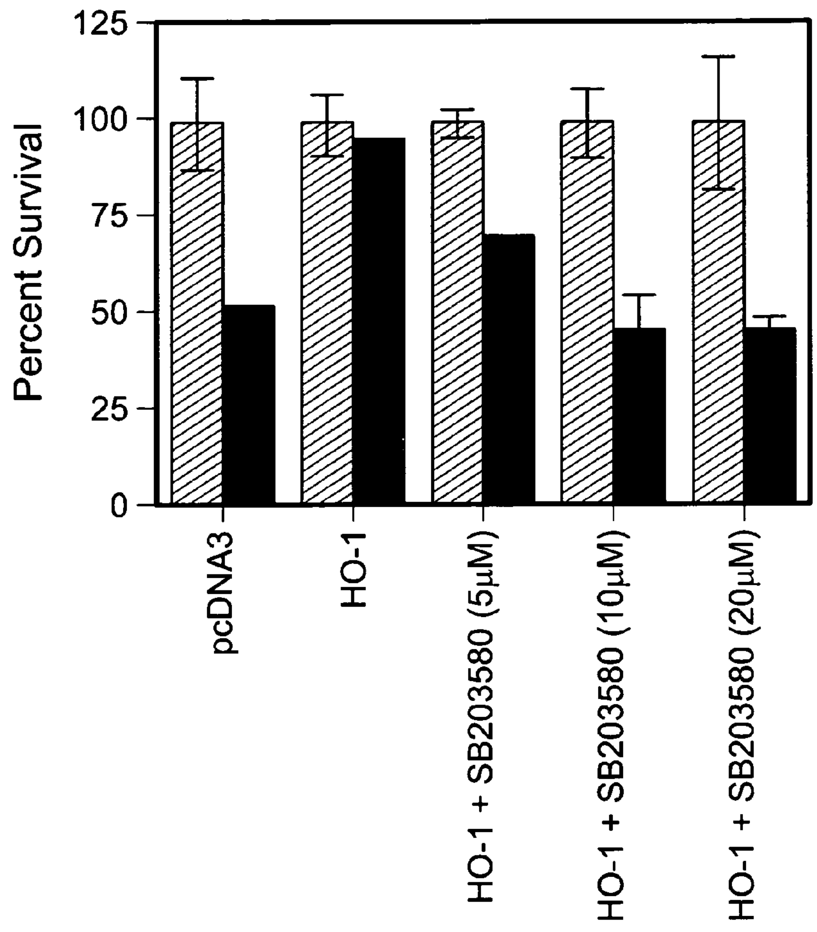
FIG. 25A is a bar graph illustrating that the antiapoptotic action of HO-1 is suppressed when p38 MAPK activation is blocked with pyridinyl imidazol SB203580 (10–20 μM), a specific inhibitor of p38 MAPK. ECs were cotransfected with β-galactosidase, control (pcDNA3), or HO-1 (β-actin/HO-1) expression vectors. Gray bars represent ECs treated with Act.D alone and black bars represent ECs treated with TNF-α plus Act.D.
Figure 25B:
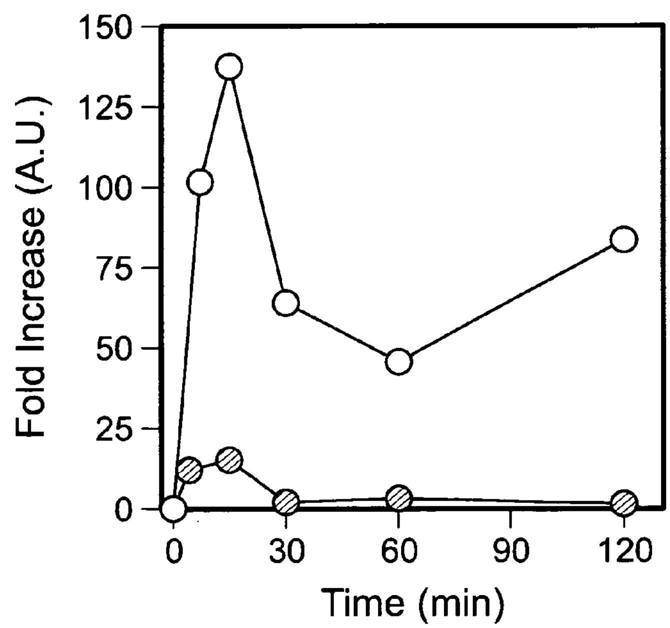
FIG. 25B is a line graph illustrating that activation of p38 MAPK by TNF-α was significantly inhibited (85–95%) in ECs exposed to SB203580 (5–20 μM), compared with control ECs stimulated by TNF-α in the absence of SB203580. BAECs were transfected with a control (pcDNA3) vector and stimulated with TNF-α in the presence (●) or absence (○) of the p38 kinase inhibitor SB203580 (20 μM). MAPK phosphorylation was monitored by Western blot (0, 5, 15, 30, 60, and 120 min after TNF-α stimulation).
Figure 25C:
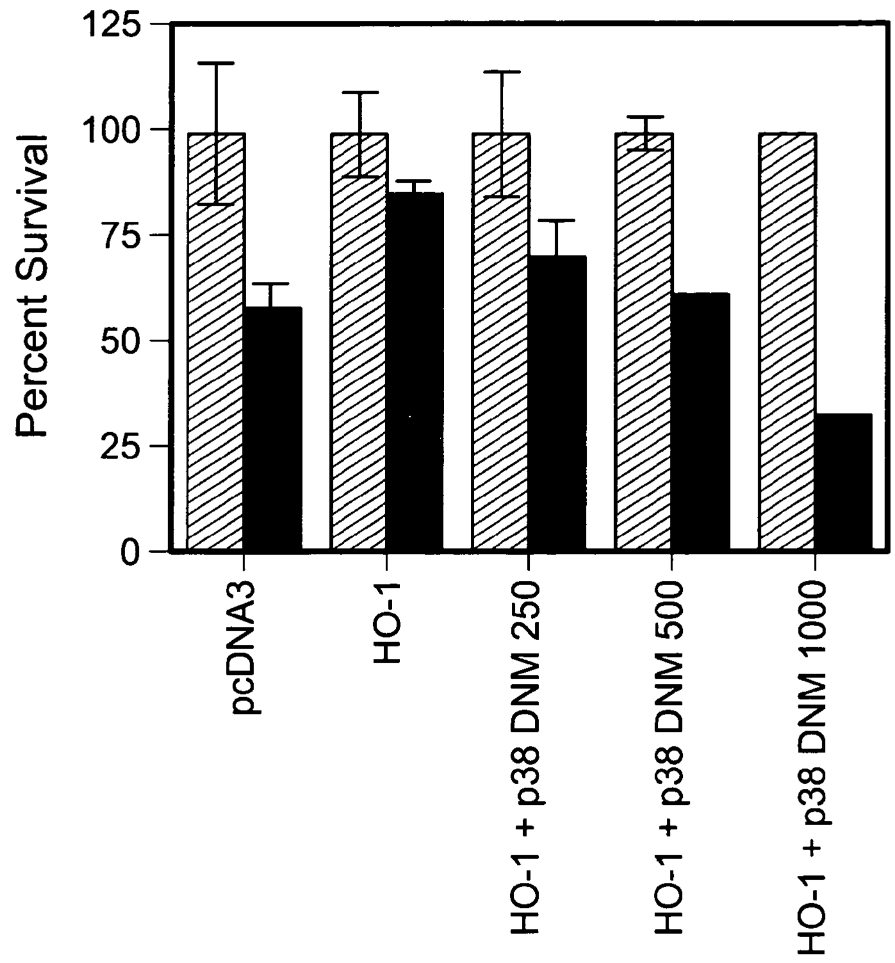
FIG. 25C is a bar graph illustrating that overexpression of a dominant negative mutant of p38/CSBP1 suppressed the ability of HO-1 to prevent EC apoptosis. ECs were cotransfected with β-galactosidase, control, HO-1 (β-actin/HO-1), and where indicated with a phosphorylation-deficient p38/CSBP1 dominant negative mutant (DNM) expression vector. The values indicate the amount of vector used, in nanograms of DNA per $300\times10^3$ cells. Gray bars represent ECs treated with Act.D and black bars represent ECs treated with TNF-α plus Act.D.
Figure 25D:
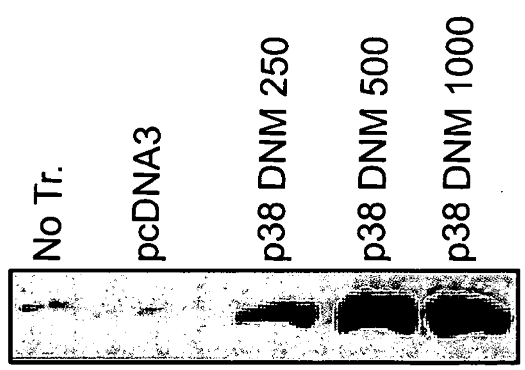
FIG. 25D is a picture of a Western blot illustrating that the inhibitory effect was dose dependent in that increasing amounts of the p38/CSBP1 dominant negative mutant were more efficient in suppressing the antiapoptotic action of HO-1. No Tr., nontransfected ECs.

The data in FIGS. 24A–B were generated as follows: (A) BAECs were either nontransduced (NT), transduced with a β-galactosidase (βgal.) adenovirus, or transduced with HO-1 recombinant adenovirus, and were left untreated (−) or treated (+) with TNF-α (10 ng/ml for 15 min). p38 MAPK phosphorylation was monitored by Western blot using antibodies directed against the phosphorylated forms of each MAPK. Results are presented as fold induction of MAPK activation by TNF-α in arbitrary units (A.U.), compared with the amount of induction at time 0, before TNF-α stimulation. (B) BAECs were stimulated (+) or not (−) by TNF-α (10 ng/ml, 30 min) in the presence or absence of CO (10,000 ppm). Phosphorylation of p38 MAPK was quantified as in A. The results are presented as fold induction of MAPK activation by TNF-α in arbitrary units (A.U.). Recombinant adenovirus mediated overexpression of HO-1 potentiated the ability of TNF-α to activate p38 MAPK (FIG. 24), but not to activate JNK (data not shown). Overexpression of β-galactosidase had no detectable effect on the activation of either p38 MAPK or JNK by TNF-α. Exposure of ECs to exogenous CO activated p38 MAPK even in the absence of TNF-α (FIG. 24).

The Mechanism by which CO Prevents EC Apoptosis Acts Via the Activation of p38 MAPK Since p38 MAPK can regulate apoptosis, we investigated whether the ability of HO-1 to modulate p38 MAPK activation was linked to its ability to prevent EC apoptosis. We found that this is the case (FIGS. 25A–D). The data in FIGS. 25A–D were generated as follows: A) 2F–2B ECs were cotransfected with β-galactosidase, control (pcDNA3), or HO-1 (β-actin/HO-1) expression vectors. Where indicated, ECs were treated with the p38 kinase inhibitor SB203580. Gray bars represent ECs treated with Act.D alone and black bars represent ECs treated with TNF-α plus Act.D. The results shown are the mean±SD from duplicate wells taken from one representative experiment out of three. (B) BAECs were transfected with a control (pcDNA3) vector and stimulated with TNF-α in the presence (●) or absence (○) of the p38 kinase inhibitor SB203580 (20 μM). MAPK phosphorylation was monitored by Western blot (0, 5, 15, 30, 60, and 120 min after TNF-α stimulation) using antibodies directed against the phosphorylated forms of each MAPK. (C) 2F–2B ECs were cotransfected with β-galactosidase, control, HO-1 (β-actin/HO-1), and where indicated with a phosphorylation-deficient p38/CSBP1 dominant negative mutant (DNM) expression vector. The values indicate the amount of vector used, in nanograms of DNA per $300\times10^3$ cells. Apoptosis was induced as in A. Gray bars represent ECs treated with Act.D and black bars represent ECs treated with TNF-α plus Act.D. The results shown are the mean±SD from duplicate wells taken from one representative experiment out of three. (D) The expression of the p38/CSBP1 dominant negative mutant was confirmed by Western blot using an anti-p38 specific antibody. No Tr., nontransfected ECs. The antiapoptotic action of HO-1 was suppressed when p38 MAPK activation was blocked by the pyridinyl imidazol SB203580 (10–20 μM), a specific inhibitor of p38 MAPK. This effect was dose dependent in that increasing concentrations of SB203580 were increasingly efficient in suppressing the antiapoptotic action of HO-1 (FIG. 25). Inhibition of p38 MAPK activation per se did not sensitize ECs to TNF-α-mediated apoptosis (data not shown). As expected, activation of p38 MAPK by TNF-α was significantly inhibited (85–95%) in ECs exposed to SB203580 (5–20 μM), compared with control ECs stimulated by TNF-α in the absence of SB203580 (FIG. 25). Similarlyto SB203580, overexpression of a dominant negative mutant of p38/CSBP1 also suppressed TNF-α-mediated p38 MAPK activation, as tested by a kinase assay using the activating transcription factor (ATF)-2 as a substrate (data not shown). Overexpression of this dominant negative mutant suppressed the ability of HO-1 to prevent EC apoptosis (FIG. 25). This inhibitory effect was dose dependent in that increasing amounts of the p38/CSBP1 dominant negative mutant were more efficient in suppressing the antiapoptotic action of HO-1 (FIG. 25).

EXAMPLE IV

Protocols for the Treatment of Organs and Tissues, a Donor, and a Recipient During Transplantation Procedures The following example illustrates protocols for use in treating a donor, and organ, and a recipient with carbon monoxide during a transplantation procedure. Any one or more of the following procedures may be used in a given transplantation procedure.

Treatment of a Donor

Prior to harvesting an organ or tissue, the donor can be treated with inhaled carbon monoxide (250 ppm) for one hour. Treatment can be administered at doses varying from 10 ppm to 1000 ppm for times varying from one hour to six hours, or for the entire period from the moment when it becomes possible to treat a brain-dead (cadaver) donor to the time the organ is removed. Treatment should start as soon as possible following the declaration that brain death is present. In some applications, it may be desirable to begin treatment before brain death.

For non-human animals (e.g., pigs) to be used as xenotransplantation donors, the live animal can be treated with relatively high levels of inhaled carbon monoxide, as desired, so long as the carboxyhemoglobin so produced does not compromise the viability and function of the organ to be transplanted. For example, one could use levels greater than 500 ppm (e.g., 1000 ppm or higher, and up to 10,000 ppm, particularly for brief times).

Treatment of the Organ In Situ

Before an organ is harvested from a donor, it can be flushed with a solution, e.g., a buffer or medium, without red blood cells while it is still in the donor. The intent is to flush the organ with a solution saturated with carbon monoxide and maintained in a carbon monoxide atmosphere so that the carbon monoxide content remains at saturation. Flushing can take place for a time period of at least 10 minutes, e.g., 1 hour, several hours, or longer. The solution should ideally deliver the highest concentration of carbon monoxide possible to the cells of the organ.

Treatment of an Organ or Tissue

The organ or tissue can be preserved in a medium that includes carbon monoxide from the time it is removed from the donor to the time it is transplanted to the recipient. This can be performed by maintaining the organ or tissue in the medium comprising CO, or by perfusing it with such a medium. Since this occurs ex vivo rather than in an animal, very high concentrations of CO gas can be used (e.g., 10,000 ppm) to keep the medium saturated with CO.

Treatment of a Recipient

The recipient can be treated with carbon monoxide. Treatment can begin on the day of transplantation at least 30 minutes before surgery begins. Alternatively, it could begin at least 30 minutes before re-perfusion of the organ in the recipient. It can be continued for at least 30 minutes, e.g., 1 hour. Carbon monoxide doses between 10 ppm and 3000 ppm can be delivered for varying times, e.g., minutes or hours, and can be administered on the day of and on days following transplantation. For example, a recipient can inhale a concentration of carbon monoxide, e.g., 3000 ppm, for three consecutive 10 second breath holds. Alternatively, the recipient can inhale, say 200 ppm for an extended time, such as 20 days. Carboxyhemoglobin concentrations can be utilized as a guide for appropriate administration of carbon monoxide to a patient. Usually, treatments for recipients should not raise carboxyhemoglobin levels above those considered to pose an acceptable risk for a patient in need of a transplant.

OTHER EMBODIMENTS

It is to be understood that, while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of transplanting an organ, the method comprising:

(a) administering to a donor by inhalation a gaseous pharmaceutical composition comprising carbon monoxide;

(b) obtaining from the donor an organ selected from the group consisting of: kidney, liver, heart, skin, small intestine, and pancreas; and (c) transplanting the organ into a recipient, wherein the amount of carbon monoxide administered to the donor in step (a) is sufficient to enhance survival or function of the organ after transplantation into the recipient.

2. The method of claim 1, wherein the pharmaceutical composition is administered to a live donor.

3. The method of claim 1, wherein the pharmaceutical composition is administered to a brain-dead donor.

4. The method of claim 1, wherein the pharmaceutical composition comprising carbon monoxide is administered to the donor prior to and following brain death.

5. The method of claim 1, further comprising treating the organ in situ in the donor with a second pharmaceutical composition comprising carbon monoxide.

6. The method of claim 1, further comprising treating the organ ex vivo, prior to the transplantation step, with a second pharmaceutical composition comprising carbon monoxide.

7. The method of claim 1, further comprising the step of administering to the recipient by inhalation a second gaseous pharmaceutical composition comprising carbon monoxide before, during, or after step (c).

8. The method of claim 7, wherein the second pharmaceutical composition is administered to the recipient before (c).

9. The method of claim 7, wherein the pharmaceutical composition comprising carbon monoxide is administered to the recipient during (c).

10. The method of claim 7, wherein the pharmaceutical composition comprising carbon monoxide is administered to the recipient after (c).

11. The method of claim 7, wherein the pharmaceutical composition comprising carbon monoxide is administered to the recipient before and during (c).

12. The method of claim 7, wherein the pharmaceutical composition comprising carbon monoxide is administered to the recipient before and after (c).

13. The method of claim 7, wherein the pharmaceutical composition comprising carbon monoxide is administered to the recipient before, during, and after (c).

14. The method of claim 1, wherein the organ is a liver.

15. The method of claim 1, wherein the organ is a kidney.

16. The method of claim 1, wherein the organ is a heart.

17. The method of claim 1, wherein the organ is a pancreas.

18. The method of claim 1, wherein the organ is a small intestine.

19. The method of claim 1, wherein the organ is skin.

20. The method of claim 1, wherein the donor is of a species different from that of the recipient.

21. The method of claim 1, wherein the donor and the recipient are of the same species.

22. The method of claim 1, wherein both the donor and the recipient are non-human animals.

23. The method of claim 1, wherein both the donor and the recipient are humans.

24. The method of claim 1, wherein the donor is a non-human animal and the recipient is a human.

25. The method of claim 1, wherein, prior to step (a), the donor is identified as being suitable for donating an organ.

26. The method of claim 1, wherein the pharmaceutical composition administered to the donor is supplied in the form of a pressurized gas in a vessel.

27. The method of claim 1, wherein the pharmaceutical composition is administered to the donor during (b).

28. The method of claim 2, wherein, prior to step (a), the donor is identified as being suitable for donating an organ.

29. The method of claim 2, wherein the pharmaceutical composition administered to the donor is supplied in the form of a pressurized gas in a vessel.

30. The method of claim 2, wherein the pharmaceutical composition is administered to the donor during (b).

31. The method of claim 5, wherein, prior to step (a), the donor is identified as being suitable for donating an organ.

32. The method of claim 5, wherein the pharmaceutical composition administered to the donor is supplied in the form of a pressurized gas in a vessel.

33. The method of claim 5, wherein the pharmaceutical composition is administered to the donor during (b).

34. The method of claim 14, wherein, prior to step (a), the donor is identified as being suitable for donating an organ.

35. The method of claim 14, wherein the pharmaceutical composition administered to the donor is supplied in the form of a pressurized gas in a vessel.

36. The method of claim 14, wherein the pharmaceutical composition is administered to the donor during (b).

37. The method of claim 15, wherein, prior to step (a), the donor is identified as being suitable for donating an organ.

38. The method of claim 15, wherein the pharmaceutical composition administered to the donor is supplied in the form of a pressurized gas in a vessel.

39. The method of claim 15, wherein the pharmaceutical composition is administered to the donor during (b).

40. The method of claim 16, wherein, prior to step (a), the donor is identified as being suitable for donating an organ.

41. The method of claim 16, wherein the pharmaceutical composition administered to the donor is supplied in the form of a pressurized gas in a vessel.

42. The method of claim 16, wherein the pharmaceutical composition is administered to the donor during (b).

43. The method of claim 17, wherein, prior to step (a), the donor is identified as being suitable for donating an organ.

44. The method of claim 17, wherein the pharmaceutical composition administered to the donor is supplied in the form of a pressurized gas in a vessel.

45. The method of claim 17, wherein the pharmaceutical composition is administered to the donor during (b).

46. The method of claim 18, wherein, prior to step (a), the donor is identified as being suitable for donating an organ.

47. The method of claim 18, wherein the pharmaceutical composition administered to the donor is supplied in the form of a pressurized gas in a vessel.

48. The method of claim 18, wherein the pharmaceutical composition is administered to the donor during (b).

49. The method of claim 21, wherein, prior to step (a), the donor is identified as being suitable for donating an organ.

50. The method of claim 21, wherein the pharmaceutical composition administered to the donor is supplied in the form of a pressurized gas in a vessel.

51. The method of claim 21, wherein the pharmaceutical composition is administered to the donor during (b).

52. The method of claim 23, wherein, prior to step (a), the donor is identified as being suitable for donating an organ.

53. The method of claim 23, wherein the pharmaceutical composition administered to the donor is supplied in the form of a pressurized gas in a vessel.

54. The method of claim 23, wherein the pharmaceutical composition is administered to the donor during (b).

* * * * *

Adverse Decision in Interference

Patent No. 7,238,469, Bach H. Fritz, Leo E. Otterbein, Miguel P. Soares and Jeanne Gose, CARBON MONOXIDE IMPROVES OUTCOMES IN TISSUE AND ORGAN TRANSPLANTS AND SUPPRESSES APOPTOSIS, Interference No. 105,619, final judgment adverse to the patentees rendered July 14, 2008, as to Count 1: claims 1-14, 20-36, 49-54; Count 2: 1-13, 16, 20-33, 40-42 and 49-54; and Count 3: claims 46, 49-51, 53, 56-62, 65 and 69.

*(Official Gazette October 7, 2008)*